United States Patent
Johnson et al.

(10) Patent No.: US 8,855,768 B1
(45) Date of Patent: Oct. 7, 2014

(54) CAPACITOR FOR AN ACTIVE IMPLANTABLE MEDICAL DEVICE (AIMD) FOR HANDLING HIGH RF POWER INDUCED IN AN IMPLANTED LEAD FROM AN EXTERNAL RF FIELD

(71) Applicant: Greatbatch Ltd., Clarence, NY (US)

(72) Inventors: Robert Shawn Johnson, North Tonawanda, NY (US); Dominick J. Frustaci, Williamsville, NY (US); Warren S. Dabney, Lake Oswego, OR (US); Robert A. Stevenson, Canyon Country, CA (US); Keith W. Seitz, Clarence Center, NY (US); Christine A. Frysz, Orchard Park, NY (US); Thomas Marzano, East Amherst, NY (US); Richard L. Brendel, Carson City, NV (US); John E. Roberts, Carson City, NV (US); William Thiebolt, Tonawanda, NY (US); Christopher M. Williams, Lancaster, NY (US); Jason Woods, Carson City, NV (US); Buehl E. Truex, Glendora, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/088,849

(22) Filed: Nov. 25, 2013

Related U.S. Application Data

(63) Continuation of application No. 13/408,020, filed on Feb. 29, 2012, now abandoned.

(60) Provisional application No. 61/448,069, filed on Mar. 1, 2011.

(51) Int. Cl.
  *H01G 4/35* (2006.01)
  *A61N 1/05* (2006.01)
  *A61N 1/08* (2006.01)

(52) U.S. Cl.
  CPC ..... *A61N 1/08* (2013.01); *A61N 1/05* (2013.01)
  USPC .............................. 607/36; 361/302; 361/311

(58) Field of Classification Search
  CPC .. A61N 1/3718; A61N 1/3754; H03H 1/0007
  USPC .......................................................... 607/36
  See application file for complete search history.

(56) References Cited

U.S. PATENT DOCUMENTS

| 5,333,095 A | 7/1994 | Stevenson et al. |
| 5,978,204 A * | 11/1999 | Stevenson ..................... 361/303 |

(Continued)

OTHER PUBLICATIONS

Balinis, Constantine A., "Advanced Engineering Electromagnetics", John Wiley & Sons, 1989.

(Continued)

*Primary Examiner* — Carl H Layno
*Assistant Examiner* — Erin Piateski
(74) *Attorney, Agent, or Firm* — Michael F. Scalise

(57) ABSTRACT

An RF filter for an active medical device (AMD), for handling RF power induced in an associated lead from an external RF field at a selected MRI frequency or range frequencies includes a capacitor having a capacitance of between 100 and 10,000 picofarads, and a temperature stable dielectric having a dielectric constant of 200 or less and a temperature coefficient of capacitance (TCC) within the range of plus 400 to minus 7112 parts per million per degree centigrade. The capacitor's dielectric loss tangent in ohms is less than five percent of the capacitor's equivalent series resistance (ESR) at the selected MRI RF frequency or range of frequencies.

31 Claims, 51 Drawing Sheets

(56) References Cited

U.S. PATENT DOCUMENTS

| | | | |
|---|---|---|---|
| 6,539,253 B2 | 3/2003 | Thompson et al. | |
| 6,765,779 B2 | 7/2004 | Stevenson | |
| 6,925,328 B2 | 8/2005 | Foster et al. | |
| 7,363,090 B2 | 4/2008 | Halperin et al. | |
| 7,387,928 B2* | 6/2008 | Cheung | 438/239 |
| 7,517,769 B2* | 4/2009 | Van Schuylenbergh et al. | 438/381 |
| 7,689,288 B2 | 3/2010 | Stevenson et al. | |
| 7,844,319 B2 | 11/2010 | Susil et al. | |
| 7,853,324 B2 | 12/2010 | Stevenson et al. | |
| 8,095,224 B2 | 1/2012 | Truex et al. | |
| 2003/0050557 A1 | 3/2003 | Susil et al. | |
| 2003/0053284 A1* | 3/2003 | Stevenson et al. | 361/302 |
| 2003/0171792 A1* | 9/2003 | Zarinetchi et al. | 607/61 |
| 2003/0179536 A1* | 9/2003 | Stevenson et al. | 361/302 |
| 2003/0213605 A1* | 11/2003 | Brendel et al. | 174/35 R |
| 2005/0007718 A1* | 1/2005 | Stevenson et al. | 361/118 |
| 2005/0248907 A1* | 11/2005 | Stevenson et al. | 361/306.2 |
| 2006/0221543 A1* | 10/2006 | Stevenson et al. | 361/302 |
| 2007/0035910 A1* | 2/2007 | Stevenson | 361/302 |
| 2007/0112398 A1* | 5/2007 | Stevenson et al. | 607/63 |
| 2008/0140149 A1* | 6/2008 | John et al. | 607/45 |
| 2009/0036944 A1* | 2/2009 | Fonte | 607/36 |
| 2009/0270948 A1* | 10/2009 | Nghiem et al. | 607/60 |
| 2009/0312835 A1* | 12/2009 | Stevenson | 623/3.1 |
| 2010/0023000 A1* | 1/2010 | Stevenson et al. | 606/33 |
| 2010/0198312 A1 | 8/2010 | Stevenson et al. | |
| 2010/0217262 A1 | 8/2010 | Stevenson et al. | |

OTHER PUBLICATIONS

Ennis, J. et al., "Cautions About the Use of Equivalent Series Resistance (ESR) in Specifying Capacitors", 1993 Proceedings, 13th Capacitor and Resistor Technology Symposium, Mar. 8, 1993, 58-64.

Gabriel, C. et al., "Dielectric Properties of Biological Tissues: Literature Survey", IOP Publishing Ltd., 1996.

Gabriel, S. et al., "Dielectric Properties of Biological Tissues: Measurements and the Frequency Range 0 Hz to 20 GHz", Phys. Med. Biol. 41, 1996, IOP Publishing Ltd., 1996, 2251-2269.

Gabriel, S. et al., "The Dielectric Properties of Biological Tissues: Parametric Models for the Dielectric Spectrum of Tissues", Phys. Med. Bio. 41, IOP Publishing Ltd., 1996, 2271-2293.

Luchinger, Roger C., "Safety Aspects of Cardiac Pacemakers in Magnetic Resonance Imaging", A dissertation submitted to the Swiss Federal Institute of Technology Zurich., 2002.

Search, , "European Search Report for EP12157697.9", Jul. 5, 2012.

Susil, Robert C. et al., "Multifunctional Interventional Devices for MRI: A Combined Electrophysiology/MRI Catheter", Magnetic Resonance in Medicine, 47, 2002, 594-600.

* cited by examiner

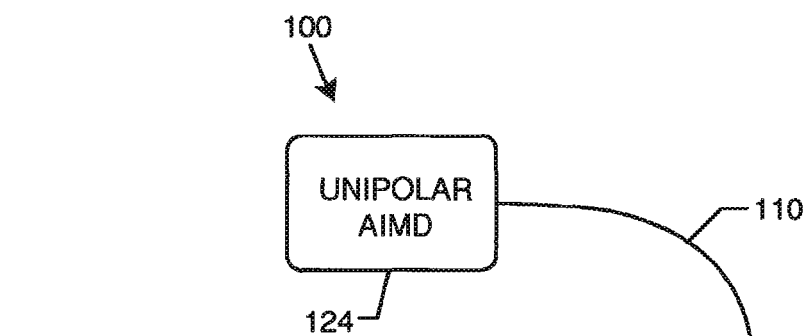
FIG. 6
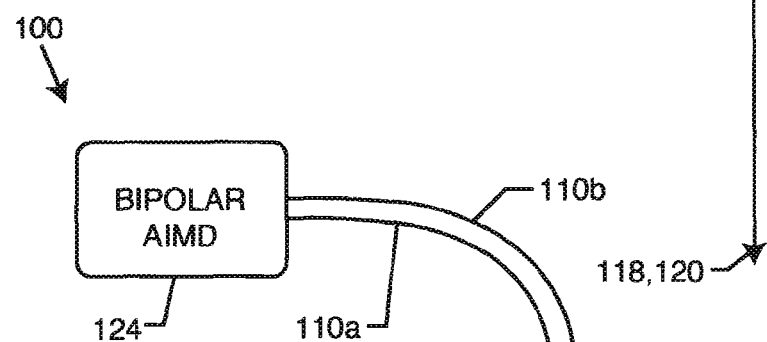
FIG. 7
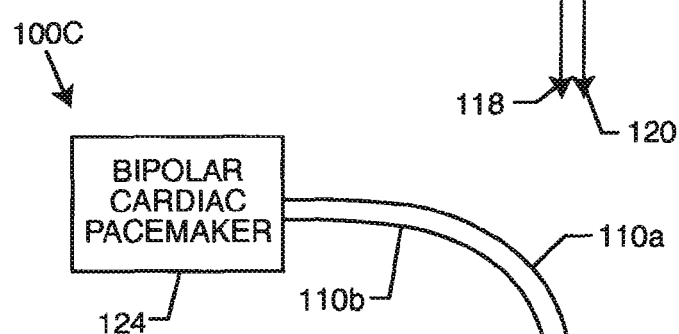
FIG. 8
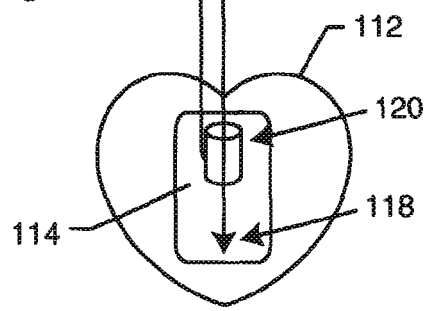

BODY
FLUID
SIDE

BODY
FLUID
SIDE

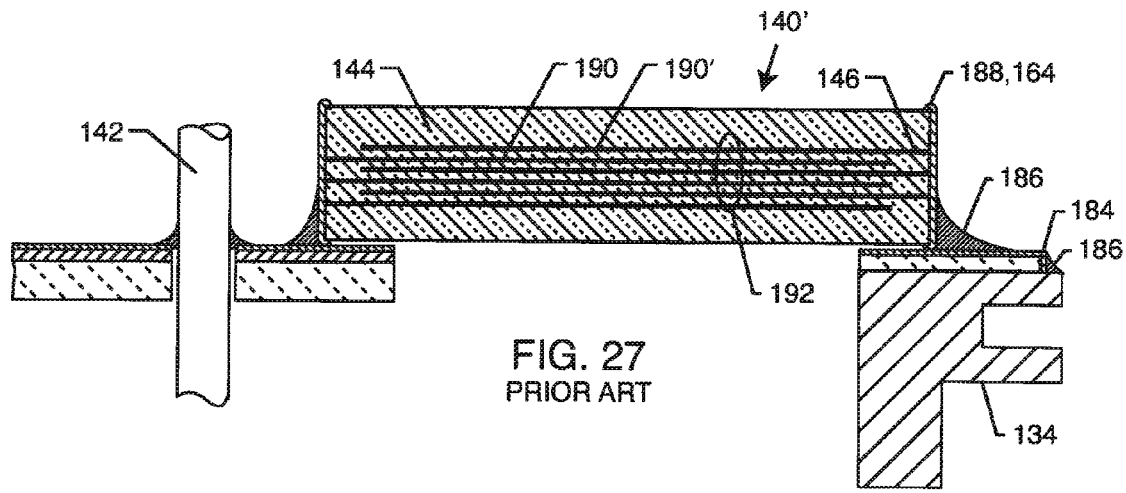
FIG. 27
PRIOR ART
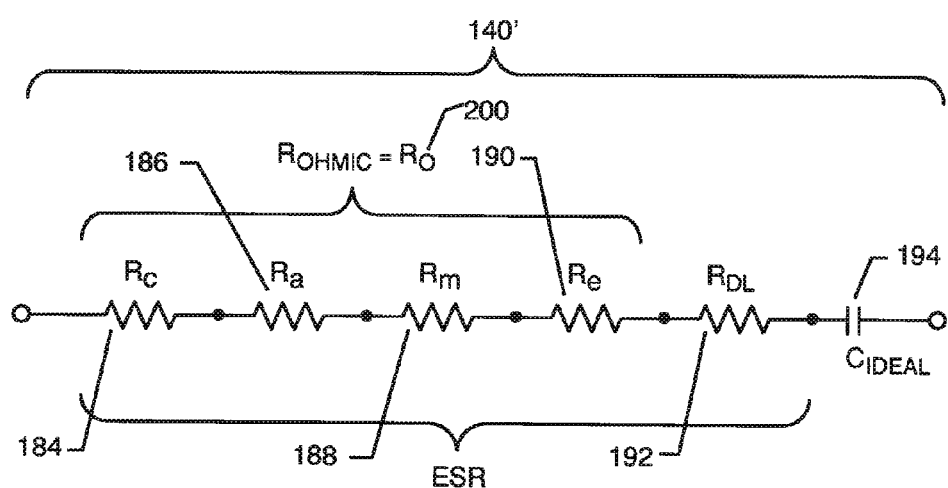
FIG. 28
$$c = \frac{kA\,(n-1)}{d}$$
Where
A = Active Area
c = Capacitance
k = Dielectric Constant
n = Number of Electrode Plates
d = Dielectric Thickness
FIG. 29

$$X_c = -j\left(\frac{1}{\omega C}\right)$$

$$DF = \frac{i^2 \, ESR}{i^2 \, |X_c|} = (\omega C) \cdot (ESR) = 1/Q$$

$$\tan\delta = \frac{ESR}{|X_c|} = DF$$

C = Capacitance
$R_{DL}$ = R dielectric
$R_O$ = R ohmic loss
IR = Insulation Resistance
ESL = Equivalent Series Inductance
ESR = Equivalent Series Resistance Example of Losses in a 2000 P.F. X7R Capacitor DF is a percentage of Xc ≠ dielectric loss tangent Example: 2% DF Dielectric; 2000 picofarad FT   (2.5% MAX RS-198C)

| Frequency | Xc (Ω) | DF (Ω) | R (Ω) | ESR = DF+R (Ω) |
|---|---|---|---|---|
| 1 kHz | 79,599.54 | 1591.55 | 0.432 | 1591.98 |
| 1 MHz | 79.58 | 1.59 | 0.432 | 2.02 |
| 10 MHz | 7.96 | 0.159 | 0.432 | 0.59 |
| 100 MHz | 0.796 | 0.016 | 0.432 | 0.45 |
| 500 MHz | 0.159 | 0.003 | 0.432 | 0.44 |

FIG. 36

Example of Losses in a 2000 P.F. COG (NPO) Capacitor

DF is a percentage of Xc

Example: 0.15% DF Dielectric; 2000 picofarad FT

| Frequency | Xc (Ω) | DF (Ω) | R (Ω) | ESR = DF+R (Ω) |
|---|---|---|---|---|
| 1 kHz | 79,577.54 | 119.40 | 0.2 | 119.6 |
| 1 MHz | 79.58 | 0.12 | 0.2 | 0.32 |
| 10 MHz | 7.96 | 0.012 | 0.2 | 0.212 |
| 100 MHz | 0.796 | 0.001 | 0.2 | 0.201 |
| 500 MHz | 0.159 | 0.0 | 0.2 | 0.200 |

FIG. 37

$$R_{et} = \frac{1}{\frac{1}{R_{e_1}} + \frac{1}{R_{e_2}} + \cdots \frac{1}{R_{e_n}}}$$

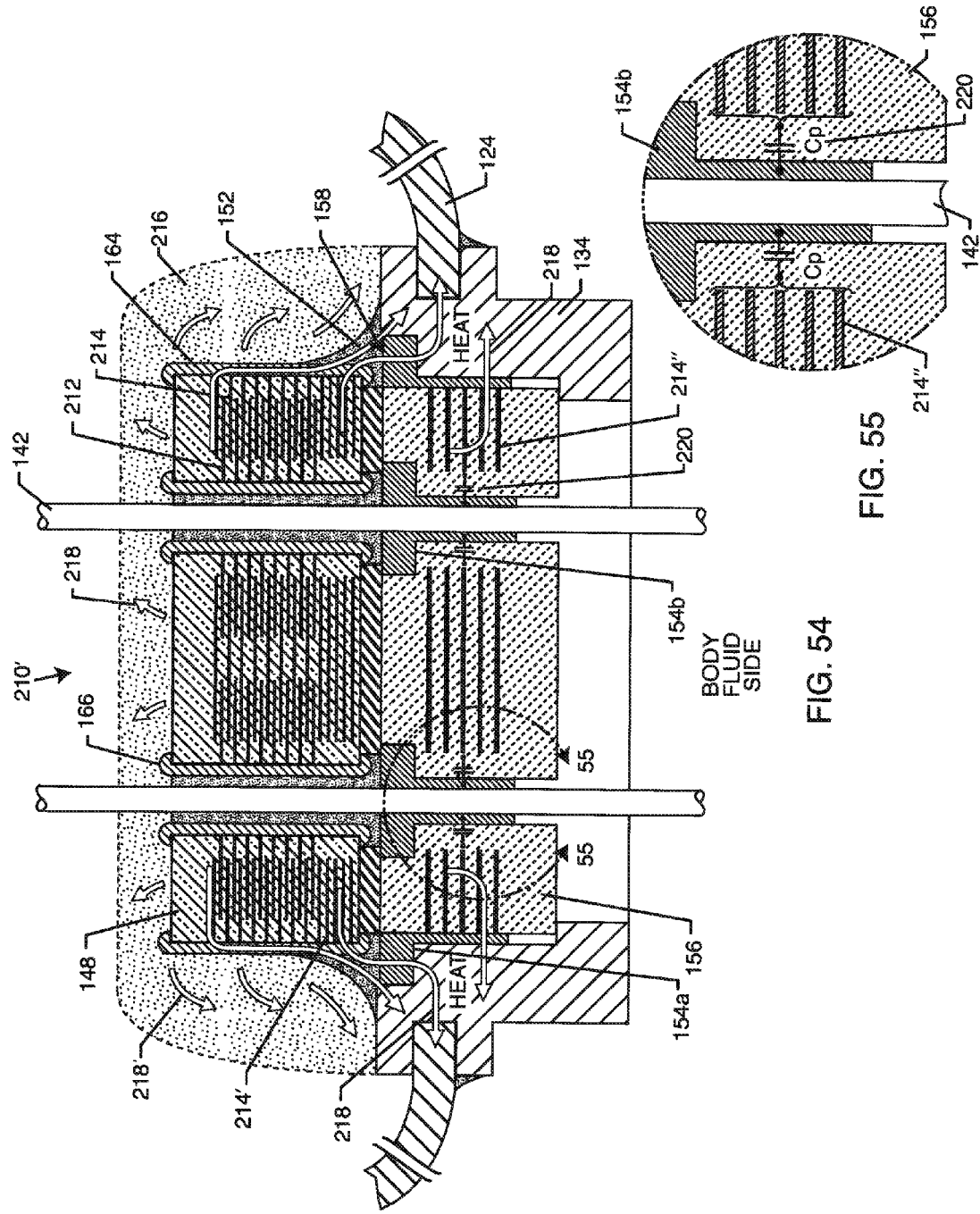

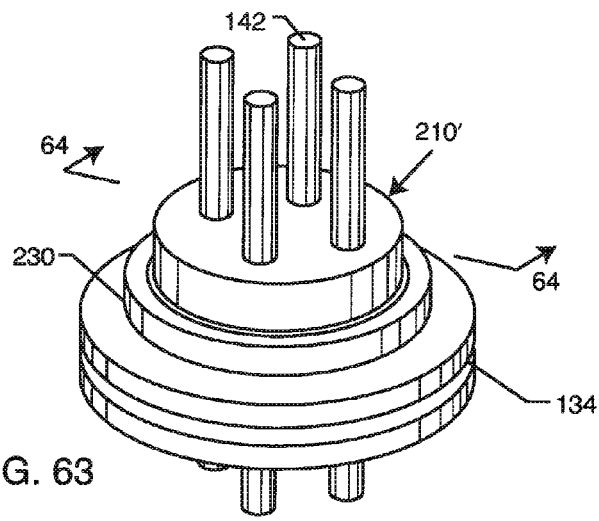
FIG. 63
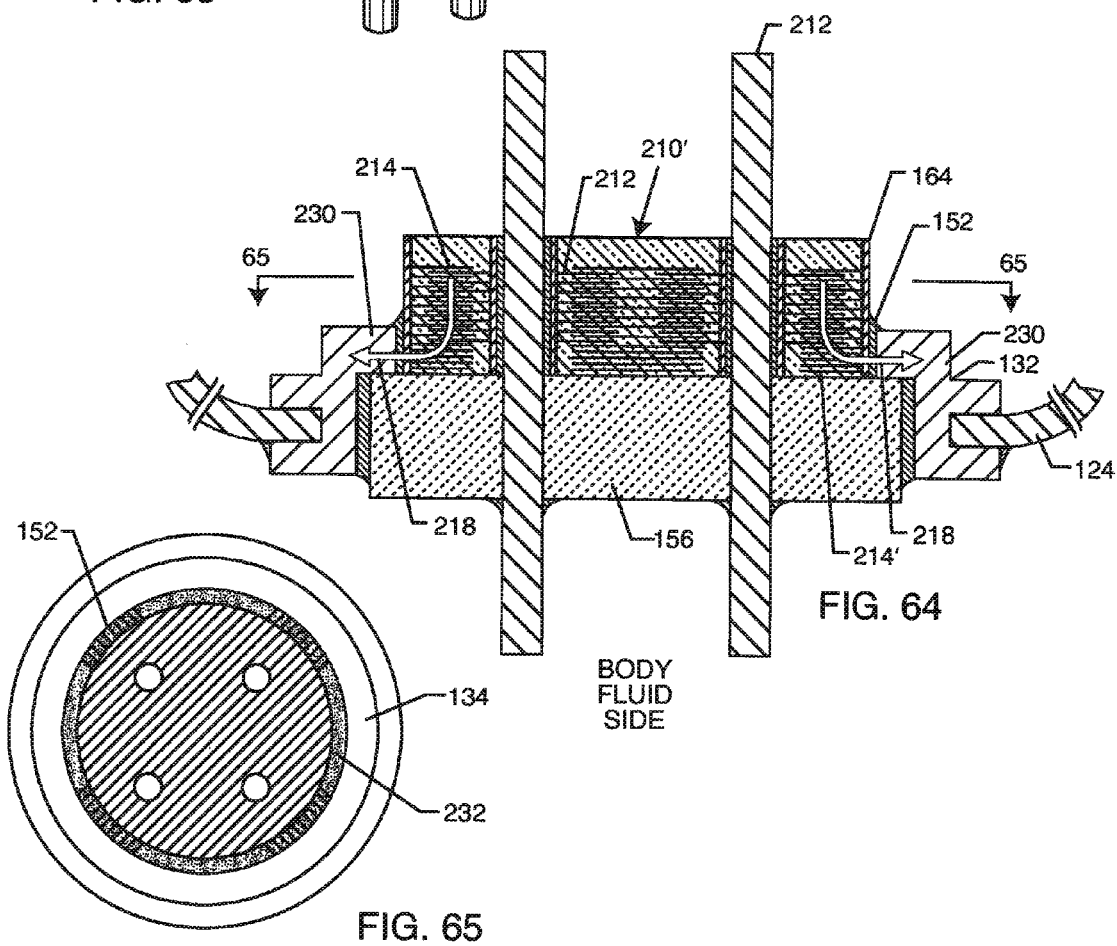
FIG. 64
FIG. 65

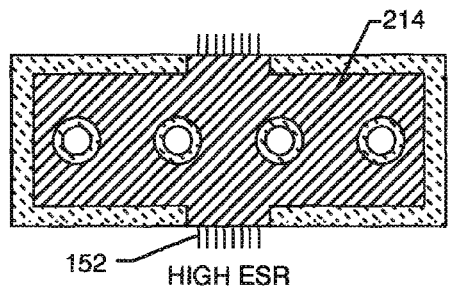
FIG. 75A — HIGH ESR
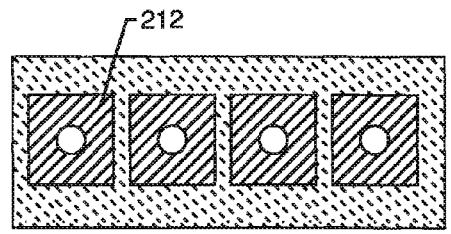
FIG. 75B
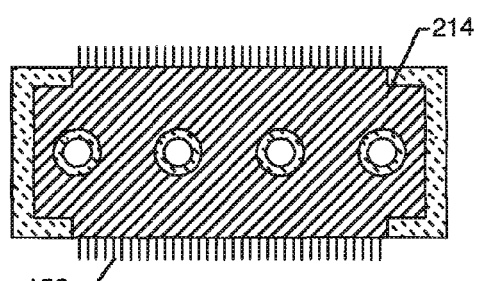
FIG. 76A — MEDIUM ESR
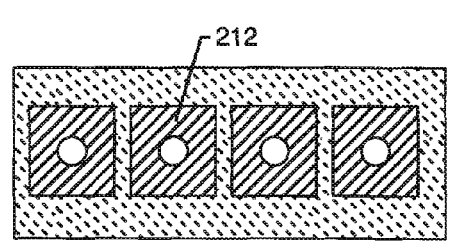
FIG. 76B
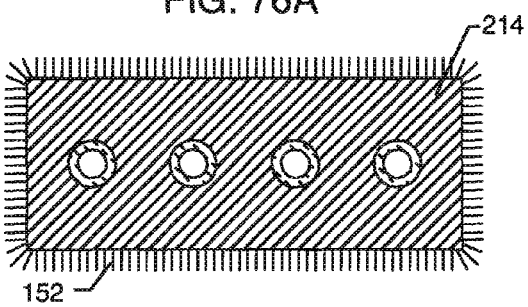
FIG. 77A — LOW ESR
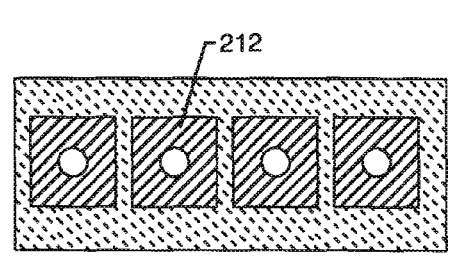
FIG. 77B
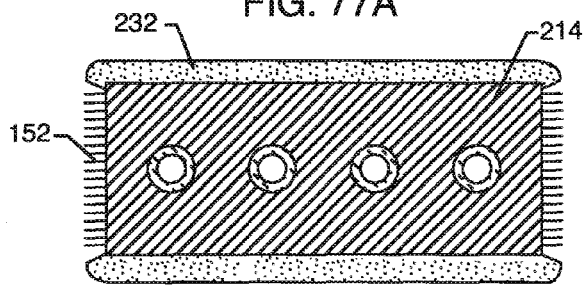
FIG. 78A — LOW ESR
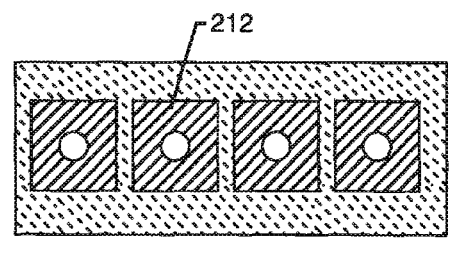
FIG. 78B

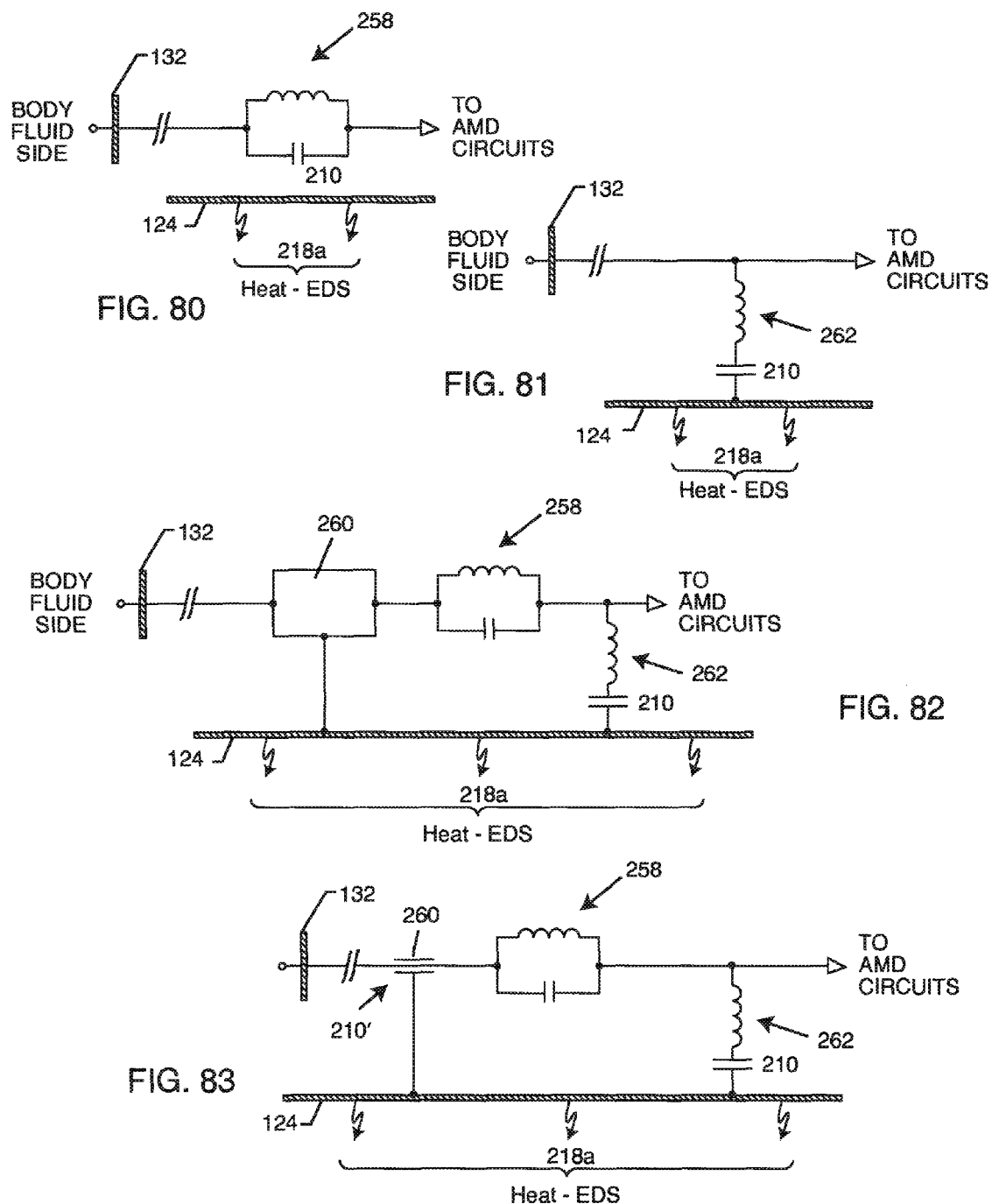

CAPACITOR FOR AN ACTIVE IMPLANTABLE MEDICAL DEVICE (AIMD) FOR HANDLING HIGH RF POWER INDUCED IN AN IMPLANTED LEAD FROM AN EXTERNAL RF FIELD

CROSS REFERENCE TO RELATED APPLICATIONS

This application is a continuation of U.S. patent application Ser. No. 13/408,020, filed on Feb. 29, 2012, now abandoned, which claims priority to U.S. provisional application Ser. No. 61/448,069, filed Mar. 1, 2011.

FIELD OF INVENTION

This invention generally relates to the problem of RF energy induced into implanted leads during medical diagnostic procedures such as magnetic resonant imaging (MRI), and provides methods and apparatus for redirecting RF energy to locations other than the distal tip electrode-to-tissue interface. In addition, the present invention provides electromagnetic interference (EMI) protection to sensitive active implantable medical device (AIMD) electronics.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one proceeds to the websites of the major cardiac pacemaker manufacturers in the United States, which include St. Jude Medical, Medtronic and Boston Scientific (formerly Guidant), one will see that the use of MRI is generally contra-indicated for patients with implanted pacemakers and cardioverter defibrillators. See also recent press announcements of the Medtronic Revo MRI pacemaker which was recently approved by the U.S. FDA. With certain technical limitations as to scan type and location, this is the first pacemaker designed for MRI scanning. See also:
(1) Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "1. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "Ill. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, Patent Application Publication US 2003/0050557, Susil and Halperin et al., published Mar. 13, 2003;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Pat. No. 7,844,534, Susil et al., issued Nov. 30, 2010.

The contents of the foregoing are all incorporated herein by reference.

However, an extensive review of the literature indicates that, despite being contra-indicated, MRI is indeed often used to image patients with pacemaker, neurostimulator and other active implantable medical devices (AIMDs). As such, the safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the International Society for Magnetic Resonance in Medicine (ISMRM), which was held on 5-6 Nov. 2005, it was reported that certain research systems are going up as high as 11.7 Tesla and will be ready sometime in 2010. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components; (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of about 21 MHz to about 500 MHz depending upon the static magnetic field strength. The frequency of the RF pulse for hydrogen scans varies by the Lamour equation with the field strength of the main static field where: RF PULSED FREQUENCY in MHz=(42.56) (STATIC FIELD STRENGTH IN TESLA). There are also phosphorous and other types of scanners wherein the Lamour equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 2-5 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the leadwire system (for example, at the header block of a cardiac pacemaker). This has to do with the wavelength of the signals involved and where they couple efficiently into the system.

Magnetic field coupling into an implanted lead system is based on loop areas. For example, in a cardiac pacemaker unipolar lead, there is a loop formed by the lead as it comes from the cardiac pacemaker housing to its distal tip electrode, for example, located in the right ventricle. The return path is through body fluid and tissue generally straight from the tip electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal pacemaker implant, the implanted loop area is much larger (around 400 square centimeters).

Relating now to the specific case of MRI, the magnetic gradient fields would be induced through enclosed loop areas. However, the pulsed RF fields, which are generated by the body coil, would be primarily induced into the lead system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur. Also, distal tip design is very important as it can heat up due to MRI RF induced energy.

The cause of heating in an MRI environment is twofold: (a) RF field coupling to the lead can occur which induces significant local heating; and (b) currents induced between the distal tip and tissue during MRI RF pulse transmission sequences can cause local Ohms Law (resistive) heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD lead geometries. There can also be localized heating problems associated with various types of electrodes in addition to tip electrodes. This includes ring electrodes or pad electrodes. Ring electrodes are commonly used with a wide variety of implanted devices including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves.

Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker lead length and implant trajectory can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the function of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar and the like. It is very important that excessive current not flow at the interface between the lead distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. Excessive current at the distal electrode to tissue interface can cause excessive heating to the point where tissue ablation or even perforation can occur. This can be life threatening for cardiac patients. For neurostimulator patients, such as deep brain stimulator patients, thermal injury can cause coma, permanent disability or even be life threatening. Similar issues exist for spinal cord stimulator patients, cochlear implant patients and the like.

Interestingly, the inventors performed an experiment in an MRI scanner with a human body gel-filled phantom. In the phantom, placed in an anatomic position, was an operating pacemaker and a lead. This was during evaluation of the efficacy of bandstop filters at or near the distal tip electrode for preventing the distal tip electrode from overheating. Bandstop filters for this purpose are more thoroughly described in U.S. Pat. No. 7,363,090, the contents of which are incorporated herein by reference. During the experiments, there was a control lead that had no bandstop filter. During a particularly RF intense scanning sequence, Luxtron probes measured a distal helix tip electrode temperature rise of 30 degrees C. Of course, the 30 degrees C. temperature rise in a patient, would be very alarming as it could lead to pacing capture threshold changes or even complete loss capture due to scar tissue formation. An identical lead with the bandstop filter in place only had a temperature rise of 3 degrees C. This was a remarkable validation of the efficacy of bandstop filters for implantable electrodes. However, something very interesting happened when we disconnected the pacemaker. We disconnected the pacemaker and put a silicone lead cap over the proximal end of the lead. Again, we put the gel phantom back inside the MR scanner and this time we measured an 11 degree C. temperature rise on the lead with the bandstop filter. This was proof positive that the housing of the AIMD acts as part of the system. The prior art feedthrough capacitor created a fairly low impedance at the input to the pacemaker and thereby drew RF energy out of the lead and diverted it to the housing of the pacemaker. It has recently been discovered that the impedance, and in particular, the ESR of these capacitors, is very important so that maximal energy can be pulled from the lead and diverted to the pacemaker housing while at the same time, not unduly overheating the feedthrough capacitor.

Accordingly, there is a need for novel low ESR diverting capacitors and circuits which are frequency selective and are constructed of passive components for implantable leads and/or leadwires. Further, there is a need for very low ESR diverter element capacitor(s) which are designed to decouple a maximum amount of induced RF energy from an implanted lead to an AIMD housing while at the same time not overheat. The present invention fulfills these needs and provides other related advantages.

SUMMARY OF THE INVENTION

The present invention relates to an RF filter for an active medical device (AMD) for handling high RF power induced in an associated lead from an external RF field at a selected MRI frequency or range of frequencies. In a preferred embodiment, the RF filter comprises a capacitor having a capacitance generally between about 10 to about 20,000 picofarads, and a temperature stable dielectric having a dielectric constant of about 200 or less. In addition, the dielectric material should have a temperature coefficient of capacitance (TCC) within the range of plus 400 to minus 7112 parts per million per degree centigrade (ppm/° C.). Furthermore, the capacitor's dielectric loss tangent in ohms should be less than about five percent of the capacitor's equivalent series resistance (ESR) at the selected MRI frequency or range of frequencies.

In a second embodiment, the AIMD diverter capacitor 140 comprises at least ten interleaved active and ground electrode plates designed to minimize the capacitor's high frequency ESR while maximizing internally generated heat flow from the capacitor. The ground electrode plates are conductively connected to an energy dissipating surface (EDS). In preferred embodiments of the invention, the EDS surface comprises a housing of the AMD and/or a ferrule conductively attached to both the ground electrode plates and the housing for the AMD.

Preferably, the capacitor's ESR at MRI RF pulsed frequencies should be less than about two ohms, more preferably, about less than 0.5, and most preferably, less than about 0.1 ohm. The capacitance should vary no more than plus or minus about one percent over the temperature range of about minus 55 degrees C. to about plus 125 degrees C. Moreover, the capacitor's dielectric loss tangent should be less than about two ohms at the selected MRI RF frequency or range of frequencies.

Each dielectric layer may comprise multiple electrode plates.

The AIMD diverter capacitor may comprise a monolithic ceramic capacitor, a flat-through capacitor, a chip capacitor, an X2Y attenuator, or a feedthrough capacitor.

In several embodiments, the interleaved electrode plates are bounded at one end by a first set of at least one extra ground plate embedded within the dielectric material. In other embodiments, a second set of at least one ground plate is embedded within the dielectric material and bounds the interleaved electrode plates opposite the first set of ground plates.

The plurality of ground electrode plates may extend substantially to the periphery of the capacitor. A high thermal conductivity material may also be utilized for attaching the ground electrode plates to a heat sink. The heat sink may comprise a conductive ferrule or a heat conductive structure affixed to the periphery of the capacitor. The conductive structure may comprise a plurality of convection fins.

In a further embodiment, the AIMD diverter capacitor 140 may comprise an element of a lowpass filter which can be combined with inductors to form either an L filter, a reverse L filter, an LL, a reverse LL, a T, a Pi or an n-element lowpass filter.

The lowpass filters, which can consist in the simplest embodiment of just a diverter capacitor, can also be combined within the AIMD with bandstop filters and L-C trap filters.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is a diagram of a unipolar active implantable medical device;

FIG. 7 is a diagram similar to FIG. 6, illustrating a bipolar AIMD system;

FIG. 8 is a diagram similar to FIGS. 6 and 7, illustrating a bipolar lead system with a distal tip and ring electrodes, typically used in a cardiac pacemaker;

FIG. 27 illustrates a cross-sectional view of an MLCC capacitor mounted to separate circuit traces;

FIG. 28 is a schematic representation explaining the elements that are components of the FIG. 27 capacitor's equivalent series resistance (ESR);

FIG. 29 is an equation that relates the capacitance with the capacitor's active area, dielectric constant, number of electrode plates and dielectric thickness;

FIG. 36 illustrates the reactance and real losses of a 2000 picofarad X7R feedthrough capacitor;

FIG. 37 illustrates the reactance and real losses of a 2000 picofarad COG (NPO) capacitor;

FIG. 54 is very similar to the capacitor of FIG. 50 except that thermally-conductive ground plates have been added to the hermetic insulator to provide an additional conductive heat path;

FIG. 55 illustrates that a parasitic capacitance has been formed in the alumina insulator which enhances high frequency filter performance;

FIG. 63 illustrates a round quad polar capacitor similar to FIG. 15;

FIG. 64 is a sectional view taken from section 64-64 from FIG. 63;

FIG. 65 is a top sectional view taken from section 65-65 from FIG. 64 showing that the capacitor electrical connection is interposed between areas of high thermal conductivity material;

FIGS. 75A and 75B illustrate relatively high ESR electrode plate arrangements;

FIGS. 76A and 76B illustrate a medium ESR electrode arrangement;

FIGS. 77A and 77B illustrate a very low ESR electrode arrangement;

FIGS. 78A and 78B illustrate a composite low ESR and highly thermally-conductive electrode attachment;

FIG. 80 illustrates that a bandstop filter can be combined with any of the lowpass filters of FIG. 79;

FIG. 81 illustrates that an L-C trap filter may also be added in combination with any of the circuits of FIG. 79 or 80;

FIG. 82 illustrates a general lowpass filter, a bandstop filter and an L-C trap;

FIG. 83 illustrates a feedthrough diverter capacitor, a bandstop filter and an L-C trap.

DETAILED DESCRIPTION OF THE PREFERRED EMBODIMENTS

Figure 1:
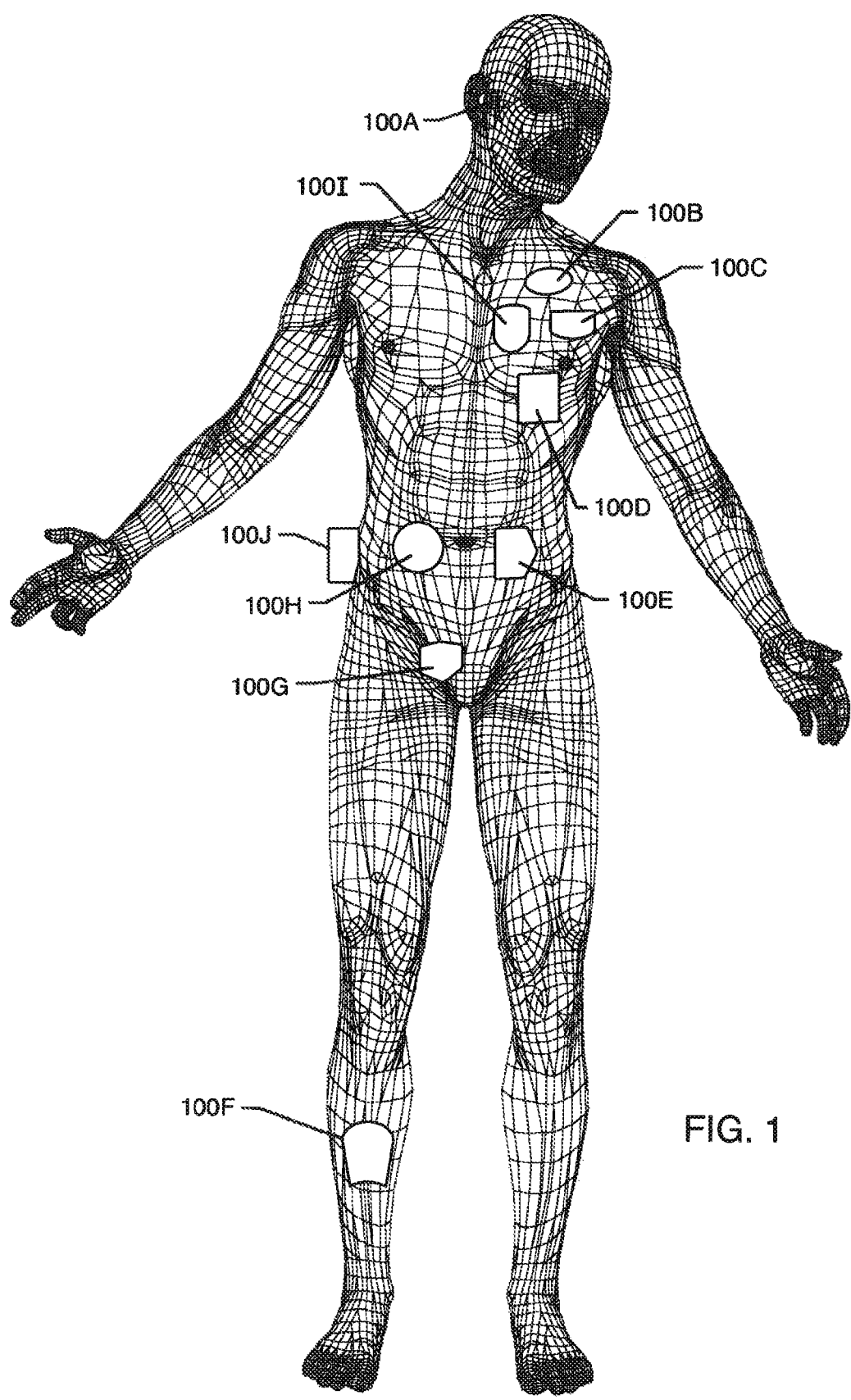
FIG. 1 is a wire-formed diagram of a generic human body showing a number of exemplary implanted medical devices.

FIG. 1 illustrates various types of active implantable medical devices referred to generally by the reference numeral 100 that are currently in use. FIG. 1 is a wire formed diagram of a generic human body showing a number of exemplary implanted medical devices. Numerical designation 100A is a family of implantable hearing devices which can include the group of cochlear implants, piezoelectric sound bridge transducers and the like. Numerical designation 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. Numerical designation 100C shows a cardiac pacemaker which is well-known in the art. Numerical designation 100D includes the family of left ventricular assist devices (LVAD's), and artificial hearts, including the recently introduced artificial heart known as the Abiocor. Numerical designation 100E includes an entire family of drug pumps which can be used for dispensing of insulin, chemotherapy drugs, pain medications and the like. Insulin pumps are evolving from passive devices to ones that have sensors and closed loop systems. That is real time monitoring of blood sugar levels will occur. These devices tend to be more sensitive to EMI than passive pumps that have no sense circuitry or externally implanted leadwires, 100F includes a variety of implantable bone growth stimulators for rapid healing of fractures. Numerical designation 100G includes urinary incontinence devices. Numerical designation 100H includes the family of pain relief spinal cord stimulators and anti-tremor stimulators. Numerical designation 100H also includes an entire family of other types of neurostimulators used to block pain. Numerical designation 100I includes a family of implantable cardioverter defibrillator (ICD) devices and also includes the family of congestive heart failure devices (CHF). This is also known in the art as cardio resynchronization therapy devices, otherwise known as CRT devices. Numerical designation 100J illustrates an externally worn pack. This pack could be an external insulin pump, an external drug pump, an external neurostimulator or even a ventricular assist device.

Referring to U.S. 2003/0050557, Paragraphs 79 through 82, the contents of which are incorporated herein, metallic structures, particularly leads, are described that when placed in MRI scanners, can pick up high electrical fields which results in local tissue heating. This heating tends to be most concentrated at the ends of the electrical structure (either at the proximal or distal lead ends). This safety issue can be addressed using the disclosed systems and methods of the present invention. A significant concern is that the distal electrodes, which are in contact with body tissue, can cause local tissue burns.

As used herein, the lead means an implanted lead, including its conductors and electrodes that have electrodes that are in contact with body tissue. In general, for an AIMD, the term lead means the lead that is outside of the AIMD housing and is implanted or directed into body tissues. The term leadwire as used herein refers to the wiring or circuit traces that are generally inside of the active implantable medical device (AIMD) and are not exposed directly to body fluids.

Figure 2:
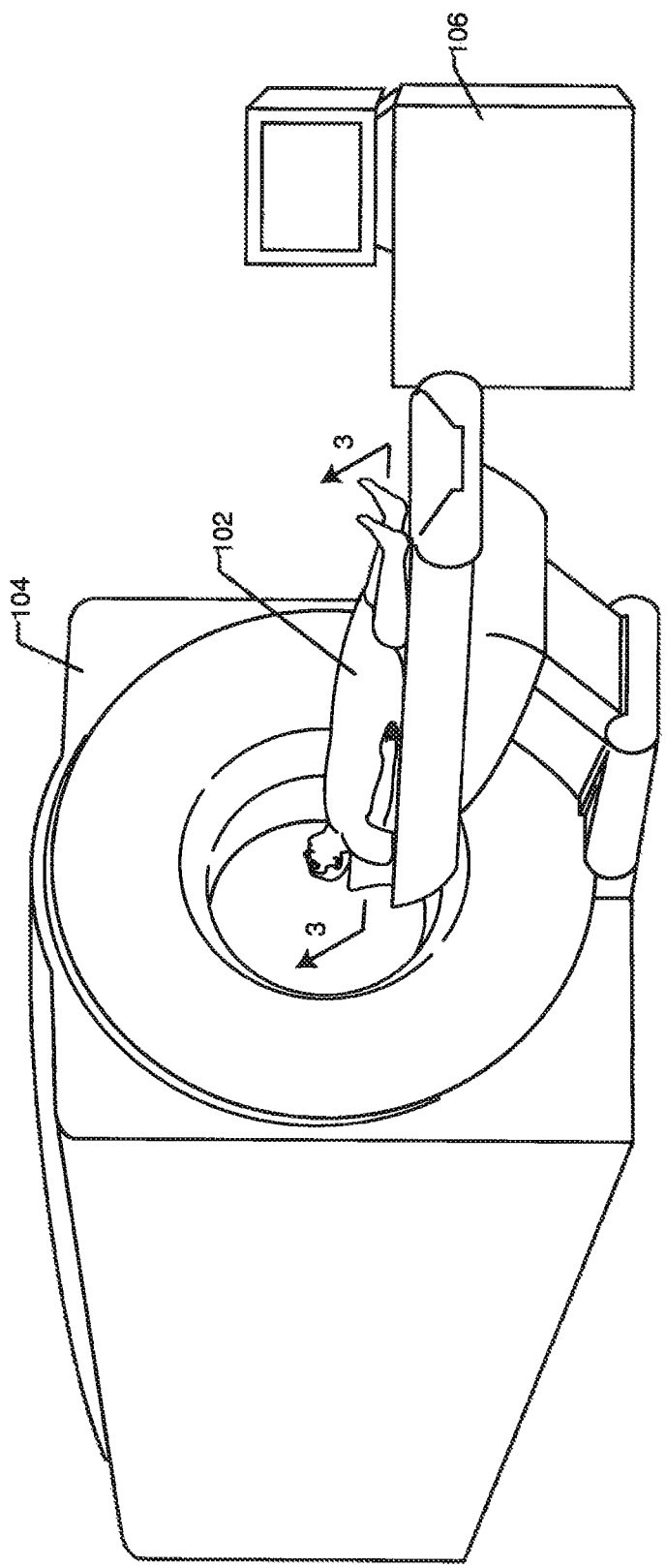
FIG. 2 is a pictorial view of an AIMD patient who is about to be placed into an MRI scanner.

FIG. 2 illustrates an AIMD patient 102 about to be conveyored into an MRI machine 104. Imaging processing equipment is shown as 106.

Figure 3:
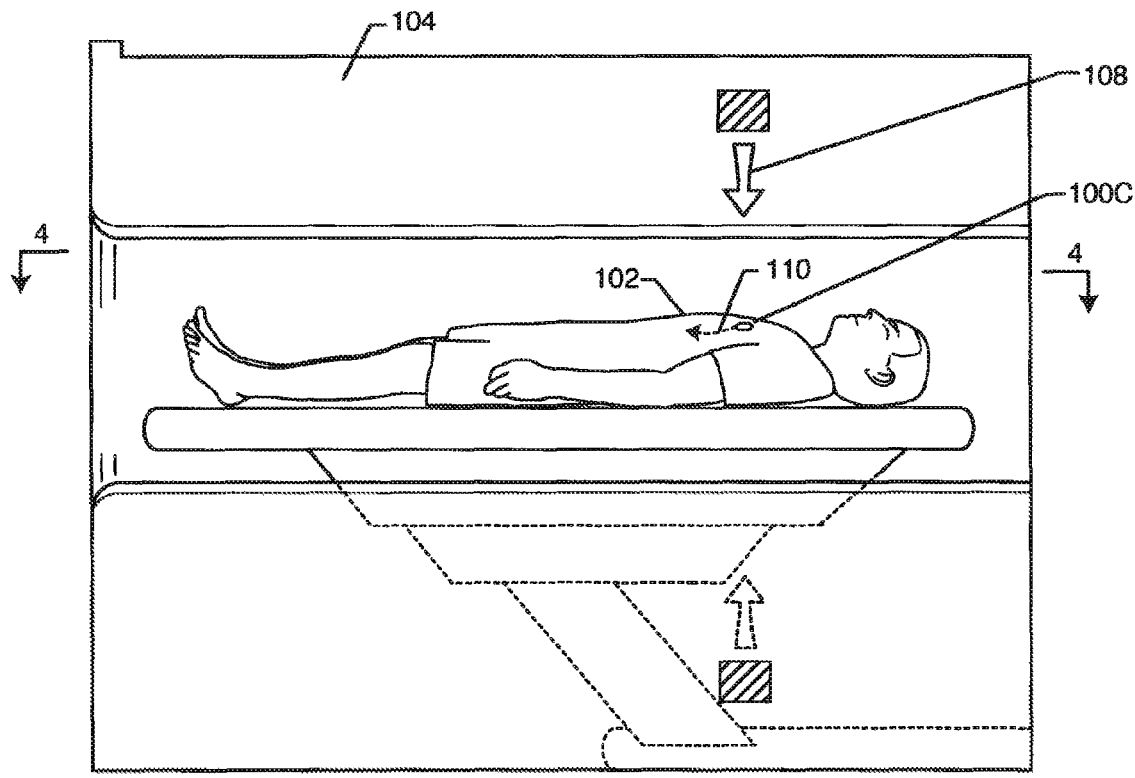
FIG. 3 shows a side view of the patient within the scanner showing an intense RF field impinging on the implanted medical device and its associated lead.

FIG. 3 is a side view showing the patient 102 within the MRI scanner bore 104. Intense RF field 108 is generated by the scanners bird cage coil. As can be seen, this RF field is impinging on both the implanted cardiac pacemaker 100C and its associated leads 110.

Figure 4:
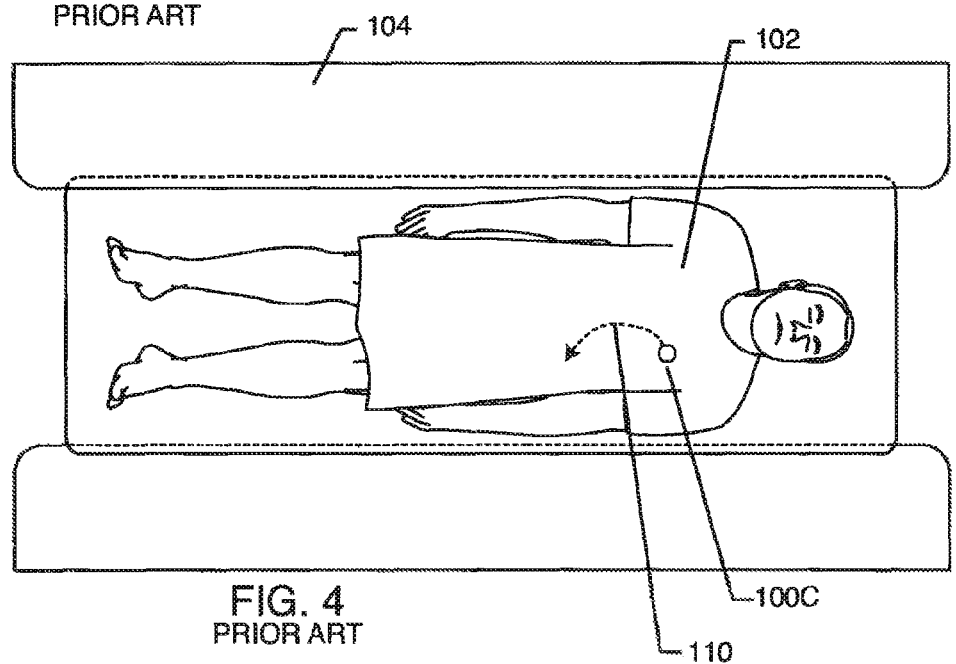
FIG. 4 is a top view of the patient in the MRI scanner showing one location of the AIMD and its associated lead.

FIG. 4 is a top view of the patient 102 inside the MRI scanner bore 104. As can be seen, the pacemaker 100C is in a left pectoral pocket with the leads 110 routed transvenously down into the interior chambers of the heart.

Figure 5:
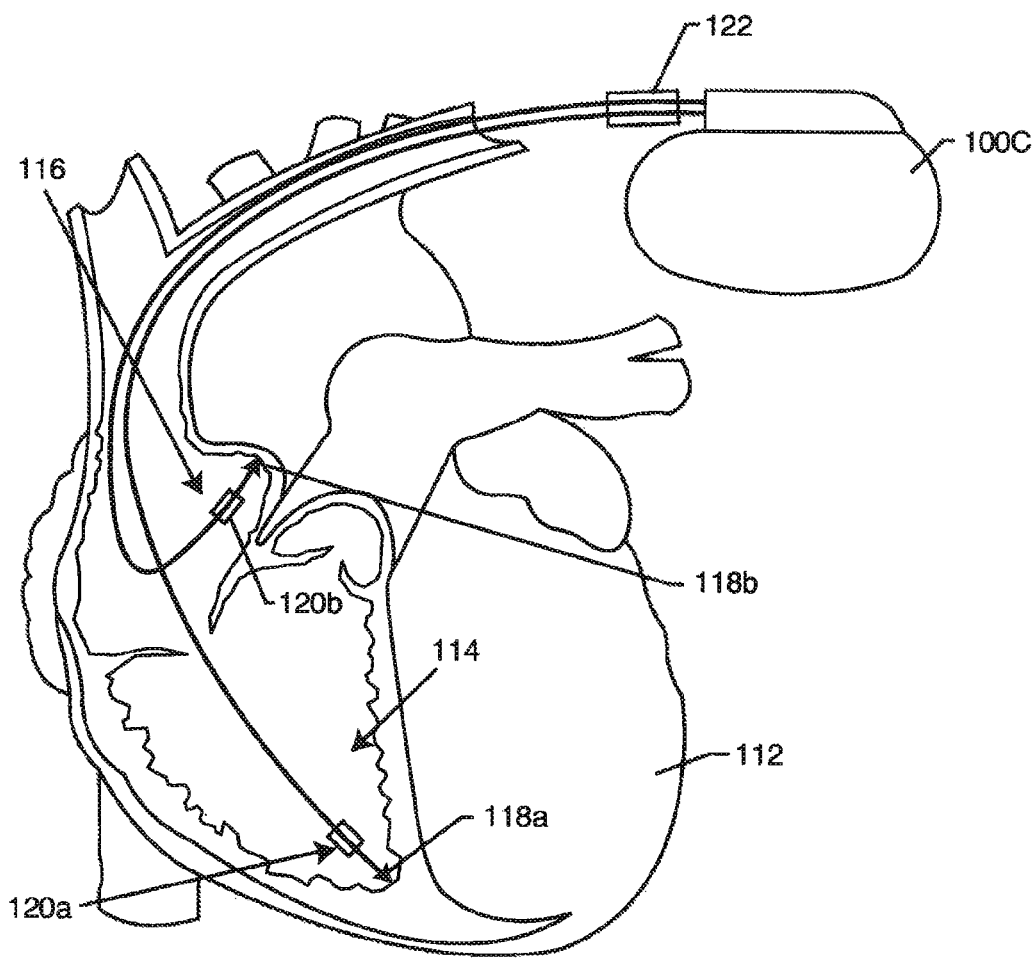
FIG. 5 is a line drawing of a human heart with cardiac pacemaker dual chamber bipolar leads shown in the right ventricle and the right atrium.

FIG. 5 is a line drawing of a human heart 112 with cardiac pacemaker 100C dual chamber bipolar leads shown in the right ventricle 114 and the right atrium 116 of a human heart 112.

Referring once again to FIG. 5, as previously mentioned, it is very important that this lead system does not overheat during MRI procedures particularly at or near the distal tip 118*a*, 118*b* electrodes and ring electrodes 120*a*, 120*b*. If either or both the distal tip 118*a*, 118*b* and ring 120*a*, 120*b* electrode become overgrown by body tissue, excessive overheating can cause scarring, burning or necrosis of said tissues. This can result in loss of capture (loss pacing pulses) which can be life-threatening for a pacemaker dependent patient. It is also the case where implanted leads are often abandoned (where the lead has been permanently disconnected from the AIMD). Often times when the device such as a pacemaker 100C shown in FIG. 5 is changed out, for example, due to low battery life and a new pacemaker is installed, the physician may decide to install new leads at the same time. Leads are also abandoned for other reasons, such as a dislodged or a high impedance threshold or high leakage current. Sometimes over the course of a patient life-time, the distal tip electrode to tissue interface increases in impedance. This means that the new pacemaker would have to pulse at a very high voltage output level which would quickly deplete its battery life. This is yet another example of why a physician would choose to insert new leads. Sometimes the old leads are simply extracted. However, this is a very complicated surgical procedure which does involve risks to the patient. Fortunately, there is usually plenty of room in the venous system and in the tricuspid valve to place additional leads through the same pathway. The physician may also choose to implant the pacemaker on the other side. For example, if the original pacemaker was in the right pectoral region, the physician may remove that pacemaker and choose to install the new pacemaker in the left pectoral region using a different part of the venous system to gain lead access. In either case, the abandoned leads can be very problematic during an MRI procedure. In general, prior art abandoned leads are capped with a silicone cap at their proximal connector points so that body fluids will not enter into the lead system, cause infections and the like. However, it has been shown in the literature that the distal electrodes 118, 120 of abandoned leads are at high risk to heat up during MRI procedures. Accordingly, a passive frequency selective circuit of the present invention is very useful when placed at or near the proximal electrical contact after a pacemaker is removed and its leads are disconnected (abandoned). For example, for an abandoned (left in the body) lead, an energy dissipating surface 122 at or near the proximal lead end is an ideal place to eliminate excess energy induced by MRI in the leadwire system. The energy dissipating surface 122 may incorporate a high RF power diverter capacitor 140 of the present invention. Referring once again to FIG. 5, one can see that there is a distal tip electrode 118 and a ring electrode 120 placed in the right ventricle 114 and a distal tip electrode 118 and distal ring electrode 120 placed in the right atrium 116. Those skilled in the art will realize that many different lead configurations are possible for the human heart and also other neurostimulator applications.

FIG. 6 is a general diagram of a unipolar active implantable medical device 100 and related lead system. The housing 124 of the active implantable medical device 100 is typically titanium, ceramic, stainless steel or the like. Inside of the device housing 124 are the AIMD electronic circuits. Usually AIMDs include a battery, but that is not always the case. A leadwire or lead 110 is routed from the AIMD 100 to a distal electrode 118, 120 typically including or comprising an electrode embedded in, affixed to, or in contact with body tissue. In the case of a spinal cord stimulator 100H (FIG. 1), the distal electrode 118, 120 could be in the spinal cord. In the case of a deep brain stimulator 100B (FIG. 1), the distal electrode 118, 120 would be placed deep into the brain, etc. In the case of a cardiac pacemaker 100C (FIG. 1), the distal electrode 118, 120 would typically be placed in or outside of a cardiac chamber. The unipolar electrical return path is between the distal electrode through body tissue to the conductive housing 124 of the implantable unipolar medical device 100.

FIG. 7 is very similar to FIG. 6 except that it depicts a bipolar AIMD 100 and related lead system. In this case, a first lead conductor 110a is coupled to a first distal electrode 118, and a second distal electrode 120 and associated lead conductor 110b provide an electric circuit return path between the two distal electrodes 118 and 120. In the case where the AIMD 100 is a cardiac pacemaker 100C, this would be known as a bipolar lead system with one of the electrodes known as the distal tip electrode 118 and the other electrode (which would float in the blood pool) known as the ring electrode 120.

In all of these applications, the patient could be exposed to the fields of an MRI scanner or other powerful emitter used during a medical diagnostic procedure, currents that are directly induced in the leads 110a, 110b can cause heating by $P=I^2R$ (Ohm's law) losses in the leads or by heating caused by RF current flowing from the tip and ring electrodes 118, 120 into body tissue. If these induced RF currents become excessive, the associated heating can cause damage or even destructive ablation to body tissue. These induced currents and voltages in an implanted lead can also cause EMI problems to the AIMD. AIMD EMI can include oversensing, device re-set, mode-switching, pacing inhibition or inappropriate therapy delivery.

In FIG. 8, the AIMD 100 is a cardiac pacemaker 100C wherein the distal tip electrode 118 is designed to be implanted against or into or affixed (screwed into) to the myocardial tissue of the heart 112. The ring electrode 120 is designed to float in the blood pool within a cardiac ventricle.

Figure 9:
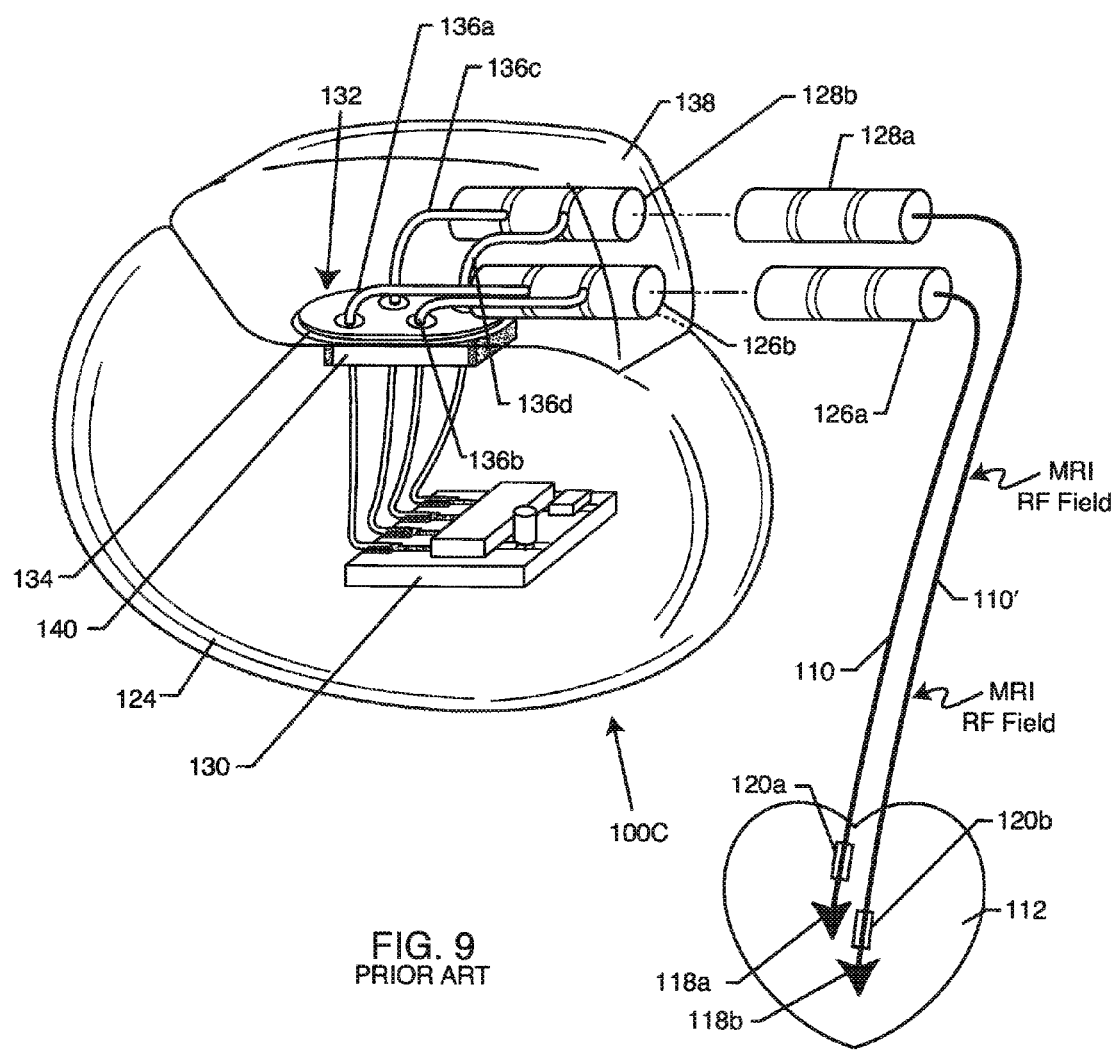
FIG. 9 illustrates a dual chamber cardiac pacemaker with its associated leads and electrodes implanted into a human heart.
Figure 10:
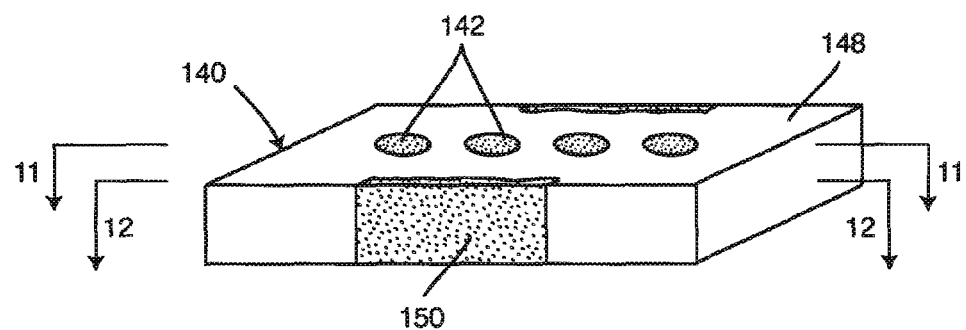
FIG. 10 is a perspective view of a rectangular broadband or lowpass EMI filter capacitor.

FIG. 9 is a pectoral view of a prior art cardiac pacemaker 100C showing dual chamber bipolar leads 116, 110' routed to distal tip electrodes 118a and 118b and distal ring electrode 120a and 120b. As can be seen, the leads 110, 110' are exposed to a powerful RF-pulsed field from an MRI machine. This induces electromagnetic energy on the leads which are coupled via ISO Standard IS-1 or DF-1 connectors 126, 128 through header block 138 which connects the leads to electronic circuits 130 inside of the hermetically sealed pacemaker housing 124. A hermetic seal assembly 132 is shown with a metal ferrule 134 which is generally laser welded into the titanium housing 124 of the cardiac pacemaker 100C, Lead wires 136a through 136d penetrate the ferrule 134 of the hermetic seal in non-conductive relation. Glass seals or gold brazes are formed to perfect the hermetic seal which keeps body fluids from getting to the inside of the pacemaker housing 124.

FIGS. 10-14 illustrate a prior art rectangular bipolar feedthrough capacitor (planar array) 140 mounted to the hermetic terminal 132 of a cardiac pacemaker in accordance with U.S. Pat. No. 5,333,095 to Stevenson et al. the contents of which are incorporated herein. As illustrated in FIGS. 10-14, in a typical broadband or lowpass EMI filter construction, a ceramic feedthrough filter capacitor, 140 is used in a hermetic feedthrough assembly 132 to suppress and decouple undesired interference or noise transmission along one or more terminal pins 142, and may comprise a capacitor having two sets of electrode plates 144 and 146 embedded in spaced relation within an insulative dielectric substrate or base 148, formed typically as a ceramic monolithic structure. One set of the electrode plates 144 is electrically connected at an inner diameter cylindrical surface of the capacitor structure 140 to the conductive terminal pins 142 utilized to pass the desired electrical signal or signals (see FIG. 11). The other or second set of electrode plates 146 is coupled at a sidewall of the dielectric providing an outer edge surface of the capacitor 140 through metallization to a rectangular ferrule 134 of conductive material. In the prior art, without regard to high frequency capacitor ESR, the number and dielectric thickness spacing of the electrode plate sets 144, 146 varies in accordance with the capacitance value and the voltage rating of the capacitor 140.

In operation, the coaxial capacitor 140 permits passage of relatively low frequency electrical signals along the terminal pins 142, while shielding and decoupling/attenuating undesired interference signals of typically high frequency to the conductive housing 124. Feedthrough capacitors 140 of this general type are available in unipolar (one), bipolar (two), tripolar (three), quadpolar (four), pentapolar (five), hexpolar (6) and additional lead configurations. Feedthrough capacitors 140 (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the hermetic terminal pin assembly which is in turn electrically coupled to the coaxial feedthrough filter capacitor. As a result, the filter capacitor and terminal pin assembly prevent entrance of interference signals to the interior of the pacemaker housing 124, wherein such interference signals could otherwise adversely affect the desired cardiac pacing or defibrillation function.

Figure 11:
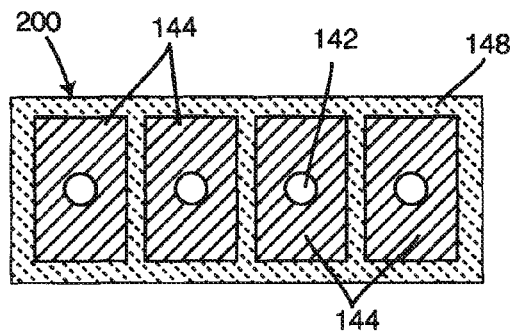
FIG. 11 is a horizontal section taken generally along the line 11-11 of FIG. 10, illustrating the configuration of active electrode plates within the rectangular capacitor.

FIG. 11 illustrates the configuration of active electrode plates 144 within the rectangular capacitor 140.

Figure 12:
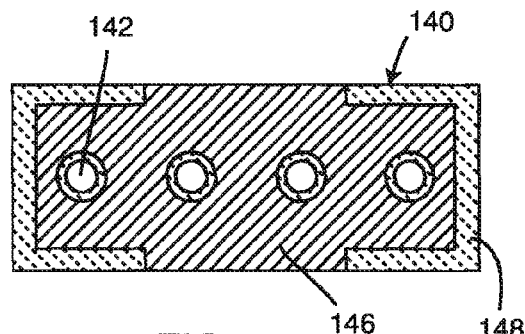
FIG. 12 is a horizontal section taken generally along the line's 12-12 of FIG. 10, illustrating the configuration of a set of ground electrode plates within the rectangular capacitor.

FIG. 12 illustrates the configuration of a set of ground electrode plates 146 within the rectangular capacitor 140.

Figure 13:
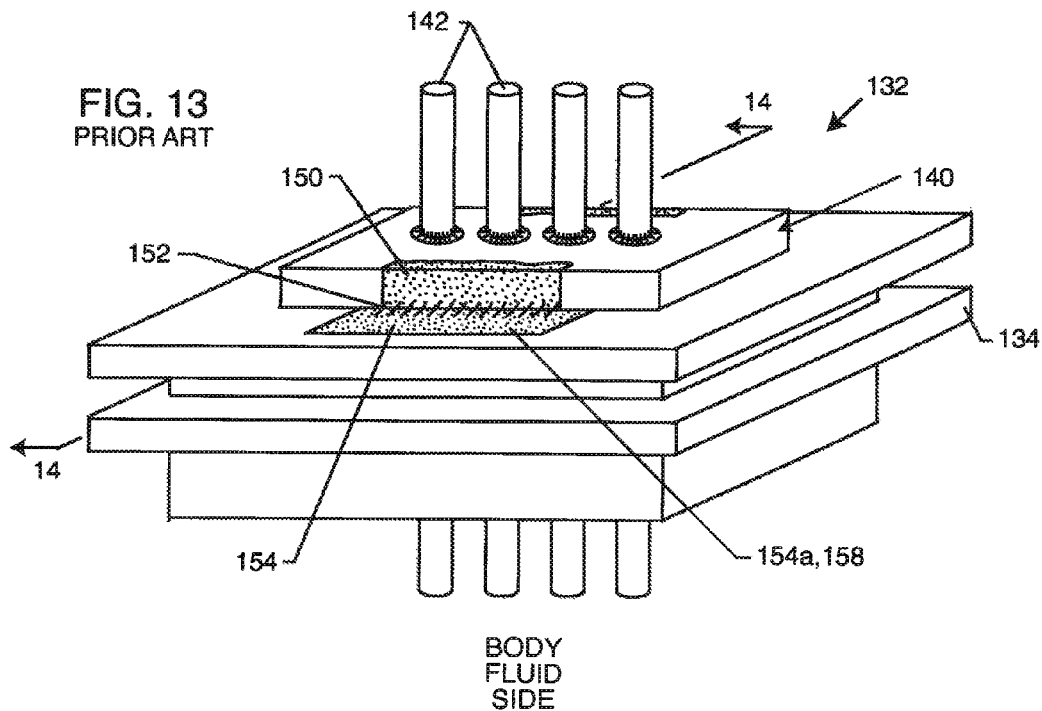
FIG. 13 is a perspective view illustrating the rectangular feedthrough capacitor of FIG. 10 mounted to a hermetic terminal.

FIG. 13 shows a quadpolar feedthrough capacitor 140 (which is identical to the capacitor of FIG. 10) mounted to the hermetic terminal 132. As one can see in FIG. 13, the conductive polyimide material 152 connects between the capacitor metallization 150 and the gold braze area 154. The gold braze 154 forms a metallurgical bond with the titanium and precludes any possibility of an unstable oxide forming. Gold is a noble metal that does not oxidize and remains very stable even at elevated temperatures. The novel construction methodology illustrated in FIG. 13 guarantees that the capacitor ohmic losses will remain very small at all frequencies. By connecting the capacitor's electrode plates to a low resistivity surface such as gold, one is guaranteed that this connection will not substantially contribute to the capacitor's overall ESR. Keeping the ESR as low as possible is very important for diverting a high amount of RF current such as that induced in the lead system by MRI scanners. One is referred to U.S. Pat. No. 6,765,779 to Stevenson et al., for additional information on electrically connecting to non-oxidized surfaces, the contents of which are incorporated herein by reference.

Figure 14:
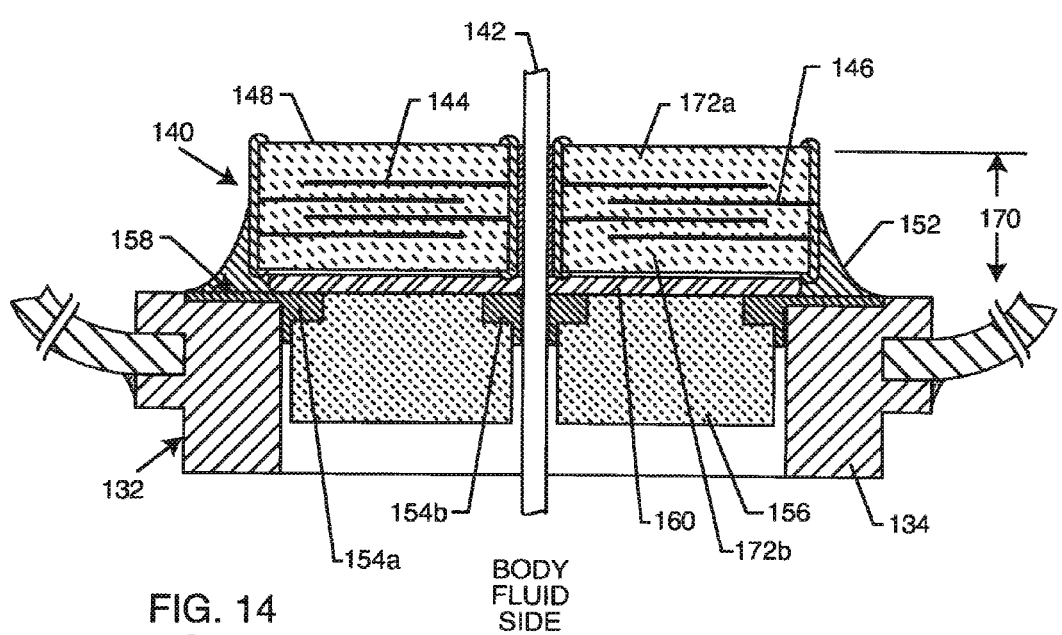
FIG. 14 is an enlarged sectional view taken generally along the line 14-14 of FIG. 13.

FIG. 14 is a cross-section of the capacitor shown in FIG. 13. One can see that the gold braze (or weld) areas 154a and 154b that form the hermetic seal between the alumina insulator 156 and the titanium ferrule 134 are desirably on the feedthrough capacitor side. This makes it easy to manufacture the gold bond pad area 158 for convenient attachment of the conductive thermal-setting material 152. In other words, by having the gold braze hermetic seals 154 on the same side as the gold bond pad area 158, these can be co-formed in one manufacturing operation in a gold braze vacuum furnace.

Further, a unique insulative material 160 is disposed between the capacitor 140 and the underlying hermetic terminal 132.

Figure 15:
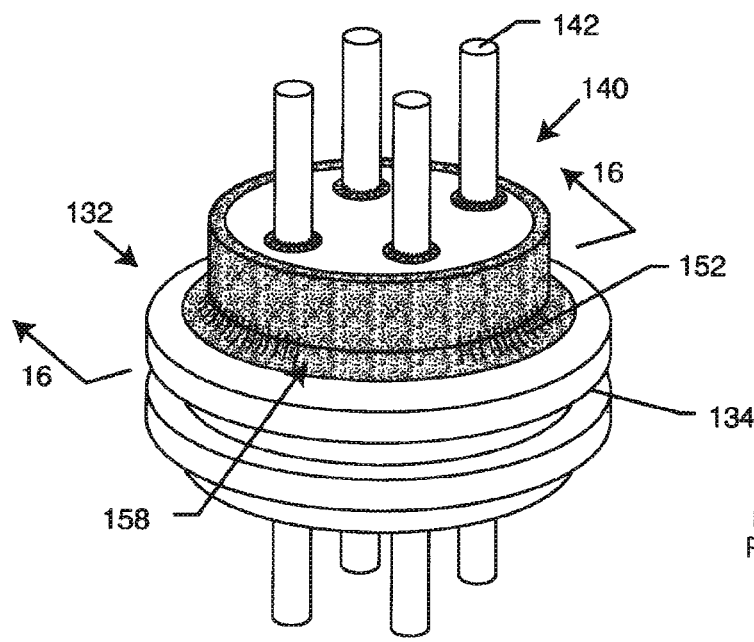
FIG. 15 is a perspective view of a round hermetic terminal showing a quadpolar RF diverter feedthrough capacitor.

FIG. 15 is a quad polar feedthrough capacitor 140 mounted to a hermetic terminal 132 similar to that described in FIG. 13 except that in this case, the structure is round or discoidal.

Figure 16:
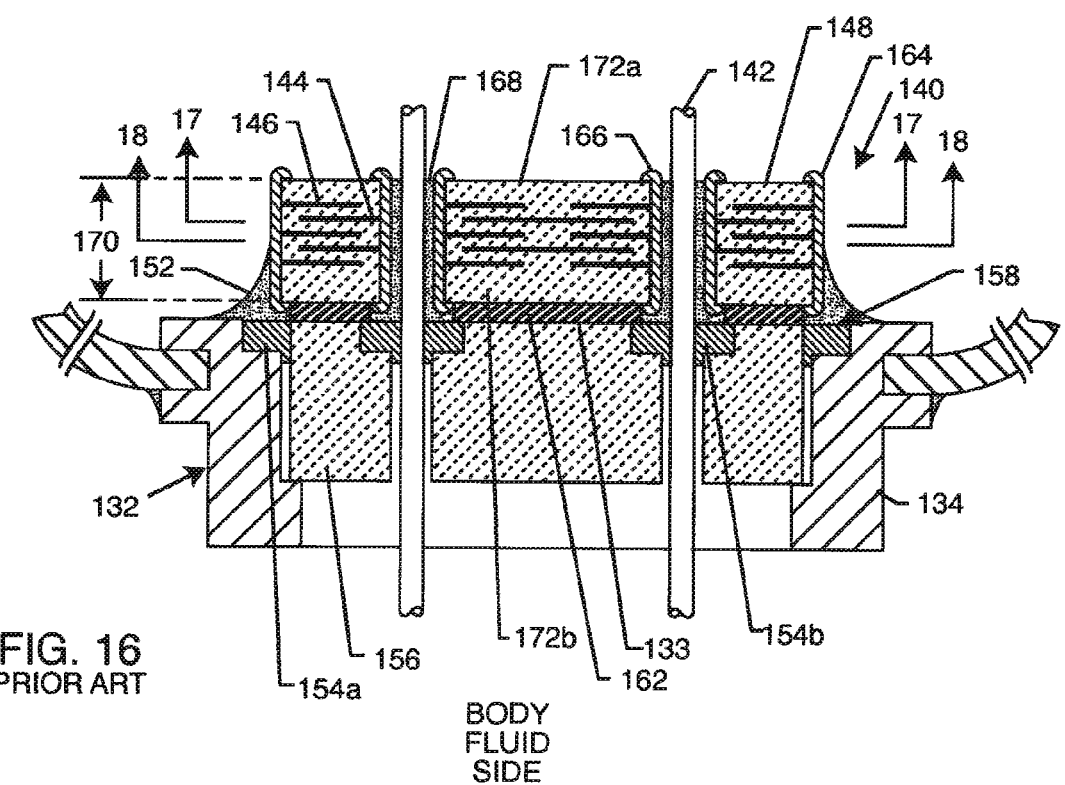
FIG. 16 is an enlarged cross-sectional view taken generally along the line 16-16 from FIG. 15.

FIG. 16 is a cross-sectional view taken generally from section 16-16 from FIG. 15. There are four feedthrough leadwires 142 which extend through the capacitor 140, which has a ground electrode plate set 146 and an active electrode plate set 144.

Figure 17:
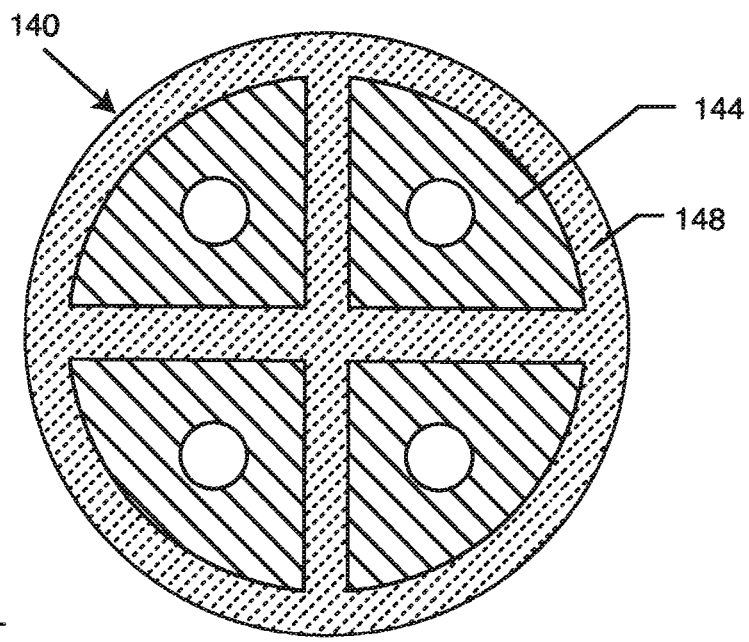
FIG. 17 is an enlarged sectional view taken generally along the line 17-17 from FIG. 16, illustrating the configuration of active electrode plates within the feedthrough energy diverter capacitor.

FIG. 17 is a cross-sectional view taken from section 17-17 from FIG. 16 and illustrates a prior art electrode plate set 144 in that there are very few electrodes. As shown there are only two active electrodes 144 and three ground electrodes 146. This low electrode plate count results in a feedthrough diverter capacitor 140 that has a relatively high ESR at high frequencies. In a recent experiment conducted by the inventors, a typical EIA X7R 400 picofarad feedthrough capacitor with only four electrode plates had an ESR at 1 MHz of 16 Ohms. Re-design of the same geometry (size) capacitor with an EIA NPO dielectric resulted in a 400 picofarad capacitor with over 20 electrodes and an ESR of approximately 1 Ohm at 1 MHz (and around 300 milliohms at 64 MHz). This sixteen to one reduction is a dramatic illustration of the importance of designing the AIMD MRI diverter capacitor 140 for low ESR. For example, for an X7R capacitor the impedance would be the square root of the sum of the capacitor's reactance squared plus the ESR squared. This results in a capacitor impedance Z which is equal to $-j6.22+16$ or approximately 17.2 Ohms. Assuming an MRI induced RF voltage at the AIMD input at 64 MHz of 10 Volts, the RF current diverted through the X7R capacitor is 10 Volts divided by 17 Ohms which is 0.59 Amps. The power dissipation due to the X7R capacitor's ESR ($I^2R$) is $(0.59)^2(17)=5.88$ Watts. This amount of power dissipation is very excessive for such a small component and will cause a temperature rise of over 20 degrees C. On the other hand, the NPO capacitor's impedance is equal to $-j6.22+1$ or $Z=6.3$ Ohms. This lower impedance will result in a much better filter (higher attenuation) and will drop the RF voltage from 16 Volts to approximately 3.71 Volts. This voltage drop is caused by the lead's characteristic impedance and the fact that more current has been drawn through this impedance. This causes a voltage drop in the lead's characteristic impedance as measured at the input to the AIMD. The RF current through the NPO capacitor is then 3.71 Volts divided by 6.3 Ohms which is 0.59-amps. The power dissipation ($I^2R$) is $(0.59 \text{ Amps})^2(1 \text{ Ohm})$ which equals 0.35 Watts which will result in a much smaller temperature rise. Accordingly, the low ESR diverter capacitor 140 design of the present invention offers the following advantages: (1) it has a much lower impedance at 64 MHz and is therefore a more effective EMI filter, and; (2) because it offers higher attenuation, it therefore acts to reduce the MRI induced RF voltage at the input to the AIMD; and (3) as will be shown in the present invention, the diverter capacitor 140 can be designed to conduct or convect heat away and dissipate it over a larger surface area.

The capacitor 140 is bonded with an insulating washer 162 to the hermetic terminal 132. An electrical attachment 152 is made using a thermal-setting conductive adhesive between the feedthrough capacitor outside diameter metallization 164 and gold braze surface 158. The necessity to make an oxide free attachment between the feedthrough capacitor 140 and the ferrule 134 is described in U.S. Pat. No. 6,765,779. An insulator 156 such as glass or alumina ceramic, is hermetically sealed to the ferrule 134 by means of gold braze 154a. The four leadwires 142 are also hermetically sealed to the insulator 156 via gold braze rings 154b (there are four of these). The feedthrough capacitor active electrode plates 144 are attached by co-firing to the capacitor feedthrough hole inside diameter metallization 166. Conductive electrical material 168 is used to attach the metallization 166 to each one of the leadwires 142.

As previously mentioned, FIG. 17 is a cross-sectional view taken generally of section 17-17 from FIG. 16, illustrating the feedthrough capacitor active electrode plate set 144.

Figure 18:
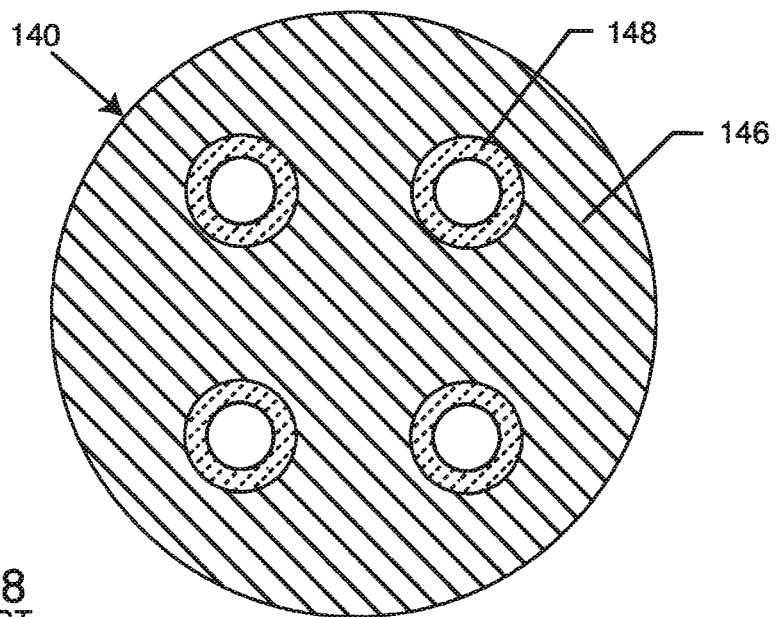
FIG. 18 is an enlarged sectional view taken generally along the line 18-18 from FIG. 16, illustrating the configuration of ground electrode plates within the feedthrough energy diverter capacitor.

FIG. 18 is a cross-sectional view taken generally of section 18-18 from FIG. 16 and illustrates the ground electrode plate set 146.

Referring once again to FIG. 14, one can see that there are only two active electrode plates 144 and two ground electrode plates 146. A low electrode plate count is typically the case for prior art filtered feedthrough (diverter) capacitors 140 used in AIMD applications such as cardiac pacemakers, ICDs and the like. Another reason that the capacitance value is generally low is that a high capacitance value would load down the output of the AIMD. For example, too high of a capacitance value would distort pacemaker therapeutic pulses and also rob energy from the system. An even more extreme example would be the case of an implantable cardioverter defibrillator, wherein too high of a filter capacitance value would seriously degrade the high voltage monophasic or biphasic shock wave form. In the experience of the inventors, the capacitance value for AIMD diverter capacitor 140 is in a relatively narrow range from 10 to 20,000 picofarads. In most cases, the capacitance value is between 350 and 10,000 picofarads. Having a capacitance value between 350 and 10,000 picofarads effectively attenuates most emitters from which AIMDs can be affected. This includes microwave ovens, cellular telephones and the like, which typically operate in the GHz frequency range. The thickness 170 of the capacitor however, cannot be below a certain minimum or the barium titanate based ceramic capacitor will become too fragile. The entire hermetic terminal 132 and the feedthrough capacitor 140 must be able to withstand thermal cycles and shocks including installation by laser welding into the AIMD housing 124. Accordingly, it is very unusual to see a diverter capacitor 140 thickness 170 of less than 20/1000 of an inch. Correspondingly, when one looks at a typical prior art feedthrough capacitor 140 for human implant in cross-section, one sees that there are very few electrodes 144, 146 relative to its overall thickness 170. In fact, there are usually a number of blank dielectric (no electrodes) cover sheets 172 added on the top and/or bottom of the capacitor 140 consisting of ceramic material which is co-fired to add mechanical strength. However, there is a serious downside to having very few electrode plates 144, 146, and that is that the high frequency equivalent series resistance (ESR) of the capacitor increases. For prior art AIMD filter or diverter capacitor 140 having significant dielectric and/or ohmic resistance at high frequencies simply does not matter. This is because the power induced from a typical emitter, such as a cellular telephone or microwave oven results in a trivial amount of RF current flowing through diverter capacitor 140. Even in the most extreme examples, only a few milliwatts of heat would be generated within the capacitor structure itself. However, for high power RF current handling applications, such as diverting MRI induced RF energy, the capacitor dielectric loss and high frequency ESR become critical and must be kept as low as possible. Accordingly, it is a feature of the present invention to have a relatively high number of electrode plates 144, 146 (generally greater than 10). However, with a high k barium titanate based ceramic dielectric with a dielectric constant of around 2500, a high number of electrode plates would result in a very high (too high) capacitance value. A way to solve this is to use a relatively low dielectric constant material, such as EIA Standard NPO material. NPO material has a much lower k (generally, in the area of 60 to 90). Accordingly, in order to achieve the desired capacitance value (in the range of 300 to 3000 picofarads), a much greater number of electrode plates is required. The higher number of electrode plates creates more parallel paths for RF current flow and greatly reduces the ESR of the feedthrough capacitor. One is referred to the equation illustrated in FIG. 29 to explain the relationship between capacitance and the number of electrode plates and other factors.

Figures 19, 20:
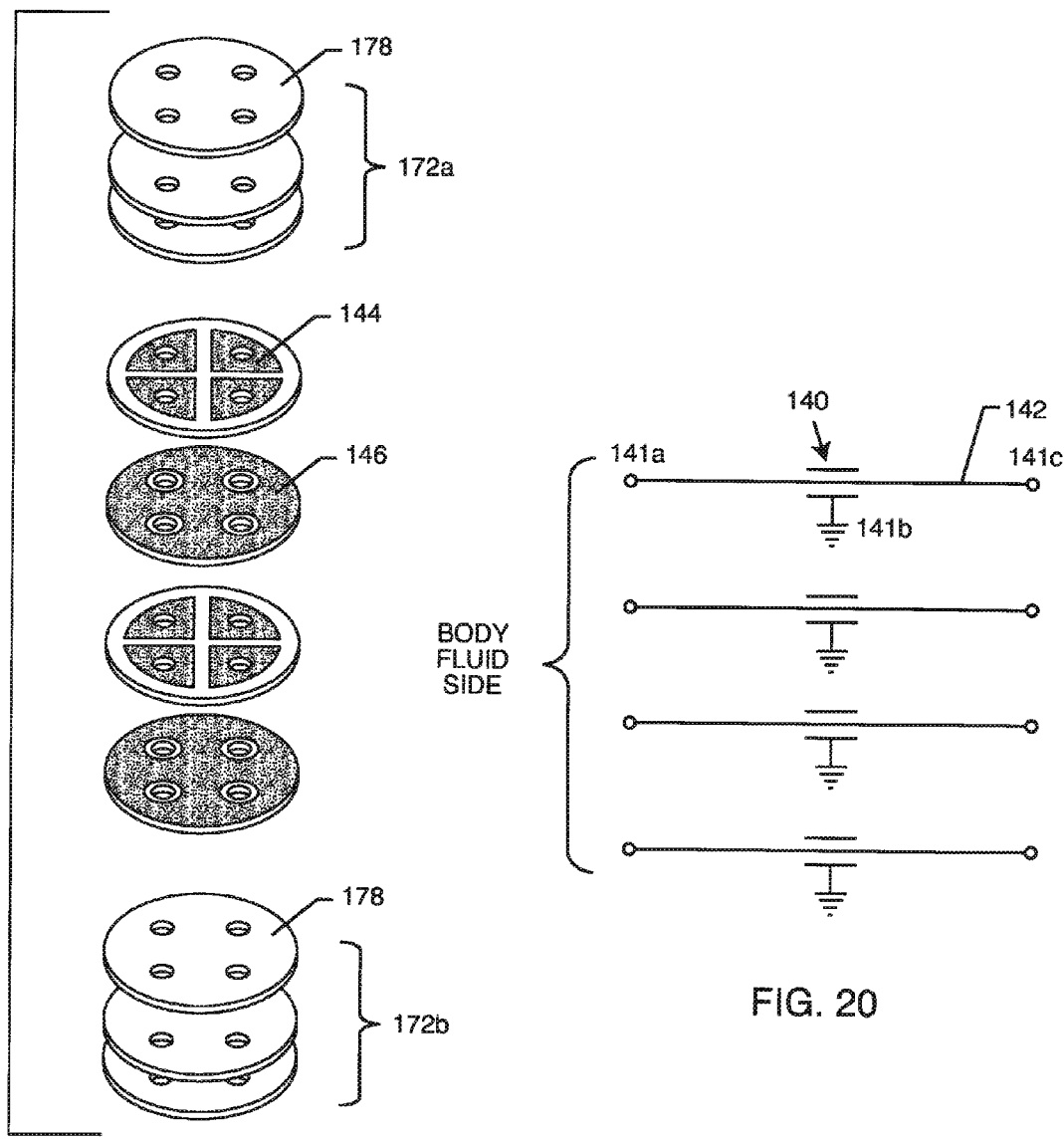
FIG. 19 is an exploded perspective view illustrating the electrode lay-ups of the round quadpolar feedthrough capacitor shown in FIGS. 15 and 16.
FIG. 20 is an electrical schematic diagram of the quadpolar feedthrough capacitor of FIGS. 15-19.

FIG. 19 is an exploded view of the interior electrodes of the prior art quadpolar feedthrough capacitor 140 of FIGS. 15-18. The active electrode plate sets are shown as 144 and the ground electrode plates are shown as 146. One or more cover layers 172 are put on the top and bottom for added electrical installation and mechanical strength. As previously described, this results in a relatively low number of active electrode plates 144 and ground electrode plates 146 which results in a relatively high ESR.

FIG. 20 is a schematic diagram of the quad polar feedthrough capacitor 140 of FIGS. 13 and 15. Feedthrough capacitors are three-terminal devices labeled in FIG. 20 as 141a, 141b, and 141c.

Figure 21:
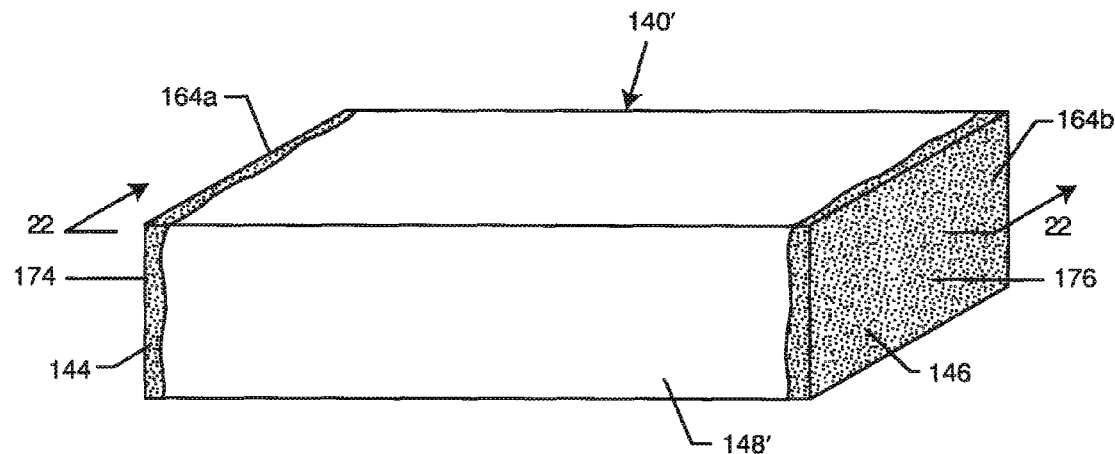
FIG. 21 is a perspective view of a monolithic ceramic capacitor (MLCC)

FIG. 21 is a prior art multi layered ceramic capacitor (MLCC) 140'. These are made by the hundreds of millions per day to service consumer electronics and other markets. Virtually all computers, cell phones and other types of electronic devices have many of these. One can see that the MLCC 140' has a body generally consisting of a high dielectric constant ceramic 148' such as barium titanate. It also has a pair of solderable termination surfaces 164a, 164b at either end. These solderable termination surfaces 164a, 164b provide a convenient way to make a connection to the internal electrode plates 144, 146 of the MLCC capacitor 140'. FIG. 21 can also take the shape and characteristics of a number of other types of capacitor technologies, including rectangular, cylindrical, round, tantalum, aluminum electrolytic, stacked film or any other type of capacitor technology.

Figure 22:
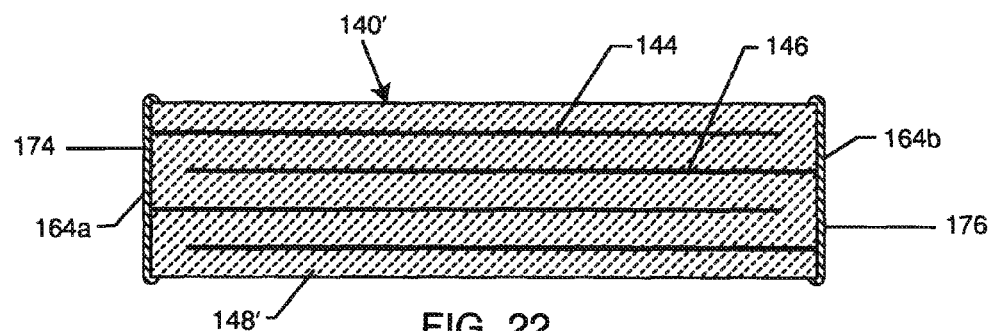
FIG. 22 is a cross-sectional view of the monolithic ceramic capacitor, taken along the line 22-22 of FIG. 21.

FIG. 22 is a sectional view taken from section 22-22 in FIG. 21. The MLCC 140' includes a left hand electrode plate set 144 and a right hand electrode plate set 146. One can see that the left hand electrode plate set 146 is electrically connected to the external metallization surface 164a. The opposite, right hand electrode plate set 146 is shown connected to the external metallization surface 164b. Prior art MLCC 140' and equivalent chip capacitors are also known as two-terminal capacitors. That is, there are only two ways electrical energy can connect to the body of the capacitor. In FIGS. 21 and 22, the first terminal 174 is on the left side and the second terminal 176 is on the right side. As defined herein, MLCC capacitors are two-terminal devices. In contrast, feedthrough capacitors are three-terminal devices which have very low self inductance and make excellent high frequency EMI filters.

Figure 23:
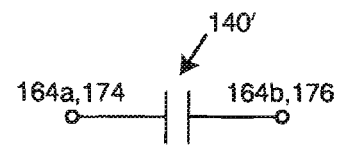
FIG. 23 is an electrical schematic diagram of an ideal MLCC capacitor as illustrated in FIGS. 21 and 22.

FIG. 23 is the schematic diagram of the MLCC chip capacitor 140' illustrated in FIGS. 21 and 22.

Figure 24:
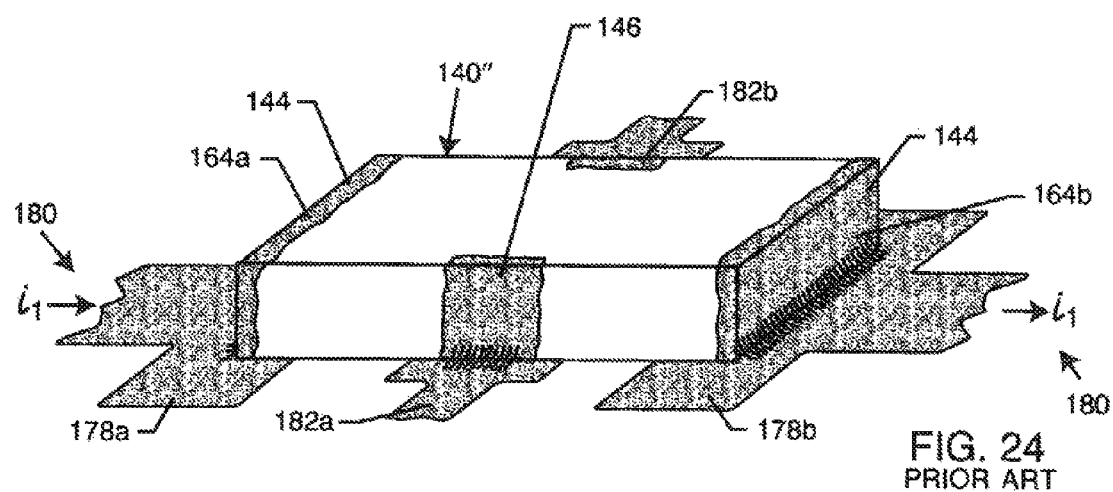
FIG. 24 is a flat-through three-terminal capacitor.

FIG. 24 illustrates another type of prior art 3-terminal filter capacitor known as a flat-through capacitor 140". It is connected at each end to a circuit trace 178a, 178b. A circuit current 180 passes all the way through the capacitor 140". The capacitor 140" is also connected to ground circuit paths 182a, 182b. The overlap of the active electrodes and the ground electrodes creates the capacitance.

Figure 25:
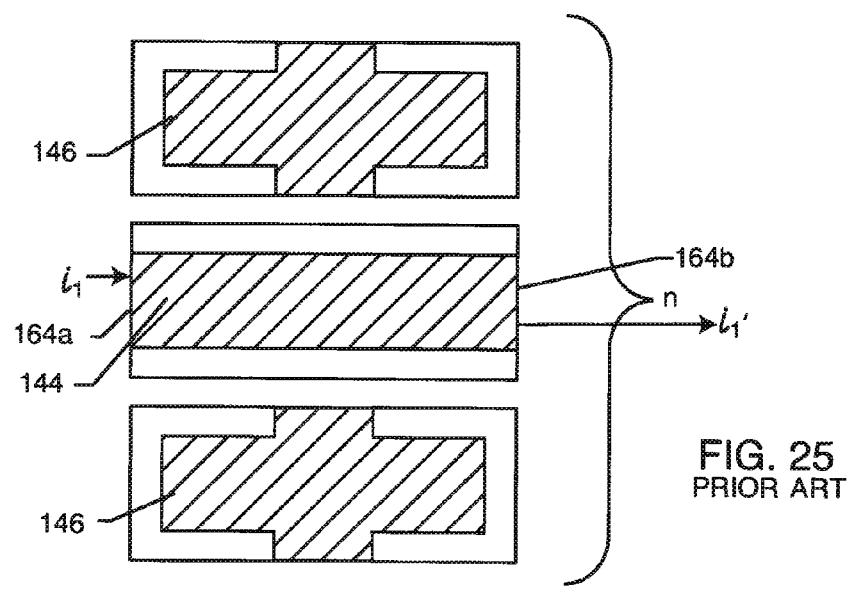
FIG. 25 illustrates the internal electrode plates of the flat-through capacitor of FIG. 24.

FIG. 25 illustrates the internal electrode plates of the flat-through capacitor 140" of FIG. 24. A set of ground plates is illustrated as 146. The through electrode plate 144 is connected to capacitor termination surfaces 164a, 164b.

Figure 26:
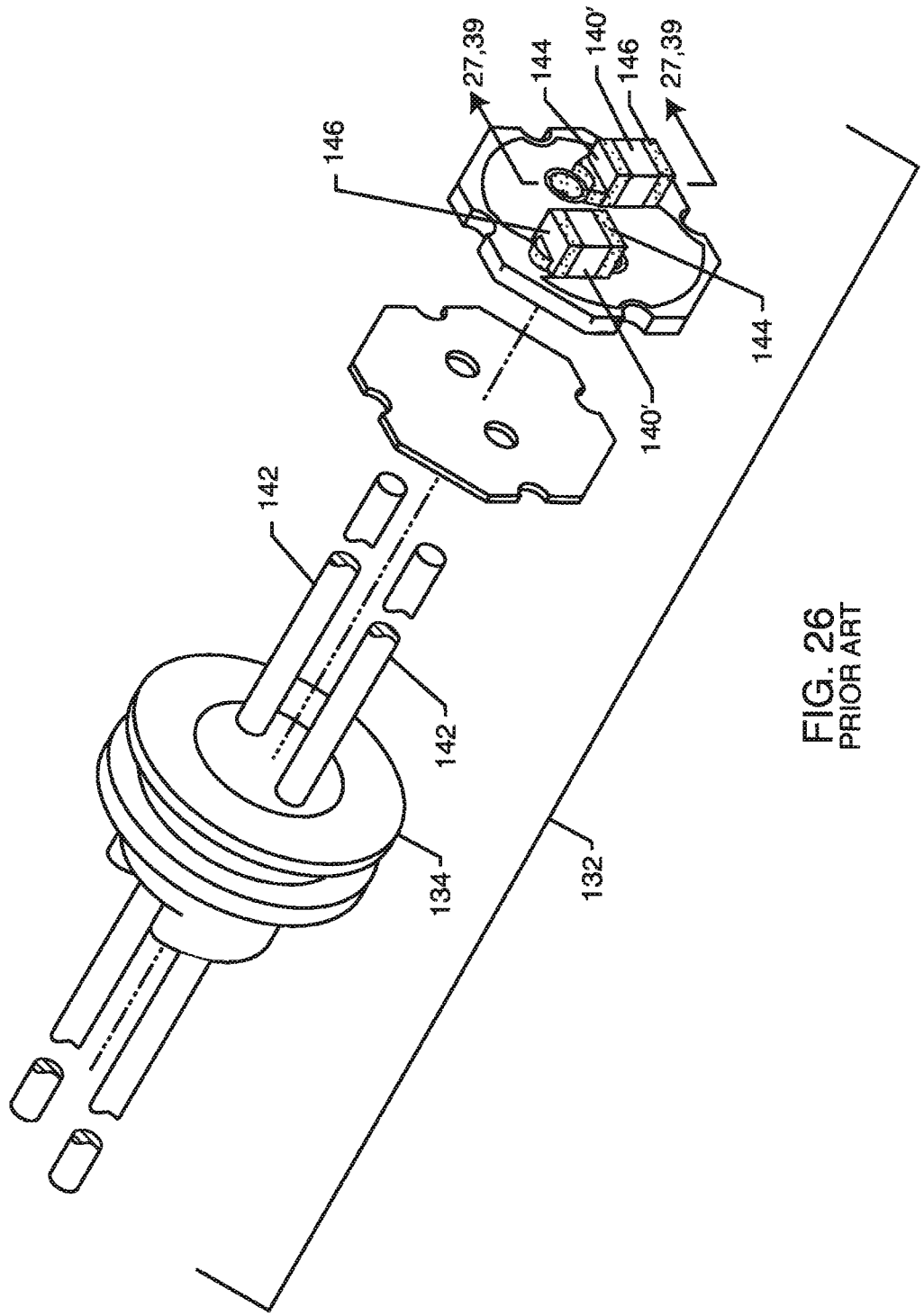
FIG. 26 is a perspective exploded view of a multi-lead hermetic feedthrough with substrate mounted MLCCs showing use of a substrate between the feedthrough and the filter support assembly.

FIG. 26 illustrates a method of attaching MLCC chip capacitors 140' directly to the hermetic terminal 132. In accordance with the present invention, the MLCC capacitors 140' would be of relatively low dielectric constant, like NPO such that they will have a high number of electrode plates thereby minimizing their ESR. This would make them very effective in diverting high levels of RF current at an MRI RF pulsed frequency. One is referred to U.S. Pat. Nos. 5,896,267 and 5,650,759, both to Hittman et al., which more thoroughly describe the use of MLCC capacitors as filters attached at or near the hermetic terminal of an active implantable medical device. These two patents are incorporated herein by reference.

FIG. 27 is a cross-section of a typical MLCC capacitor 140', such as those used in FIGS. 21 and 26 (except that the ESR would be high due to the low number of electrodes). The principles of this cross-section are also equally applicable to any type of feedthrough capacitor 140, such as that described in FIGS. 13 and 15. In general, the equivalent series resistance of a capacitor depends upon a number of very important variables. The capacitor's ESR is the sum of the connection resistance ($R_c$) 184, the resistance of attachment materials ($R_a$) 186, the resistance of capacitor metallization (used to attach to internal electrode plates) ($R_m$) 188, the resistance of the electrodes ($R_e$) 190 and 190' and also the resistance of the dielectric loss tangent ($R_{DL}$) 192. There is also another type of resistance (not shown) which occurs at very high frequency, known as skin effect ($R_s$). This is a situation in which the bulk of the current flow is on the skin of electrodes and circuit connections instead of uniformly distributed throughout a conductor. This has the affect also of increasing a capacitor's ESR. In general, for typical MRI RF pulsed frequencies, skin effect can be ignored (it's mostly a greater than 500 MHz phenomenon).

FIG. 28 is the schematic diagram from FIG. 27 showing that for these purposes, the capacitor's ESR is the sum of the connection resistance ($R_c$) 184, the connection material ($R_a$) 186, the metallization ($R_m$) 188, the electrode plate resistance ($R_e$) 190 and the capacitor's dielectric loss ($R_{DL}$) 192. The capacitor's dielectric loss ($R_{DL}$) 192 is frequency variable, which will be explained in further detail. For a well designed and properly installed capacitor, many of these resistances are so small that they can be ignored. For example, referring once again to FIG. 27, if the capacitor metallization ($R_m$) 188 is well designed and properly attached, it will have a trivially small resistance. In a similar fashion, if the electrical attachment material ($R_a$) 186 is a solder or a proper thermal-setting conductive adhesive, it will also have a trivial amount of resistance. If the system is attached to gold or another similar non-oxidized surface, then the connection resistance ($R_c$) 184 would also be trivially small or about zero. Referring once again to FIG. 28, one can see that the total ohmic losses are $R_o$ 200, and in this case, $R_o$ consists almost entirely of the total electrode plate resistance ($R_{e(total)}$) 190. This is why it is so important in the present invention to maximize the number of electrode plates. At high frequency, the ohmic loss of the low dielectric constant capacitor is almost entirely due to the resistive loss of the active and ground electrode plates ($R_{e(total)}$ 190).

FIG. 29 gives the equation relating capacitance to the dielectric constant k, the active (overlap area) of the electrode plates A, the number of electrode plates n and the dielectric thickness d. Since the dielectric constant k is directly related to the capacitance C, one can see how dramatically the capacitance would rise when the dielectric constant k is 2500 as opposed to a k below 200 for an EIA Class I dielectric of the present invention, Assuming a constant dielectric thickness d for a particular voltage rating, the only way to increase the capacitance to its original value, would be to greatly increase the number of electrode plates. In the prior art, this would be counterintuitive. However, in the present invention, this is exactly what we want to do. A high number of electrode plates drives down the high frequency ohmic losses and thereby greatly increases the efficiency of the capacitor to pull RF energy out of an implanted lead during MRI scans. In addition, the high number of electrode plates has a very low equivalent series resistance at the MRI RF-pulsed frequency, thereby significantly reducing the amount of heat that would be produced in the filter diverter capacitor 140.

Figures 30, 31:
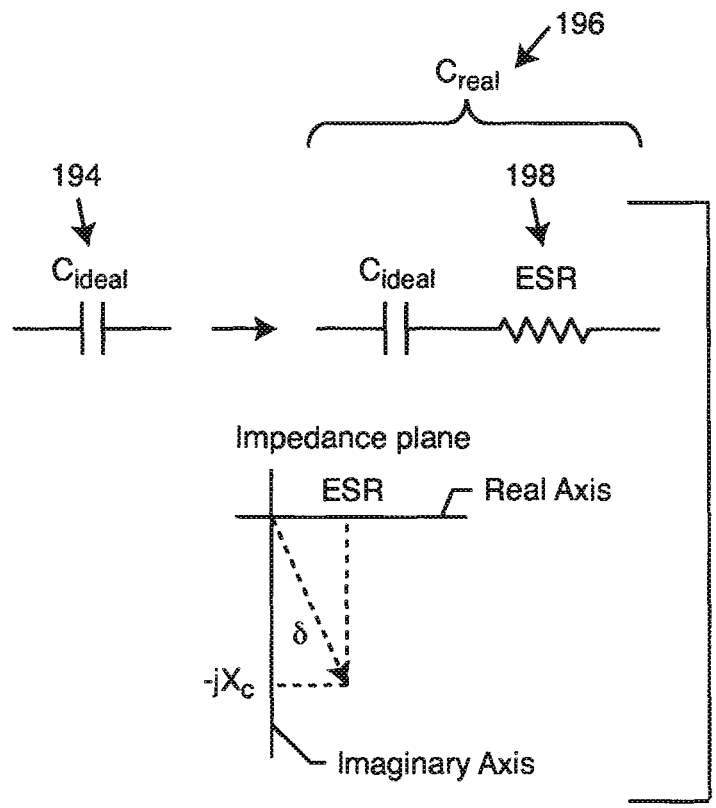
FIG. 30 shows the difference between an ideal capacitor and a real capacitor, including dielectric loss tangent and dissipation factor.
FIG. 31 gives the formulas for capacitive reactance, dissipation factor, equivalent series resistance (ESR) and dielectric loss tangent.

FIG. 30 illustrates an ideal capacitor 194 and also a non-ideal capacitor 196 which consists of an ideal capacitor 194 in series with its ESR 198. For the purposes of the present discussion, a capacitor's series inductance or insulation resistance (a parallel resistance) can both be ignored. This is because the inductance of feedthrough capacitors is quite low at MRI RF-pulsed frequencies. Further, the capacitor's insulation resistance is generally in the megohms or gigohms range, which is so high, it can also be ignored as a parallel path. Also shown is a graph of the impedance plane showing the capacitor ESR in the real axis and the capacitive reactance $-jX_C$ shown on the imaginary axis. The capacitor's loss tangent $\delta$ is also illustrated.

In FIG. 31, equations are given for capacitive reactance $X_C$ and dissipation factor DF and also for the tangent of $\delta$, which is also defined as dissipation factor DF. Historically, dissipation factor has been expressed as a percent, such as 2.5% maximum. This would mean that the allowable dissipation factor would be 2.5% of the capacitor's capacitance reactance at a particular frequency. Usually, due to dielectric losses, this number is dominated at low frequencies by the capacitor's dielectric loss. The capacitor's dielectric loss is generally related to its dielectric constant and the frequency of the driving energy. For example, if the frequency of an applied sinusoid is relatively low (say 60 Hz) then the crystal lattice of the capacitor has plenty of time to deflect back and forth under the electrical stress and in so doing, produces a significant amount of heat which is a type of real or resistive loss. At 1 kHz, the capacitor dielectric structure (or dipoles, if one uses that theory) vibrates at a higher frequency. As one goes higher and higher in frequency, say to 10 MHz, then for the Class I dielectrics of the present invention, there would be very little movement in the crystal lattice and accordingly, very little heat generated due to dielectric loss. It will be further illustrated how dielectric loss varies with frequency. In the past, particularly as described by testing specifications such as MIL-Std-202, dissipation factor is measured either at 1 kHz, or in some cases, at 1 MHz. Unfortunately, this data is misleading at MRI RF-pulsed frequencies which generally are 21.28 MHz (0.5 T), 64 MHz (1.5 T) or higher. For most dielectrics, the high frequency ohmic loss, due to the capacitor's electrode plates, is so low that it is masked by the capacitor's dielectric loss when measured at low frequencies such as 1 kHz or 1 MHz. This will be explained in subsequent Figures.

Figure 32:
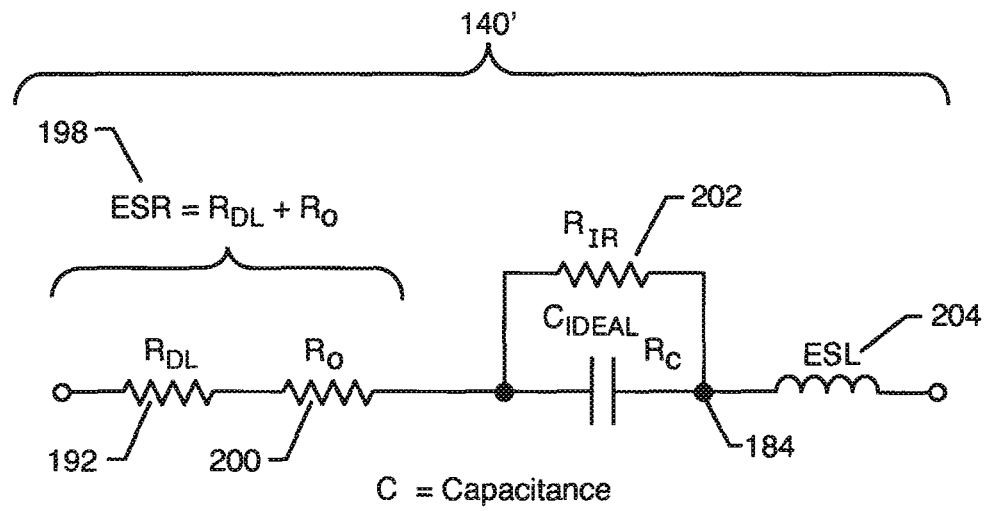
FIG. 32 is an equivalent circuit model for a real capacitor.

FIG. 32 is a more complete schematic for a capacitor, which has been simplified from FIG. 28. ($R_o$) represents ohmic loss 200 which is the sum of the connection loss ($R_c$) 184, the attachment materials ($R_a$) 186, the metallization ($R_m$) 188, and the electrode plate resistance ($R_e$) 190. Assuming that the connection resistance ($R_c$) 184 is very low, such as in attachment to gold, and that the attachment material ($R_a$) 186 has a very low resistivity, such as a thermal-setting conductive adhesive or a solder, and assuming that the capacitor metallization 188 materials have very little ohmic resistance to the electrode plates, then one can assume that the bulk of the entire ohmic loss ($R_o$) 200 is equal to the resistance of the electrode stack ($R_{e(total)}$) 190. As previously described, the resistance of the electrode stack depends on the length, the width and the thickness of the electrodes and importantly, also the number of electrodes that are in parallel. Therefore, reducing the dielectric loss and maximizing the number of electrodes, are key featured embodiments of the present invention.

Figure 33:
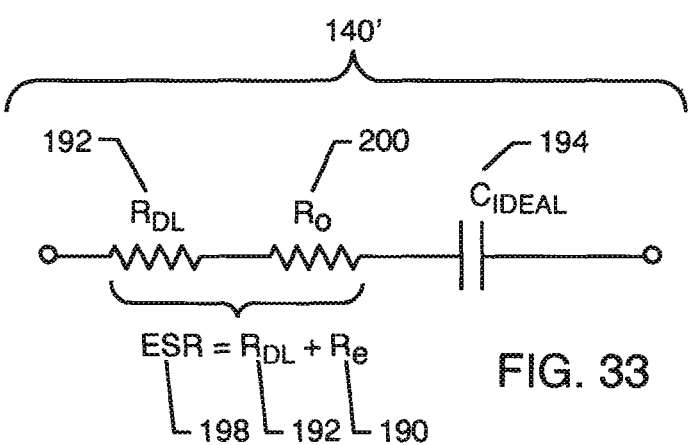
FIG. 33 is a schematic illustrating a simplified model for capacitor ESR.

FIG. 33 is a simplified schematic diagram of the present invention from FIG. 32 showing that the ESR 198 is the sum of the dielectric loss ($R_{DL}$) 192 plus the total parallel resistance of the electrode stack ($R_e$) 190. Referring once again to FIG. 32, one can see that there is a resistor ($R_{IR}$) 202 in parallel with the ideal capacitor C 194. This resistance ($R_{IR}$) 202 is known as the capacitor's insulation resistance. In a high quality capacitor, this resistance value tends to be in the hundreds of megohms or higher and can therefore be ignored as part of the equivalent circuit model for the purposes herein. For three-terminal or physically small MLCCs, the equivalent series inductance (ESL) 204 as shown in FIG. 32 is a very small value and can also be ignored for the purposed herein. In addition, ESL 204 is imaginary and does not contribute to power loss or ESR 198 in a capacitor.

Accordingly, as shown in FIG. 33, the AIMD diverter capacitor 140' ESR 198 is the sum of the dielectric loss ($R_{DL}$) 192, the ohmic losses ($R_o$) 200 and any losses due to skin effect ($R_s$) 206. However, at MRI RF frequencies, skin effect is negligible and may be ignored. Referring once again to FIG. 33, assuming that the capacitor has good metallization, oxide free connection to the ferrule and good electrical attachment materials, then the ohmic losses ($R_o$) 200 are completely dominated by the resistance of the electrodes ($R_{e(total)}$) 190. Accordingly, for the purposes of the present invention, the ESR 198 is generally equal to the dielectric loss 192 plus the electrode losses ($R_e$) 190. Both of these parameters must be carefully controlled for the high power RF diverter capacitor 140' of the present invention.

It has been shown that dielectric loss is a frequency variable. At MRI RF pulsed frequencies, for an EIA Class I ceramic capacitor, the dielectric loss drops to a very low value (it is essentially zero). Therefore, in the present invention, which is based on EIA Class I dielectrics, the diverter capacitor's 140' ESR 198 is primarily determined by the total resistance of its electrode plates ($R_e$) 190.

Figure 34:
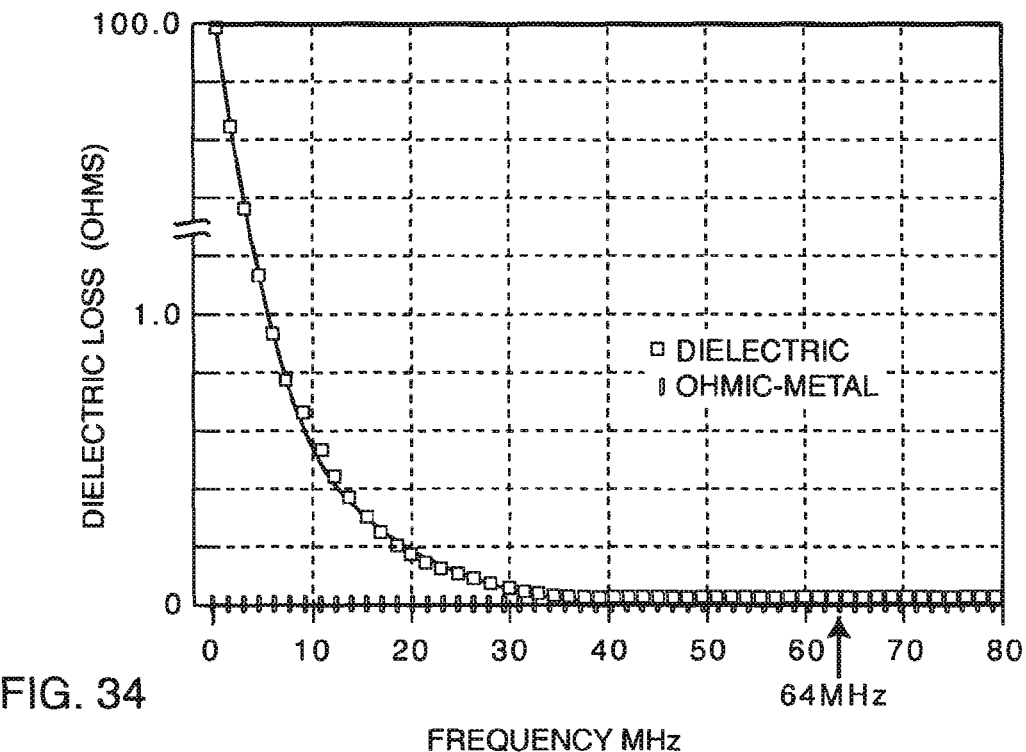
FIG. 34 is a graph illustrating capacitor dielectric loss versus frequency.

FIG. 34 illustrates the dielectric loss in ohms for a relatively low dielectric constant ceramic capacitor. One can see, at low frequencies, the dielectric loss in ohms can be over 1000 ohms or even much greater. However, as one increases in frequency, one can see that the dielectric loss drops and is nearly zero at 64 MHz (1.5 T MRI scanner RF-pulsed frequency).

Figure 35:
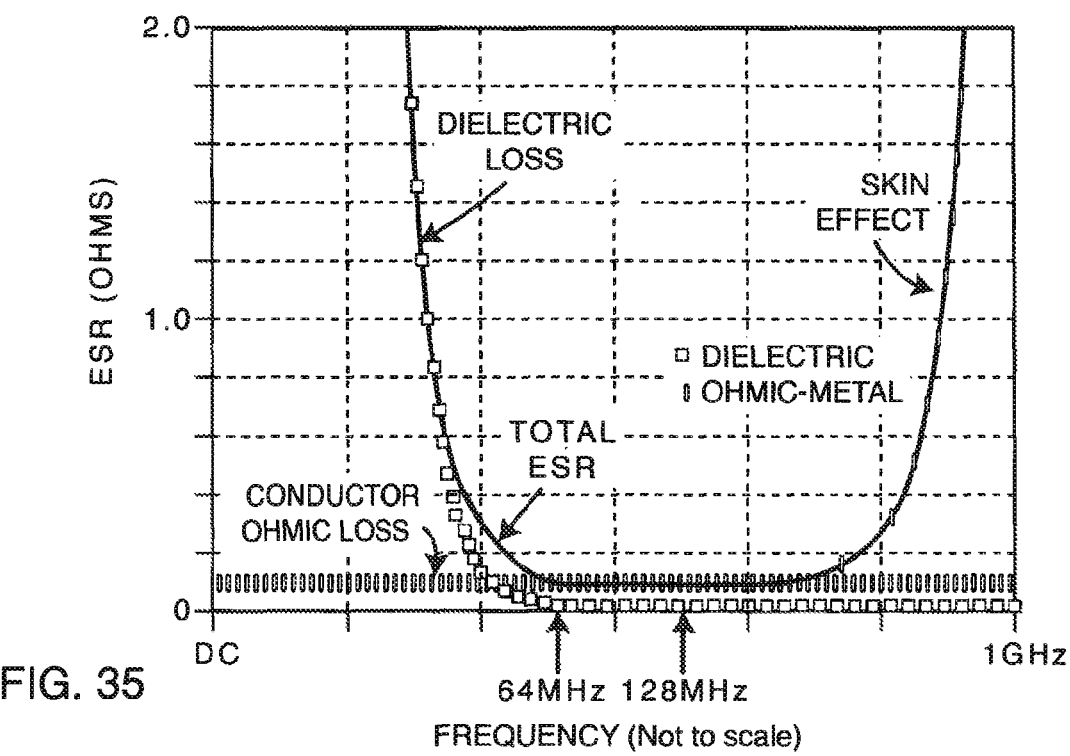
FIG. 35 is a graph illustrating normalized curves which show the capacitor equivalent series resistance (ESR) on the y axis, versus frequency on the x axis.

FIG. 35 shows a U-shaped composite curve. It is the summation of capacitor ohmic loss which includes the total resistance of capacitor electrodes, electrical attachment materials, capacitor metallization, and electrical connection material. As one can see, ignoring skin effect, the conductor ohmic loss for the capacitor is relatively constant from low frequency all the way to very high frequencies. For a Class I dielectric, the capacitor dielectric loss (marked with small squares) is a very high value at low frequency, and then drops to near zero at MRI RF frequencies such as 64 MHz and 128 MHz. Skin effect is also shown, which would be an ohmic loss for two-terminal type capacitors. The total ESR is the solid line, which is the summation of the capacitor dielectric loss, the capacitor conductor ohmic loss and skin effect. The present invention is directed to make sure the center of this U-shaped curve falls on the range of MRI RF-pulsed frequencies.

FIG. 36 is a table showing an example of losses (actually measured) for a prior art 2000 picofarad X7R feedthrough capacitor. This particular capacitor had a dielectric constant of about 2500. One can see that at 1 kHz, the dissipation factor is about 1591.55 ohms, which when added to the ohmic losses, results in an equivalent series resistance of about 1591.98 ohms. Even at 1 MHz for this capacitor, there is about 1.59 ohms of dissipation factor loss, which when added to the about 0.432 ohms of ohmic loss, yields an ESR of about 2.024 ohms. As one can see, again referring to MIL-Standard-220 and many other test specifications, measuring the capacitor's real losses, at 1 kHz and 1 MHz, is not a useful way to analyze the capacitor's losses at MRI RF-pulsed frequencies. For this, one needs to look in the range from 10 to 500 MHz and realize that as the dissipation factor drops, the ohmic losses still dominate and one ends up with a significant ESR ranging from about 0.591 to about 0.434 ohms.

FIG. 37 dramatically illustrates the difference when one uses an EIA Class I dielectric, such as COG (NPO), which has a dielectric constant of less than about 200. Because of this low dielectric constant, one is forced to use a very high number of electrode plates. This has the effect of greatly reducing the capacitor's ohmic losses. In addition, Class I dielectrics have a lower dissipation factor, particularly at high frequency. Comparing 100 MHz, one can see for the COG dielectric, the ESR is about 0.201 ohms at 100 MHz, which is a significant reduction compared to the X7R capacitor. In the preferred embodiment (illustrated in FIGS. 39-93), the ESR would drop to below 0.1 ohms, which would result in a significantly reduced heat generation in the present invention diverter capacitor 210.

Figure 38:
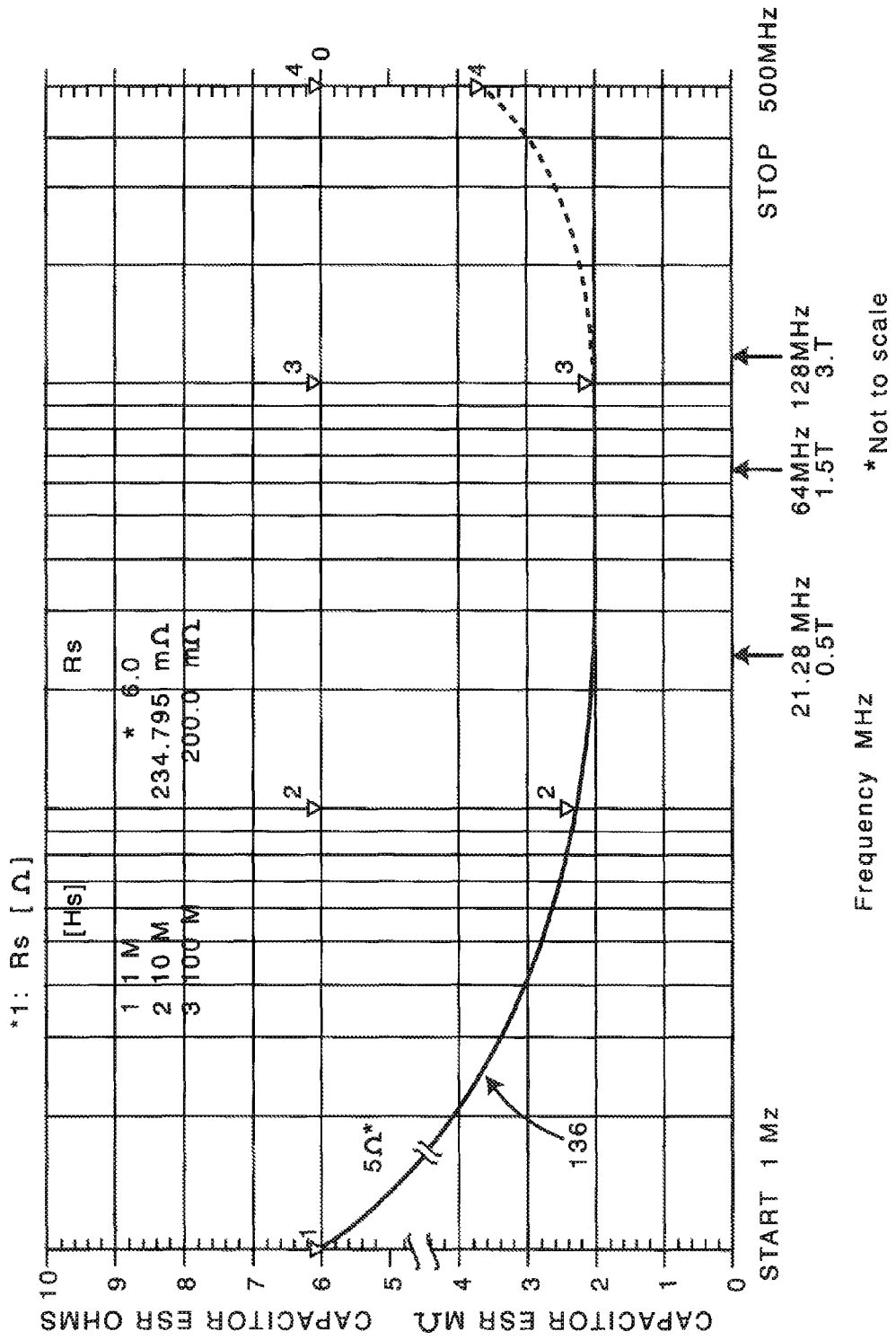
FIG. 38 is a graph illustrating capacitor equivalent series resistance versus frequency as illustrated in a sweep from an Agilent E4991A materials analyzer.

FIG. 38 is a scan of the capacitor's ESR taken from an Agilent Materials Analyzer. At the start frequency of 1 MHz, one can see that the capacitor's 210 ESR is on the order of 6 ohms, which is very high. However, by using a EIA Class I dielectric, by the time one reaches about 21.28 MHz (the frequency of a 0.5 T MRI scanner), the dielectric loss has flattened out (reached about zero). The only loss left is the ohmic loss of the capacitor, which at 100 MHz is only 200 milliohms. Also shown are the RF-pulsed frequencies for a 1.5 Tesla scanner (64 MHz) and a 3 Tesla scanner (128 MHz).

Since the 1960s it has been a common practice in the capacitor industry to measure capacitance and dissipation factor at 1 kHz. The dissipation factor is usually defined as a percentage, for example, 2.5% maximum. What this means is that the dielectric loss resistance can be no more than 23% of the capacitive reactance at a certain frequency (usually 1 kHz). For example, if the capacitive reactance for a particular capacitor was 80,000 ohms at 1 kHz with a 2% dissipation factor this would equate to 1600 ohms of resistance at 1 kHz. FIG. 38 also illustrates that the dielectric loss essentially goes to about zero at high frequency. For typical low dielectric constant Class 1 ceramic capacitors, frequencies above 10-20 MHz will be sufficiently high so that the dielectric loss is no longer a factor in the capacitor ESR measurement. In summary, the ESR of the capacitor 210 varies with the capacitance value, the number of electrode plates, and the length and width of the electrode plates. Accordingly, a wide range of "normal" ESR readings can be obtained for many types of capacitors. For one particular capacitor a normal ESR reading might be 0.05 ohms and for another design as much as 10 ohms.

Figures 39, 40:
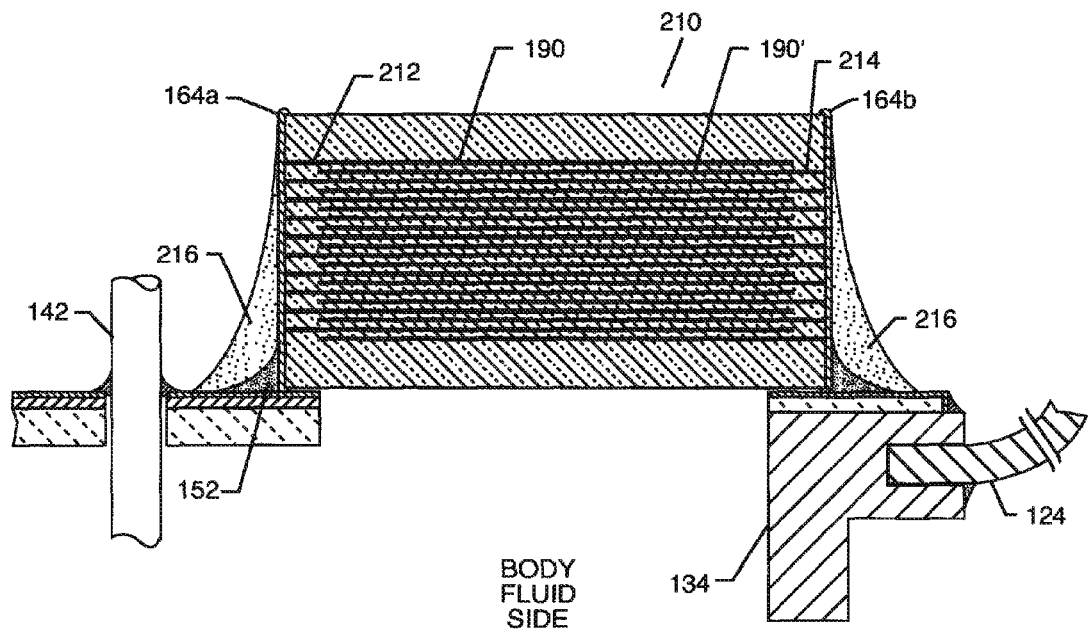
FIG. 39 is a cross-sectional view of a lower k MLCC with an increased number of electrode plates to minimize ESR.
FIG. 40 is an equation showing that the total high frequency electrode resistive losses drop in accordance with the parallel plate formula for capacitor electrodes.

In the present invention, as shown in the embodiment of FIG. 39, maximization of the number of electrode plates in order to reduce the electrode resistance ($R_e$) becomes paramount. In general, in order to increase the number of electrode plates, the effective capacitance area (ECA) can be minimized and the dielectric constant lowered so that one ends up with a relatively high number of electrode plates. One might ask, why doesn't one simply make the electrode plates much thicker in order to decrease their resistance? It would be true that making the electrode plates very thick would reduce their resistance; however, there would be an undesirable consequence. The capacitor would no longer be a monolithic layer and would simply represent a sandwich somewhat like a deck of cards that is ready to come apart at the first thermal shock or piezoelectric effect. It is a basic tenet of ceramic engineering that electrodes be thin enough, and contain enough ceramic powder such that when sintered, the ceramic capacitor structure become truly monolithic. This leaves the designer with only a few effective ways to control the capacitor's ESR. For a given geometry, which is usually dictated by the AIMD design, there are very few degrees of freedom in the length, width and geometry of capacitor electrode plates. Accordingly, in the present invention, maximizing the number of electrode plates becomes a key design factor. This goes hand in hand with the capacitor's dielectric constant k. In other words, reducing the dielectric constant means that the number of capacitor electrode plates must increase to achieve the same capacitance value. This naturally reduces the capacitor's ESR and increases its ability to handle high levels of RF current. Another reason to keep the ESR 198 of the diverter capacitor's 210 extremely low is so it does not overheat while diverting high levels of RF current to the EDS housing 124 of the AIMD 100. The RF currents are literally conducted through the capacitor's 210 electrode plates 212, 214 and hence through the electrode plate resistance ($R_e$) 190. Electrode plate resistance ($R_e$) 190 is the sum total of the resistance of all of the electrode plates 212, 214 acting in parallel. If the electrode plate resistance ($R_e$) 190 were high, then there would be a tremendous amount of $I^2R$ power loss that occurs and the capacitor 210 would rapidly get very hot and perhaps destroy itself and/or the surrounding electrical connections or materials. Another reason to keep the capacitor 210 ESR 198 relatively low is so that it represents a very low impedance Z at the MRI RF pulsed frequency. This will increase its ability to draw energy from the implanted lead 110 and divert it as an energy dissipating surface to the AIMD housing 124. If the capacitor represented too high of an impedance, this would reduce the current, but would also mean that more energy was undesirably left in the implanted lead 110. Lowering the impedance Z of the diverter capacitor 210 also means that it will be a better EMI filter by offering increased attenuation at the MRI RF pulsed frequency.

FIG. 39 illustrates a cross-section of a multilayer ceramic capacitor MLCC 210 of the present invention which is very similar to the prior art MLCC 140 illustrated in FIG. 21. FIG. 39 can also be equivalent to any of the aforementioned feedthrough capacitors. In the present invention, feedthrough capacitors or MLCCs can act as high power RF energy diverters. Energy diverters using an energy dissipation surface 134, 124 are more thoroughly described in Published Application Nos. 2010/0217262 and 2010/0023000, the contents of which are incorporated herein by reference. The key difference is that the number of electrode plates, both active 212 and ground 214, has been substantially increased in order to reduce the capacitor's 210 ESR 198 to below 2 ohms. In a particularly preferred embodiment, the capacitor's ESR 198 would be below 1 ohm. As previously mentioned, a way to accomplish this without the capacitance value becoming too high would be to decrease the dielectric constant such that a high number of electrode plates would be required. In a particularly preferred embodiment, the dielectric material would be an EIA Standard Class I type such as NPO. Referring once again to FIG. 39, one can see the active (left hand) electrode plates 212 and the ground electrode plates (right hand) 214 stacked in interleaved relation. An electrical attachment material 152 is shown which connects the capacitor metallization 164, 188 to the ferrule of a hermetic terminal 134. In general, the electrical connection material 152 would be highly electrical conductive, but not, necessarily highly thermally-conductive. In a preferred embodiment, a highly thermal-conductive overlay material 216 has been added in order to efficiently conduct heat from the capacitor electrode plates 212, 214 and terminations 164a, 164b to the ferrule 134 and/or lead 142. As an example, this MLCC capacitor type construction can be mounted to a hermetic terminal 134 as shown in FIG. 26. In summary, the capacitor 210 embodied in FIG. 39 is based on an EIA Class I dielectric, which means its dielectric constant is relatively low and its temperature coefficient, as given by standard ANSI/EIA-198-1, published Oct. 29, 2002, with reference to Table 2 permissible capacitance change from 25 degrees C. (ppm/degree C.) for Class I ceramic dielectrics. This indicates that the maximum allowable change varies from +400 to −7112 parts per million per degrees centigrade. As previously mentioned, a particularly preferred embodiment would be the COG dielectric, which is also commonly referred to as NPO. The thermally-conductive overlay material 216, shown in FIG. 39, is preferred, but optional.

FIG. 40 is an equation showing the effect of the parallel plate resistances. FIG. 40 gives the equation for the total resistance of the capacitor's electrode plates ($R_e$) 190 as the parallel summation of all of the capacitors' electrode plates 212, 214 ("n" electrode plates).

Figure 41:
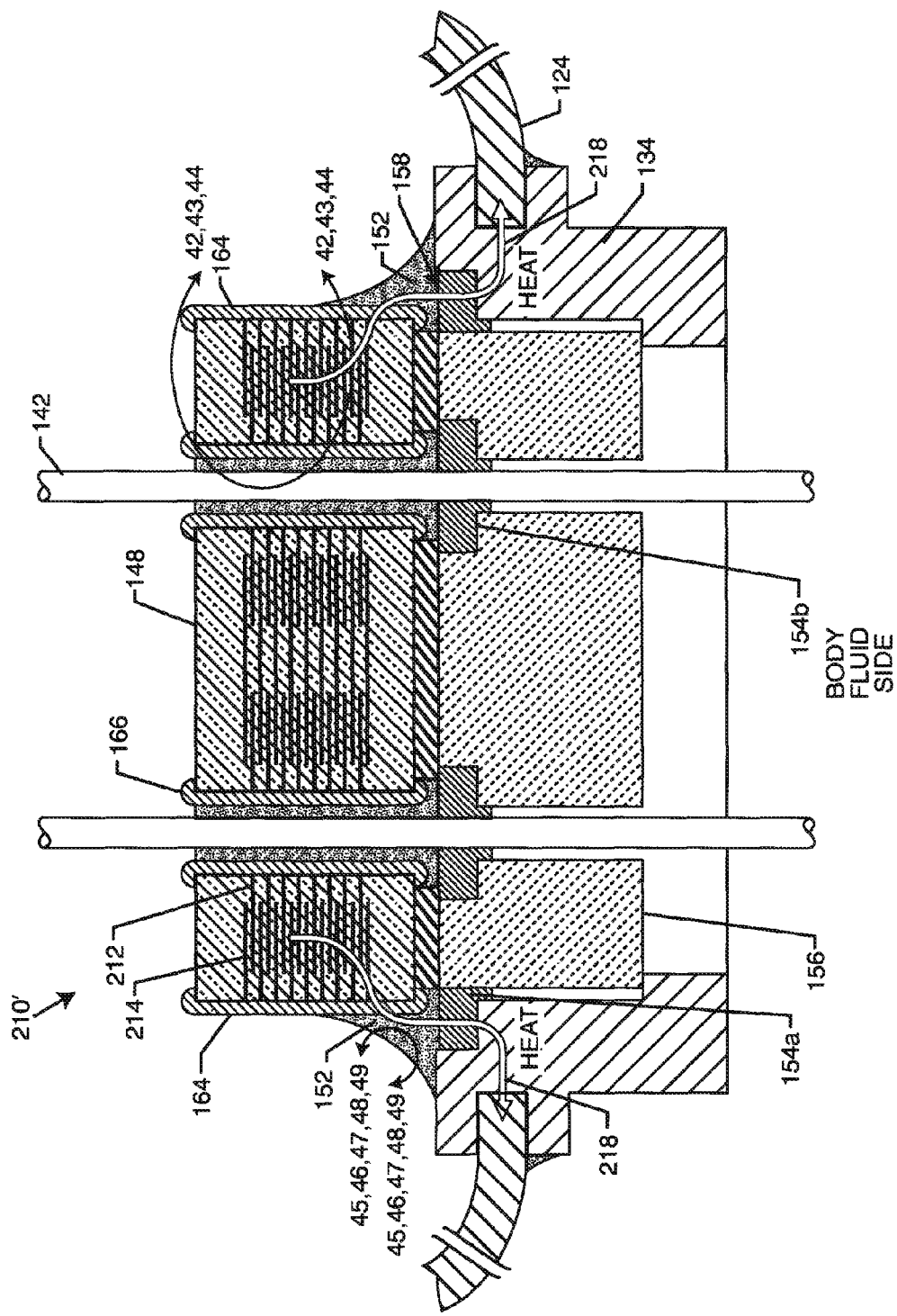
FIG. 41 is a cross-sectional view of a quad polar feedthrough capacitor similar to FIG. 15 except that it is low ESR and designed for maximal heat flow.

FIG. 41 is very similar to the cross-section of the quad polar capacitor previously described in FIG. 15. Again, the number of electrode plates 212, 214 have been increased in accordance with the present invention such that the FIG. 41 quad polar diverter capacitor 210' has a high frequency ESR 198 generally less than 2 ohms. Referring once again to FIG. 41, one can see that the capacitor outside diameter (ground) metallization 164 is attached using a conductive material 152 to a gold surface 158 on ferrule 134. All of these connections, when properly done, have negligible resistance. Accordingly, the capacitor's 210' ESR 198, at high frequency, is made up of the total of the resistance ($R_e$) 190 of the ground electrode plates 214 and the resistance ($R_e'$) 190' of the active electrode plates 212 all acting in parallel. As previously stated, for Class I dielectrics, the capacitor's dielectric loss 192 can be ignored at MRI RF pulsed frequencies since it becomes negligible at RF-pulsed frequencies. Also, for a feedthrough capacitor geometry, skin effect 206 is also negligible. Referring once again to FIG. 13, one can see a similar rectangular quadpolar capacitor that is attached to a gold braze surface 158.

Figure 42:
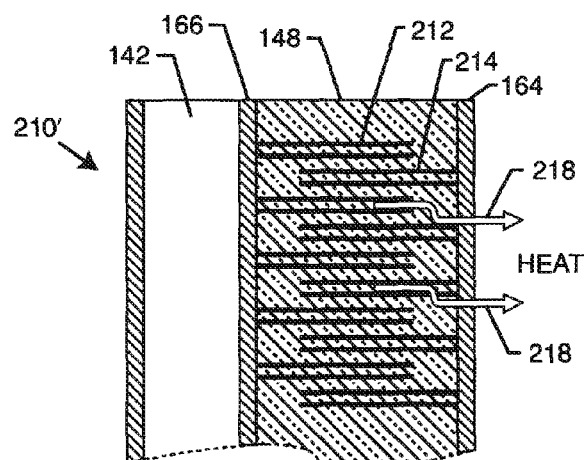
FIG. 42 is a partial section taken from Section 42-42 from FIG. 41 illustrating dual electrode plates to minimize capacitor ESR and maximize heat flow out of the capacitor.

FIG. 42 is taken from section 42-42 from FIG. 41 and illustrates a doubling of the capacitor's active 212 and ground 214 electrode plates. Doubling the electrode plates 212, 214 is very effective since both plates are still exposed to the capacitor's internal electric fields and therefore, both sets of doubled plates will have electrode plate displacement currents (RF currents). This has the effect of greatly increasing the number of electrode plates as illustrated in the equation in FIG. 40, which significantly reduces the overall electrode plate resistance. Dual electrodes are shown in U.S. Pat. No. 5,978,204 to Stevenson et al., the contents of which are incorporated herein by reference. In the '204 patent, the dual electrodes were utilized to facilitate high pulse currents, for example, in an implantable defibrillator application. Double electrodes are very useful in the present invention to drive down electrode plate resistance, thereby driving down the capacitor's 210' high frequency ESR 198 and also to increase the conduction of heat 218 out of the capacitor 210' during exposure to high power MRI RF-pulsed environments.

Figure 43:
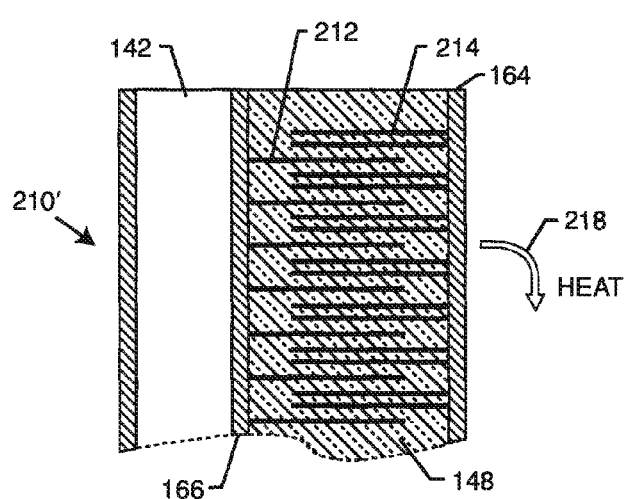
FIG. 43 is similar to FIG. 42 except that just the ground electrode plates have been doubled.

FIG. 43 is very similar to FIG. 42 except in this case, only the ground electrode plates 214 have been doubled. Increasing the number of ground plates 214 is particularly efficient in the removal of heat. As shown, the ground plates 214 are utilized to conduct heat away from the diverter capacitor 210' and direct it through the ferrule of the hermetic seal 134 to the housing 124 of the AIMD 100, which has a relatively large surface area. The relatively large surface area of the AIMD 100 means that a great deal of RF or thermal energy can be dissipated without concentrating it in a small location, which would lead to a very high temperature rise and possibly damage surrounding body tissue damage.

Figure 44:
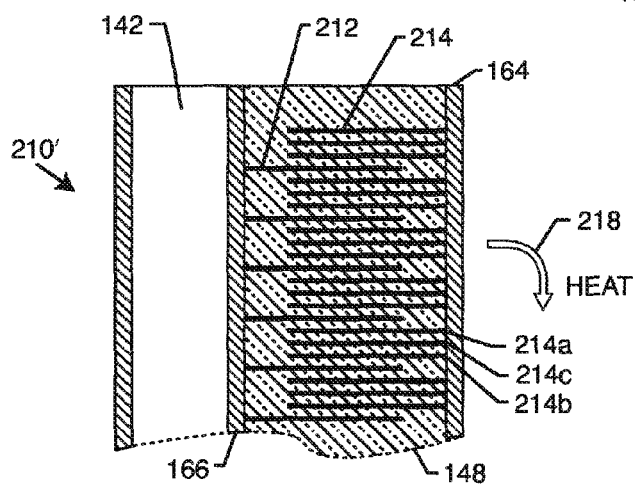
FIG. 44 is similar to FIG. 43 except that 3 or even "n" ground electrode plates are illustrated.

FIG. 44 is very similar to FIG. 43 except in this case, three ground electrode plates 214 are shown. In this case, the third electrode plate 214c (the one sandwiched between the upper 214a and lower 214b) would not conduct electrode displacement currents since it's shielded and exposed to the electric fields of the capacitor. However, in some embodiments, this could be a useful structure to conduct additional heat 218 away from the capacitor's internal structure. It will be obvious to those skilled in the art that any number of ground electrode plates, including "n" electrode plates could be used.

Figure 45:
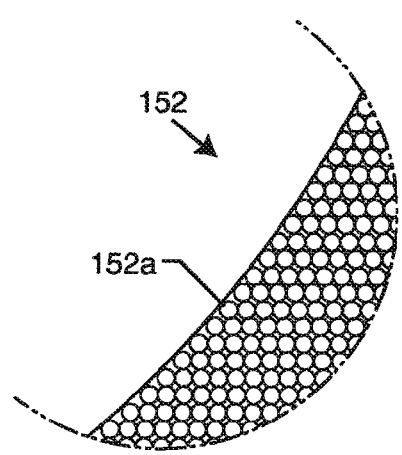
FIG. 45 is a partial section taken from section 45-45 from FIG. 41 illustrating conductive spheres in a thermal-setting conductive adhesive.

FIG. 45 is a sectional view taken from section 45-45 from FIG. 41. It shows an enlarged cross-section of the thermal-setting conductive adhesive attachment material 152 that connects the capacitor external metallization 164 to the gold braze surface 158 and the ferrule 134. In this case, the conductive adhesive 152 filler material consists of round conductive spheroids 152a. Also in this case, the spheroids 152a are all relatively the same size. This is typical of some silver-filled conductive epoxies. However, this is a very inefficient arrangement for thermal-conductivity. The spheroid conductor particles 152a make contact at their tangent points only. In this regard, FIG. 45 is not a particularly preferred embodiment.

Figure 46:
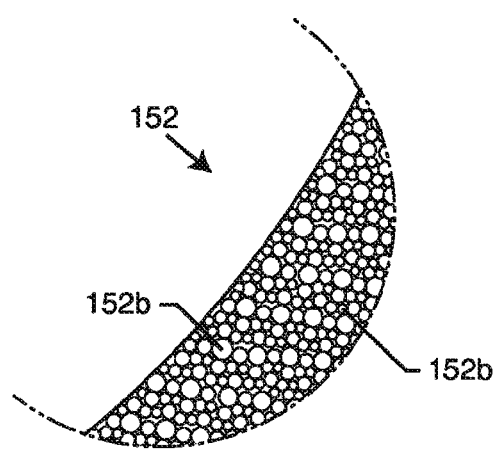
FIG. 46 is similar to FIG. 45 illustrating that the conductive spheres are of varying diameters.

FIG. 46 is very similar to FIG. 45 and is taken from section 46-46 of FIG. 41 and shows that, in this case, the conductive particles 152b loaded in the thermal-setting conductive adhesive 152 are of various diameters. This tends to pack the structure much more tightly (more contact points) in terms of thermal-conductivity and it's considered an improved embodiment in accordance with the present invention.

Figure 47:
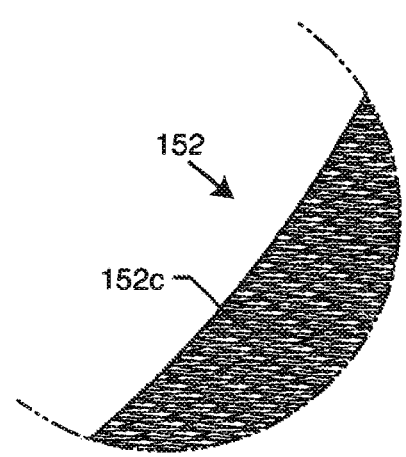
FIG. 47 is similar to FIGS. 45 and 46 except that the conductive spheres have been replaced by overlaying conductive flakes.

FIG. 47 is taken from section 48-48 again of FIG. 41 and shows that silver flake or similar flake materials 152e are used instead of spheres. These tightly packed flakes 152c are a particularly preferred embodiment in that they have very low impedance and very high thermal-conductivity.

Figure 48:
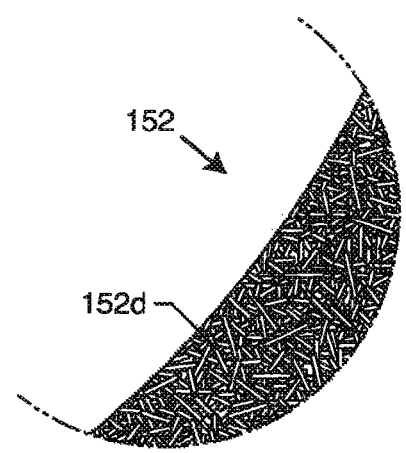
FIG. 48 is similar to FIGS. 45-47 except the conductive spheres have been replaced by conductive rods or similar structures.

Another particularly preferred embodiment is shown in FIG. 48 which is taken from section 48-48 of FIG. 41, which illustrates that the conductive fillers 152d can be rods, tubes, whiskers, fibers, nano particles, or other similar materials, alone or in combination, that aid efficient thermal transfer. The preferred embodiment leverages the filler content with the filler shape and/or type to achieve effective multiple point-to-point contact and/or anisotropic dispersions that facilitate the thermal conductivity.

Figure 49:
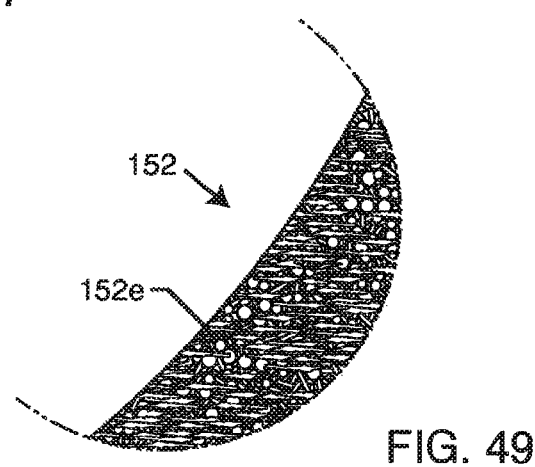
FIG. 49 indicates that the highly thermally-conductive matrix can be formed by combining the spheres of FIG. 46, the flakes of FIG. 47 and the rods of FIG. 48.

FIG. 49 illustrates that any mixture of spheres 152b as shown in FIG. 46, flakes 152c as shown in FIG. 47, rods or tubes 152d as shown in FIG. 48, can all be combined together 152e as shown in FIG. 49. These combinations can be optimized to elicit specific thermal conductivity rates, characteristics, and performance parameters.

As illustrated in FIGS. 46 through 49, these attachment materials 152 are both highly electrically conductive and are also highly thermally-conductive. It is a principle of the present invention that, in a preferred embodiment, the electrical attachment material 152 also has a thermal-conductivity at 37° C. that is less than 45 watts per millikelvin. Ceramic filler materials can also be used to aid in thermal-conductivity. However, the problem with this is that adding non-conductive fillers generally decreases the electrical conductivity. Referring back to FIG. 39, the highly thermally-conductive overlay material 216 could be filled with highly thermally-conductive substances, such as ceramics, including alumina nitride (AlN), beryllium oxide (BeO) and the like. All of these materials at 37° C. have thermal conductivities greater than 40 watts per millikelvin. For example, beryllium oxide has over 200 watts per millikelvin of thermal-conductivity at body temperature.

Figure 50:
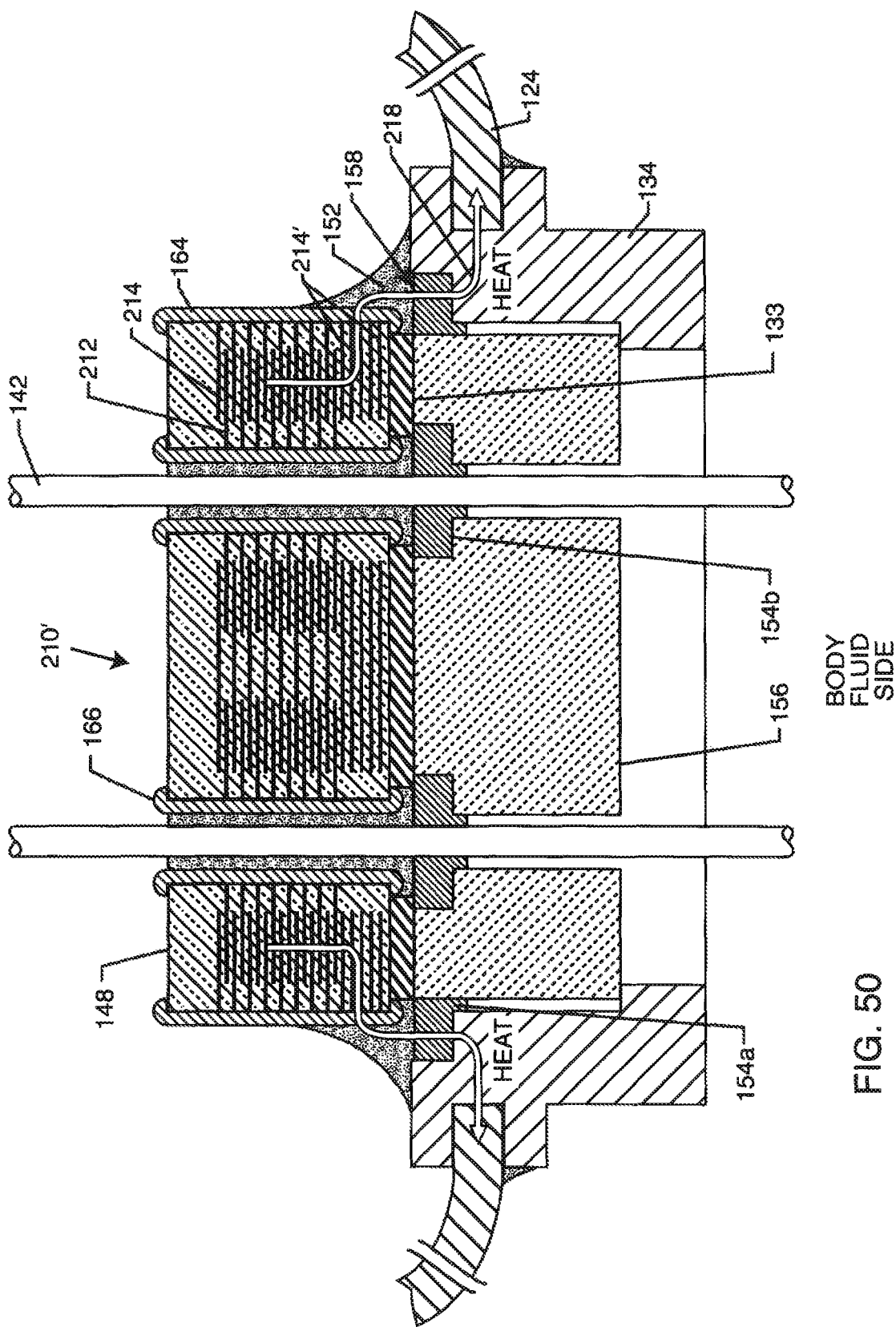
FIG. 50 is similar to FIG. 41 except that extra ground electrode plates have been added to the bottom of the capacitor to facilitate additional heat transfer out of the capacitor through the ferrule and into the AIMD housing.

FIG. 50 is very similar to the cross-section of the quad polar capacitor previously described in FIGS. 15 and 41. Again, the number of electrode plates 212 and 214 have been increased in accordance with the present invention such that the FIG. 50 quad polar diverter capacitor 210' has an ESR 198 generally less than 2 ohms. Referring once again to FIG. 50, one can see that the capacitor metallization 164 is attached using a conductive material 152 to a gold surface 158. All of these connections, when properly done, have negligible resistance. Accordingly, the capacitor's ESR 198, at high frequency, is made up of the resistance of the ground electrode plates 214 and active electrode plates 212 all acting in parallel. Referring once again to FIG. 50, one can see that a number of additional ground electrode plates 214' have been added at the bottom of the capacitor 210' near the interface with the capacitor 210' and the hermetic seal ferrule 134. These additional ground electrode plates 214' are not intended to affect the capacitance of the diverter capacitor 210'. These additional ground electrode plates 214' greatly assist in the overall thermal-conductivity of the diverter capacitor 210' thereby diverting heat 218 from the interior of the capacitor 210' through the electrical attachment material 152 (and any supplemental thermally-conductive overlay 216, not shown in this drawing) to the ferrule and in turn to the housing 124 of the AIMD 100. The addition of these added ground plates 214' is a novel feature of the present invention, which greatly increases the thermal-conductivity of the filtered diverter capacitor 210'. As previously stated, for EIA Class I dielectrics, the capacitor's dielectric loss 192 is negligible at MRI RF pulsed frequencies.

Figure 51:
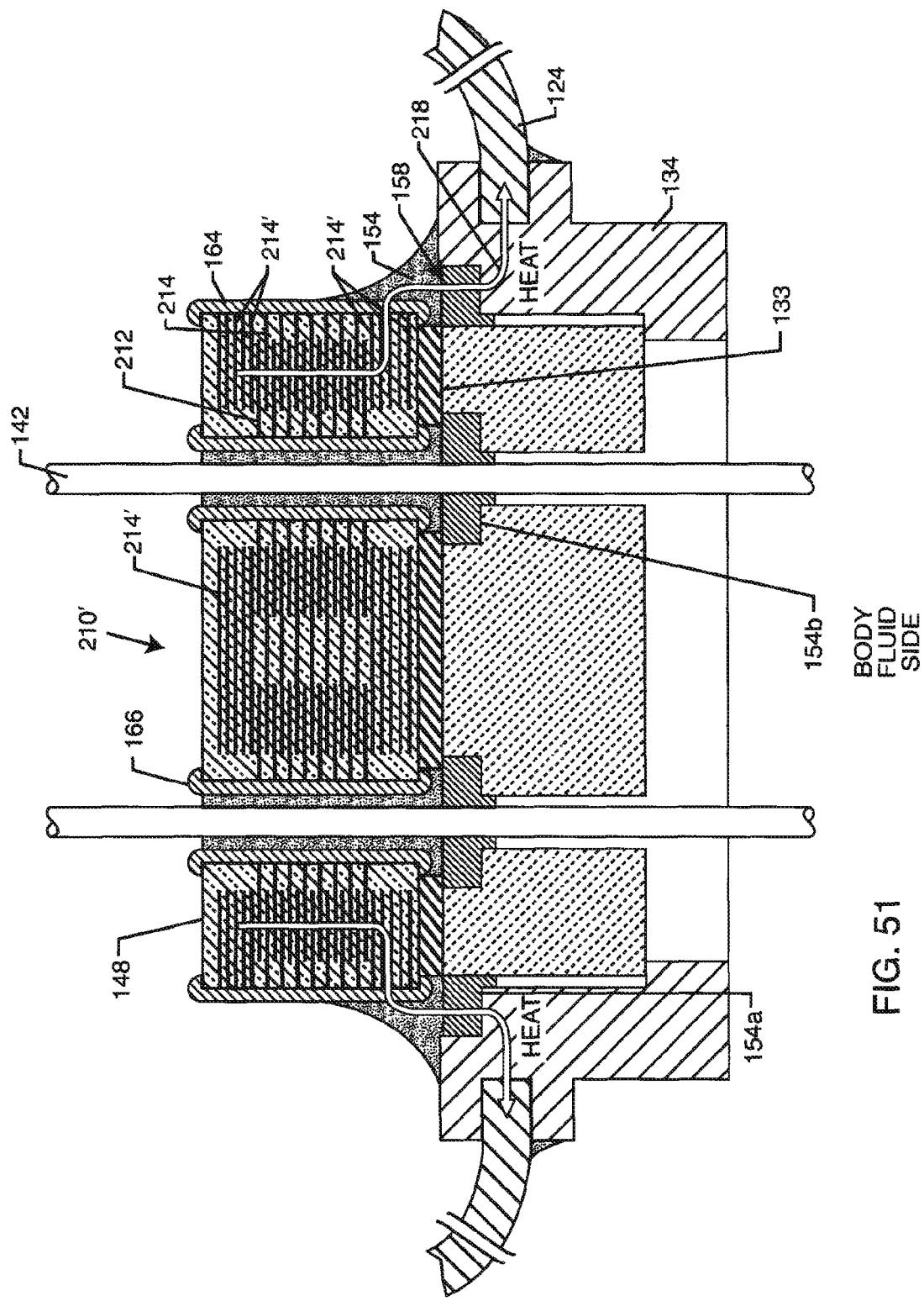
FIG. 51 is similar to FIG. 41 except that extra ground electrode plates have been added to the top and bottom of the capacitor to facilitate additional heat conduction out of the capacitor through the ferrule and into the AIMD housing.

FIG. 51 is very similar to FIG. 50 except that additional ground electrode plates 214' have been added to both the top and the bottom of the capacitor 210' to assist with conductive heat flow 218.

Figure 52:
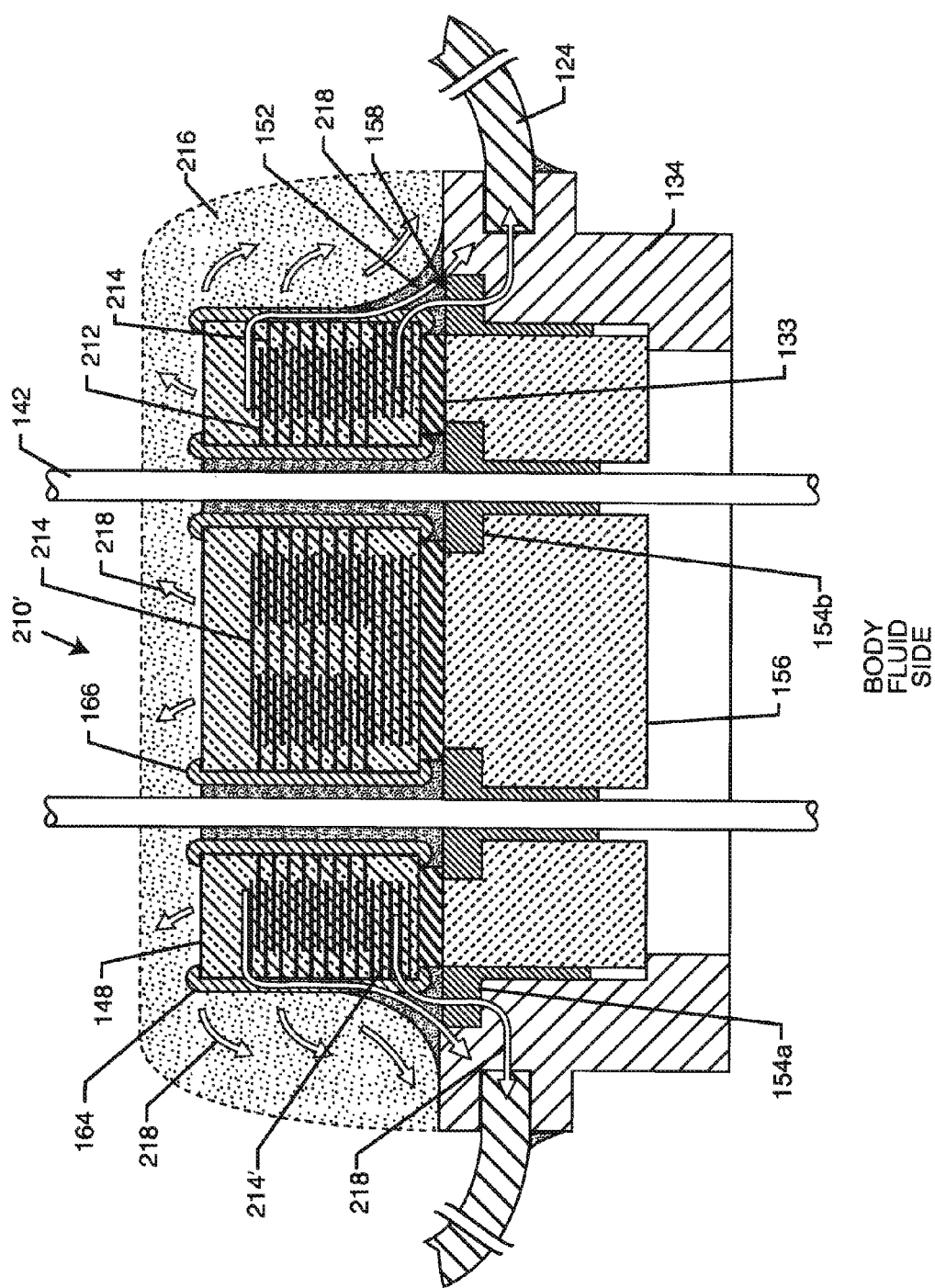
FIG. 52 is similar to FIG. 50 except that additional ground plates have been added to both the bottom and top of the capacitor to facilitate additional heat transfer. Also shown is an optional highly thermally-conductive overlay or adhesive.

FIG. 52 is also very similar to the cross-section of the quad polar capacitor previously described in FIGS. 50 and 51. Again, the number of electrode plates 212, 214 have been increased in accordance with the present invention such that the FIG. 52 quadpolar diverter capacitor 210' has an ESR 198 generally less than 2 ohms. Referring once again to FIG. 52, one can see that a thermally-conductive overlay 216 has been added over the top of the feedthrough diverter capacitor 210' which provides additional thermally-conductive paths 218 off the top of the capacitor, down along its sides and turn to the ferrule 134 and in turn to the conductive housing 124 of the AIMD. One can see the multiple 218 path arrows illustrating conductive heat flow away from the dielectric material 148.

Figure 53:
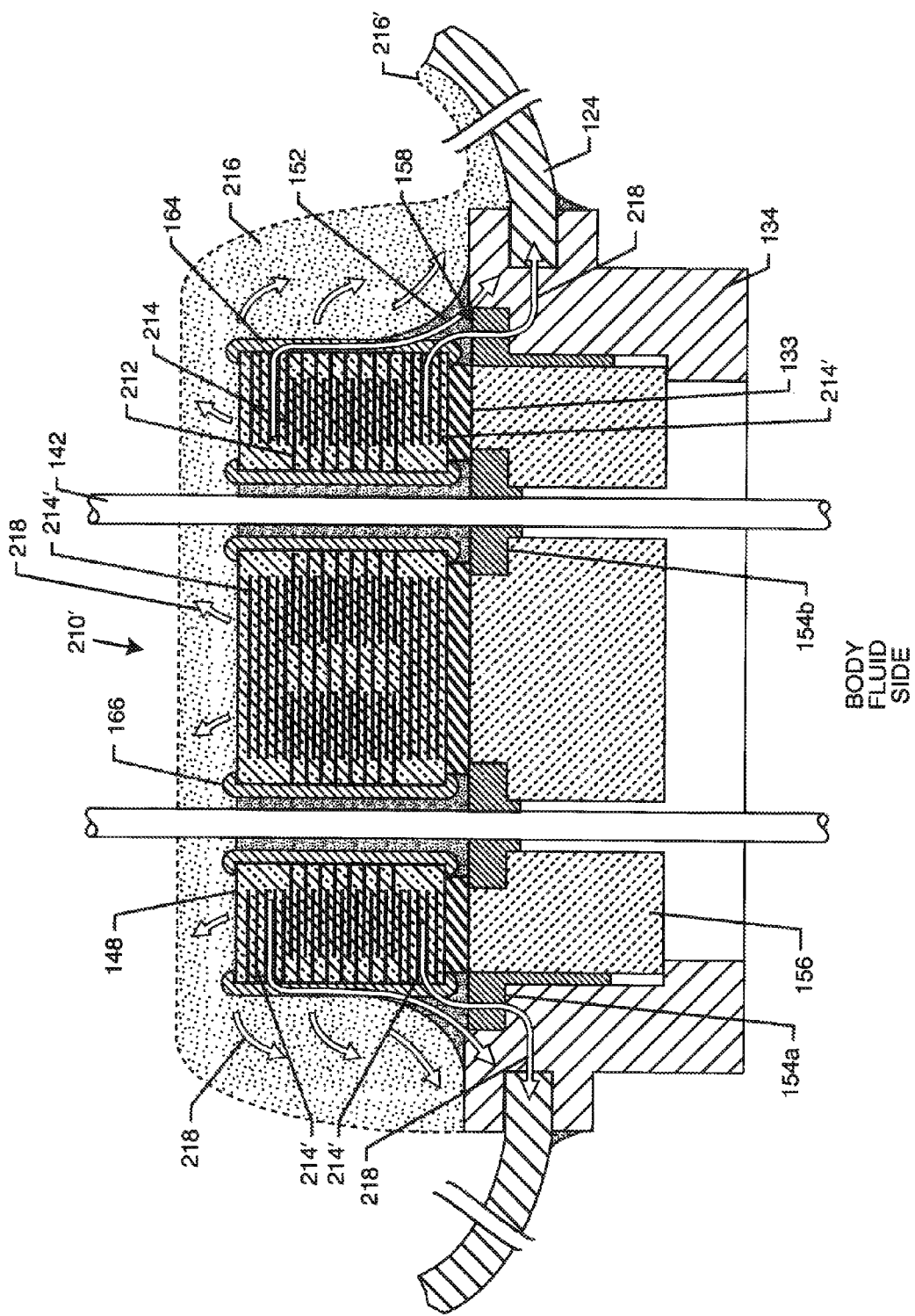
FIG. 53 is similar to FIG. 52 except that the thermally-conductive over-coating material has been extended to coat over the ferrule and a portion of the inside of the AIMD housing.

FIG. 53 illustrates an embodiment in which highly thermally-conductive material 216, 216' not only overlays the entire capacitor 210', but also extends across a portion of the inside surfaces of the AIMD housing 124. This assists in thermal-conductivity to dissipate the heat 218 out over a larger surface area of the AIMD housing 124.

FIG. 54 is very similar to FIG. 52 except that ground electrode plates 214" have been added inside of the hermetic insulator 156. These additional ground plates 214" provide added thermal conductive paths which assist in conducting heat out of the structure to the ferrule 134 and in turn to the AIMD housing 124. In addition, these conductive ground plates 214" also form a parasitic capacitance 220 between the leads 142 and the electrode plates 214" which forms an additional capacitance. This is a low value of capacitance, but is important in diverting additional high frequency energy away from the leads 142 to the housing 124 of the AIMD 100.

FIG. 55 is a sectional view taken generally from section 55-55 from FIG. 54. This shows a close-up view of the parasitic capacitance 220 which provides the additional high frequency filtering.

Figure 56:
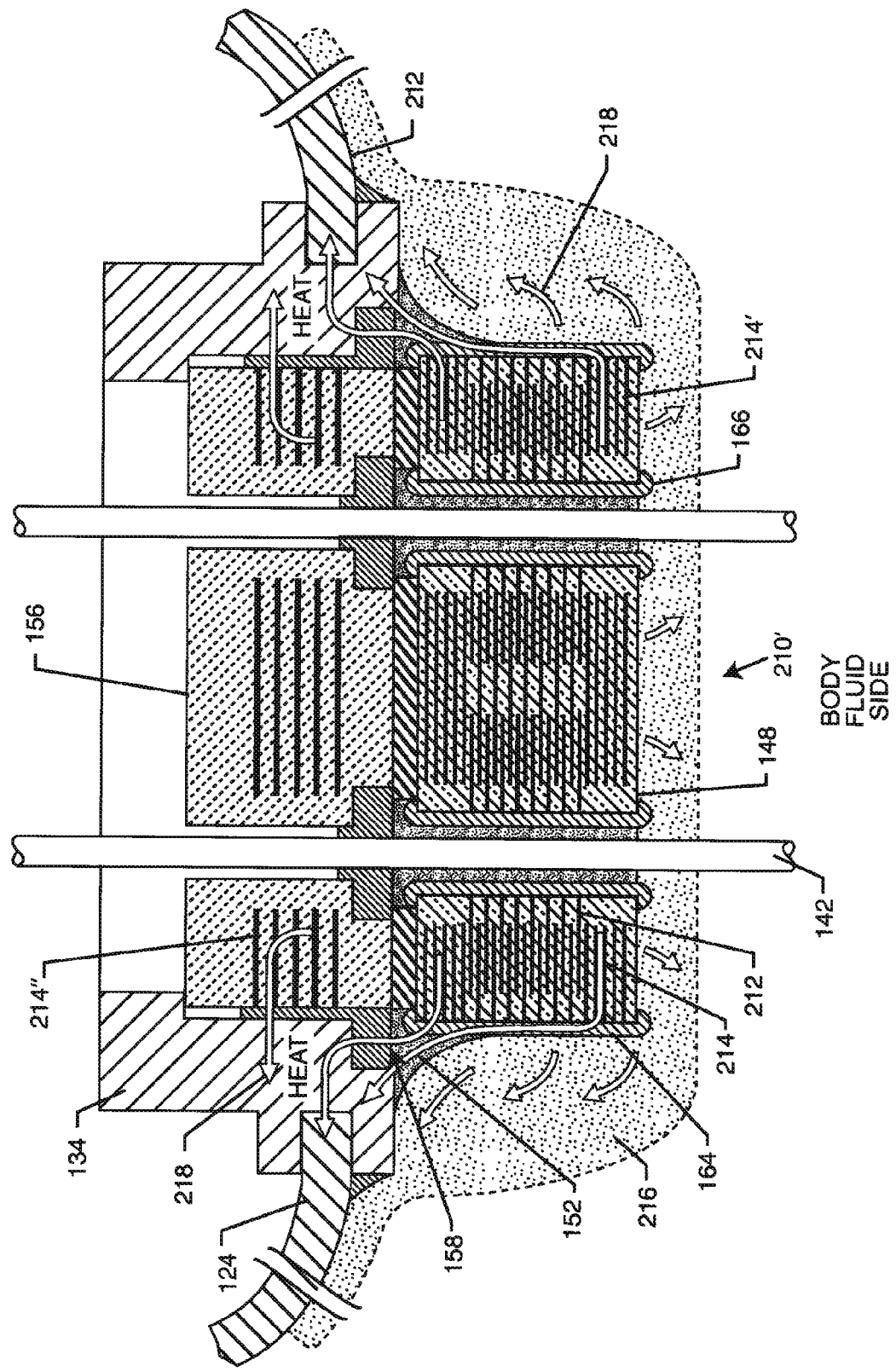
FIG. 56 is similar to FIG. 54 except that in this case the diverter capacitor 140 is disposed on the body fluid side where it is covered with a highly thermally-conductive material.

FIG. 56 illustrates an embodiment in which the diverter capacitor 210' has been moved (flipped over) to the body fluid side. The advantage to this is that the capacitor completely exposed so that a highly thermally-conductive sealant or overlay 216 can be placed completely over and around capacitor 210' and then extend onto the ferrule 134 and across all or a portion of the AIMD housing 124. This highly thermally-conductive layer 216 greatly assists in conducting heat 218 out of the capacitor 210' structure as shown by the high number of heat flow arrows 218. In the case where the diverter capacitor 210' is disposed towards the body fluid side, it is very important that it be constructed entirely of non-toxic and biocompatible materials. EMI filter capacitors designed for direct body fluid exposure are described in U.S. Pat. No. 7,535,693, the contents of which are incorporated herein by reference.

Figure 57:
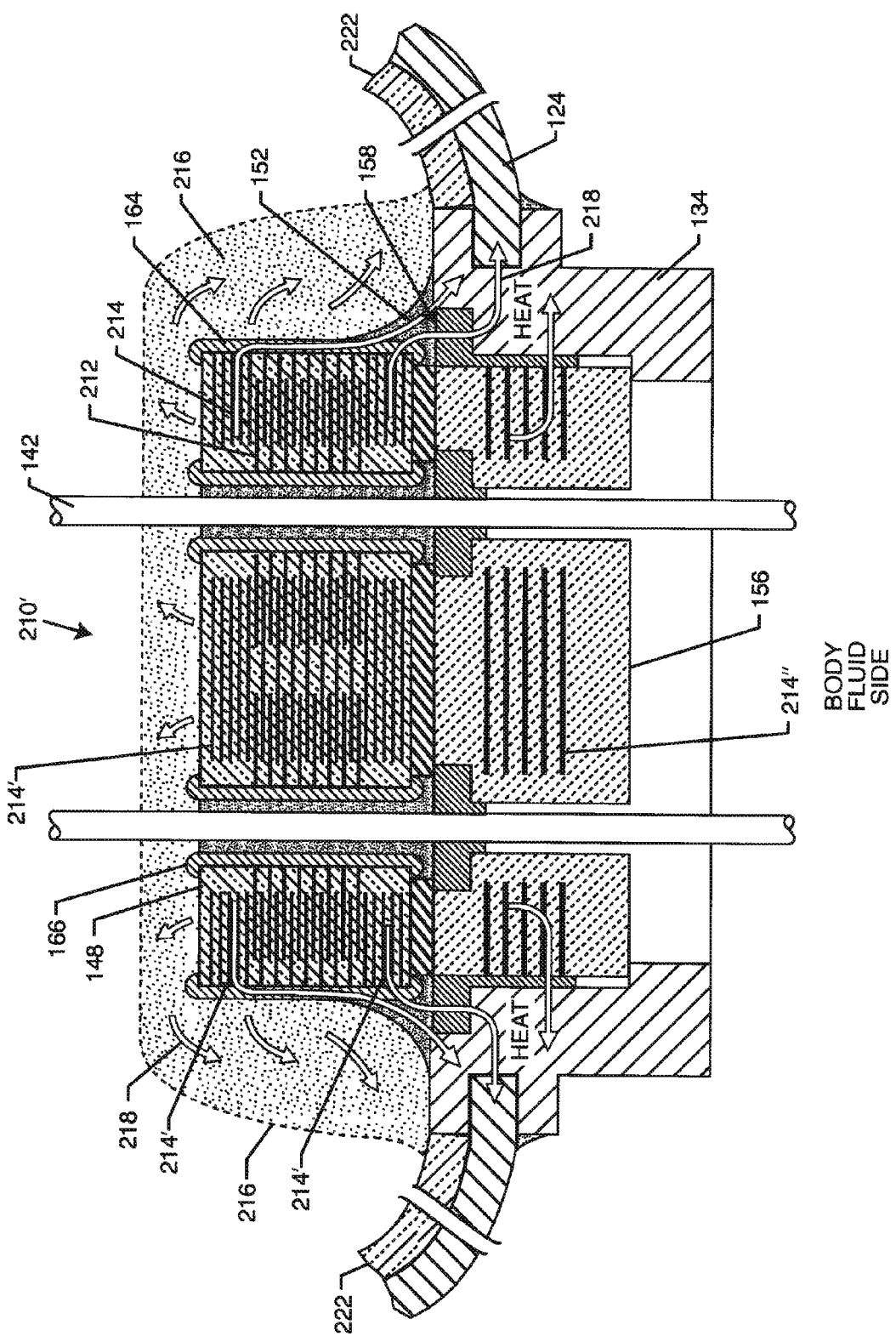
FIG. 57 is similar to FIG. 53 except that a highly thermally conductive liner has been added on the inside of the AIMD housing to further facilitate heat flow away from the capacitor.

FIG. 57 illustrates an embodiment in which a highly thermally-conductive liner 222 has been added to the inside surfaces of the AIMD housing 124. This highly thermally-conductive liner 222 is preferably in connection with the thermally-conductive capacitor overlay material 216. This system greatly aids in heat conduction and heat dissipation over a larger surface area of the AIMD housing 124. Options for high thermal conductivity materials 216, 222 may be used as pure materials or alloys and may include but are not limited to Aluminum, Aluminum Nitride, Beryllium, Copper, Multi-walled Carbon Nanotube, Isotropically Enriched Diamond, Graphene, Gold, Silver, Platinum, or other materials with thermal conductivity greater than 150 watts per meter Kelvin near 300K. These materials may be used as discrete components to create heat sinking features or as additives to thermoset or thermoplastic resin systems which can be dispensed to an energy dissipating surface within the AIMD. Referring once again to FIG. 57, one can see that additional ground plates 214' have been added to the top and the bottom of the diverter capacitor structure 210'. This assists in conductive heat flow as shown out through the top and bottom of the capacitor into the surrounding materials.

Figure 58:
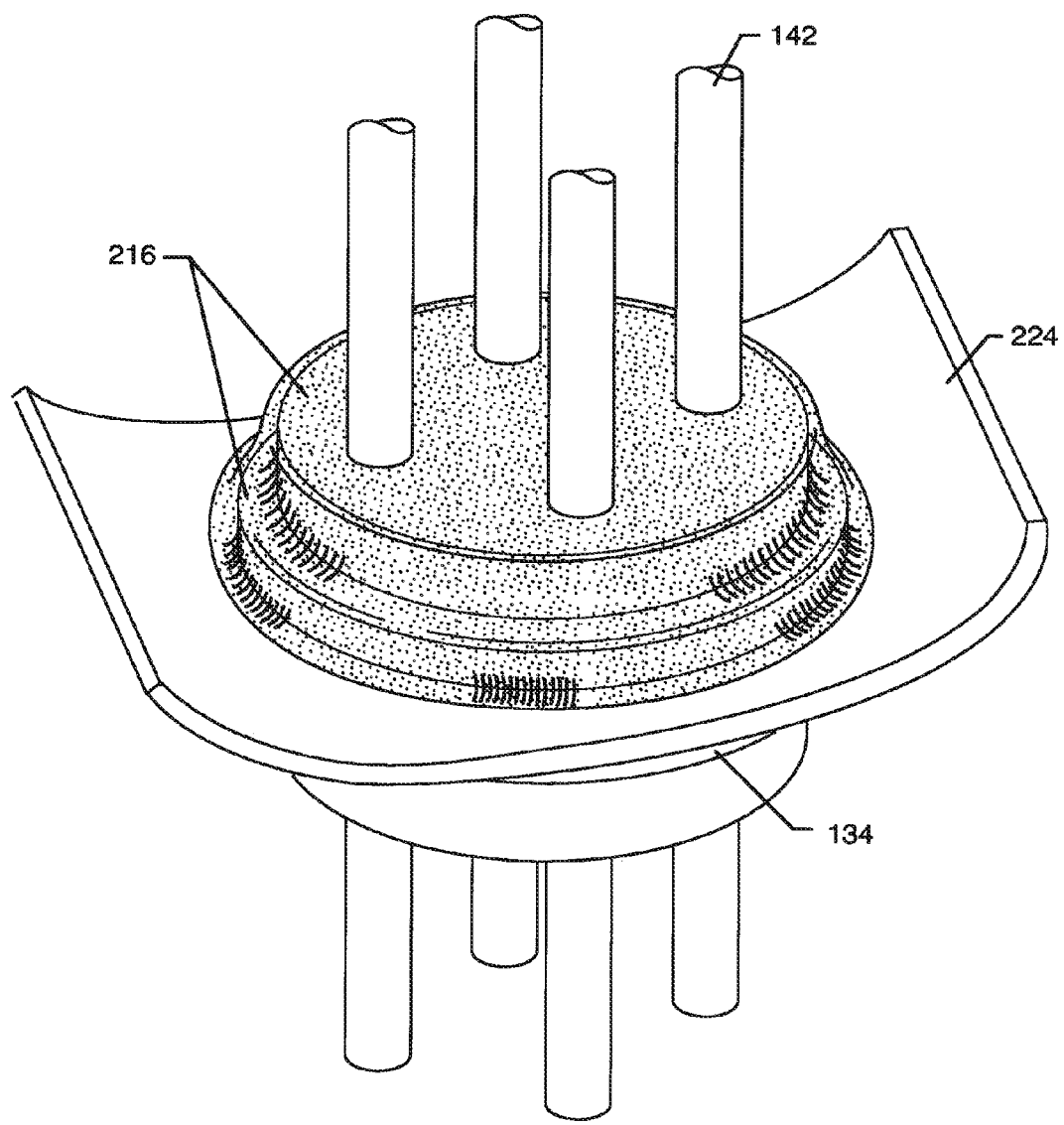
FIG. 58 is very similar to FIG. 57 except that a weld shield has been added which assists in thermal conductance away from the capacitor.

FIG. 58 illustrates an embodiment in which a weld shield 224 has been added. This Weld shield 224 is generally positioned such that it is tack welded to the ferrule of the hermetic seal 132. As shown, the clam shells of the AIMD housing 124 come together and capture the weld shield 224 and the diverter capacitor 210'. The advantage of the weld shield 224, in this case, is very similar to what was described in the previous embodiment in which the capacitor 210' is positioned on the body fluid side. This allows a highly thermally-conductive material 216 to be placed completely over the capacitor and down over the ferrule 134 and onto the weld shield 224 as shown.

Figure 59:
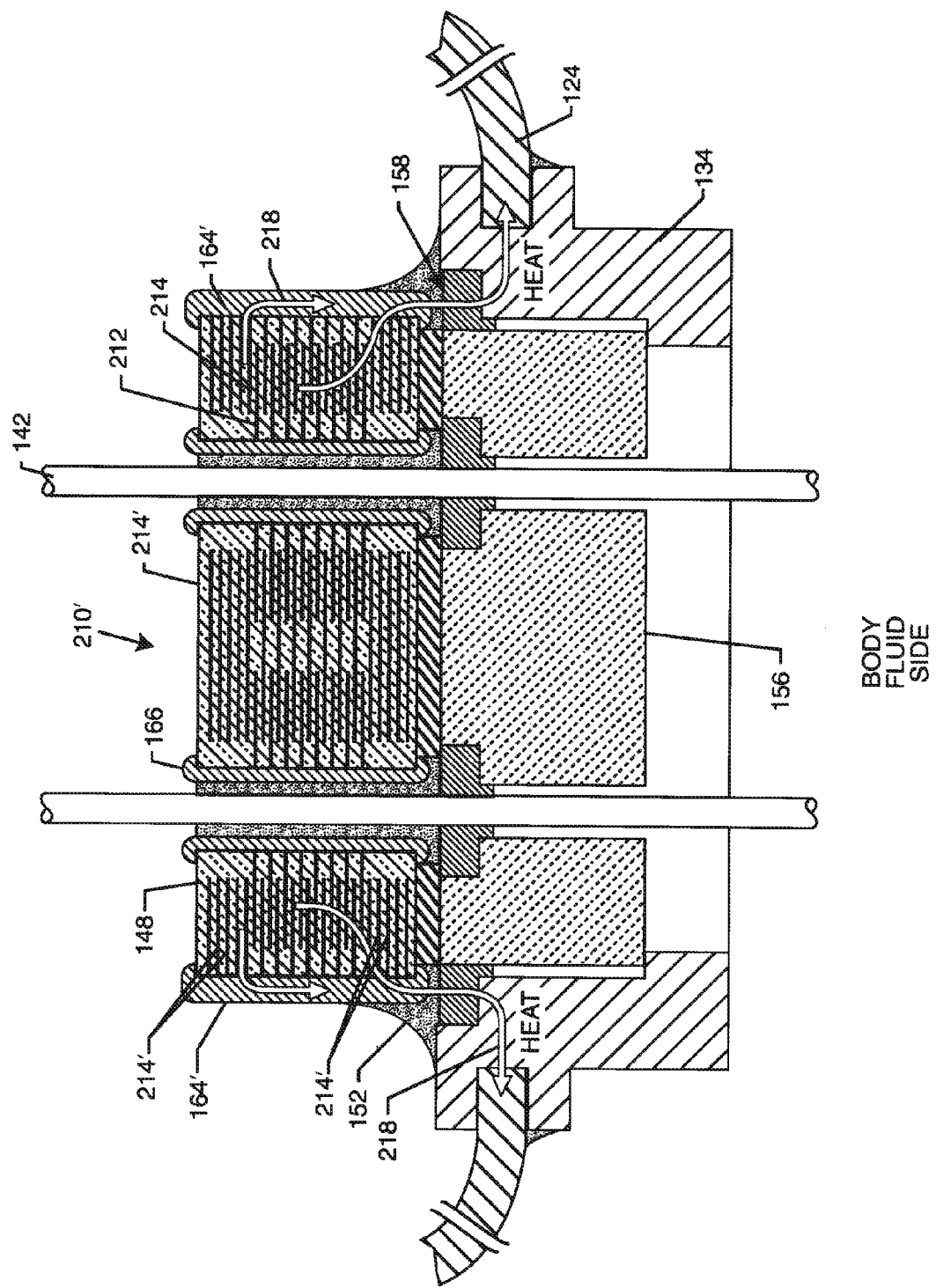
FIG. 59 is similar to FIG. 57 except that the capacitor perimeter metallization has been increased in thickness.

FIG. 59 illustrates a similar capacitor 210' with additional top and bottom electrode plates 214' wherein the capacitor's outside diameter and perimeter metallization 164' has been thickened. In addition, it is made of highly thermally-conductive materials. Options for high thermal conductivity capacitor 210' metallization 164' materials may be used as pure materials or alloys and may include but are not limited to Aluminum, Aluminum Nitride, Beryllium, Copper, Multiwalled Carbon Nanotube, Isotropically Enriched Diamond, Graphene, Gold, Silver, Platinum, or other materials with thermal conductivity greater than 150 watts per meter Kelvin near 300K. These materials may be used as discrete components to create heat sinking features or as additives to thermoset or thermoplastic resin systems which can be dispensed to an EDS within the AIMD. The increased thickness and increased thermal-conductivity of the outside diameter or perimeter metallization 164' greatly assists in increasing the heat flow 218 out of the capacitor 210' down to the ferrule 134 and in turn to the AIMD housing 114.

Figure 60:
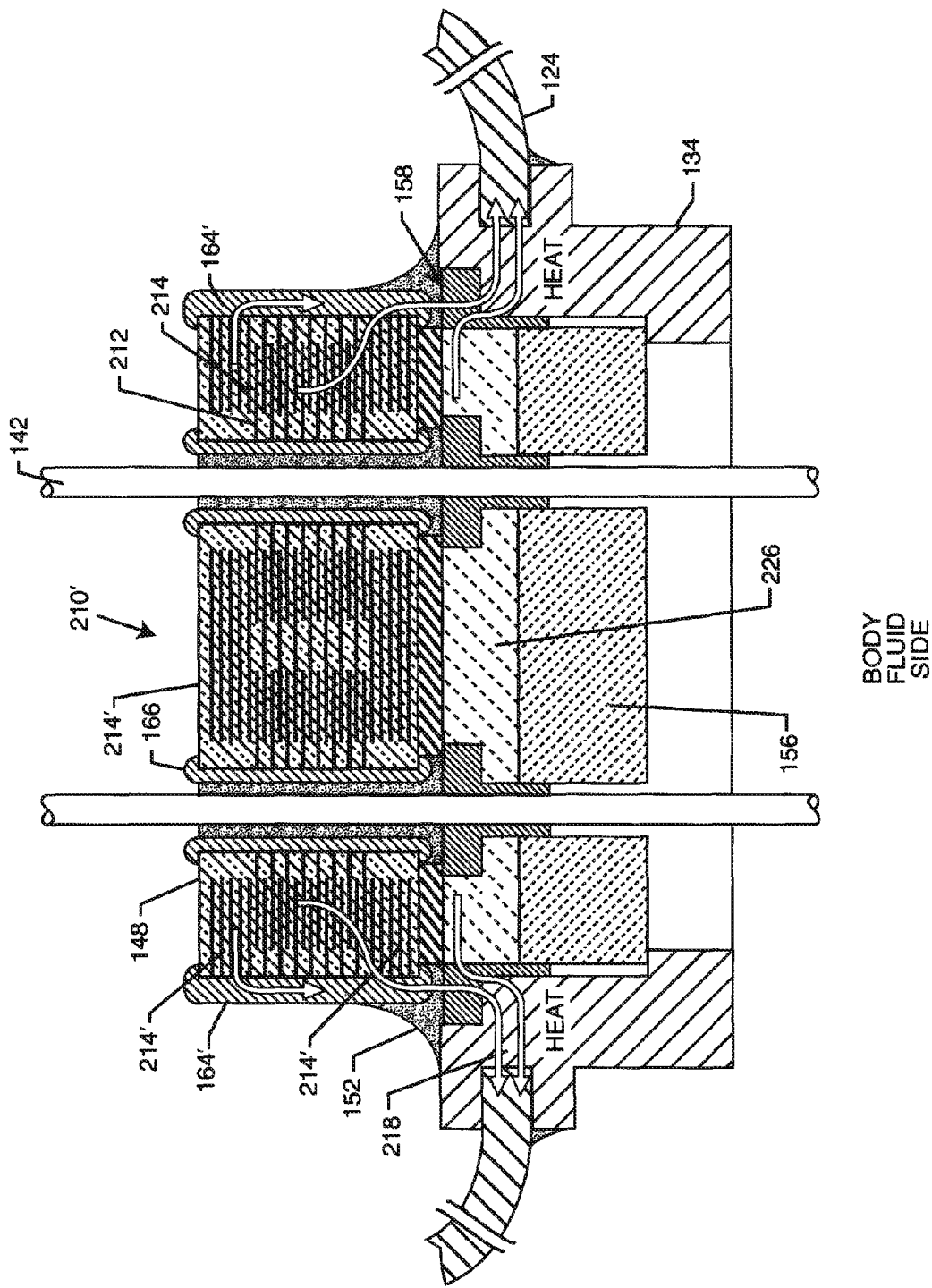
FIG. 60 is similar to FIG. 59 except that a highly thermally-conductive material has been co-bonded to the hermetic insulator.

FIG. 60 illustrates an embodiment in which the biocompatible alumina ceramic insulator 156 has a co-bonded or sintered layer of a highly thermally-conductive ceramic 226. As shown, this highly thermally-conductive layer 226 assists in conducting heat out of the diverter capacitor 210'-hermetic seal structure 134 to the AIMD housing 124.

Figure 61:
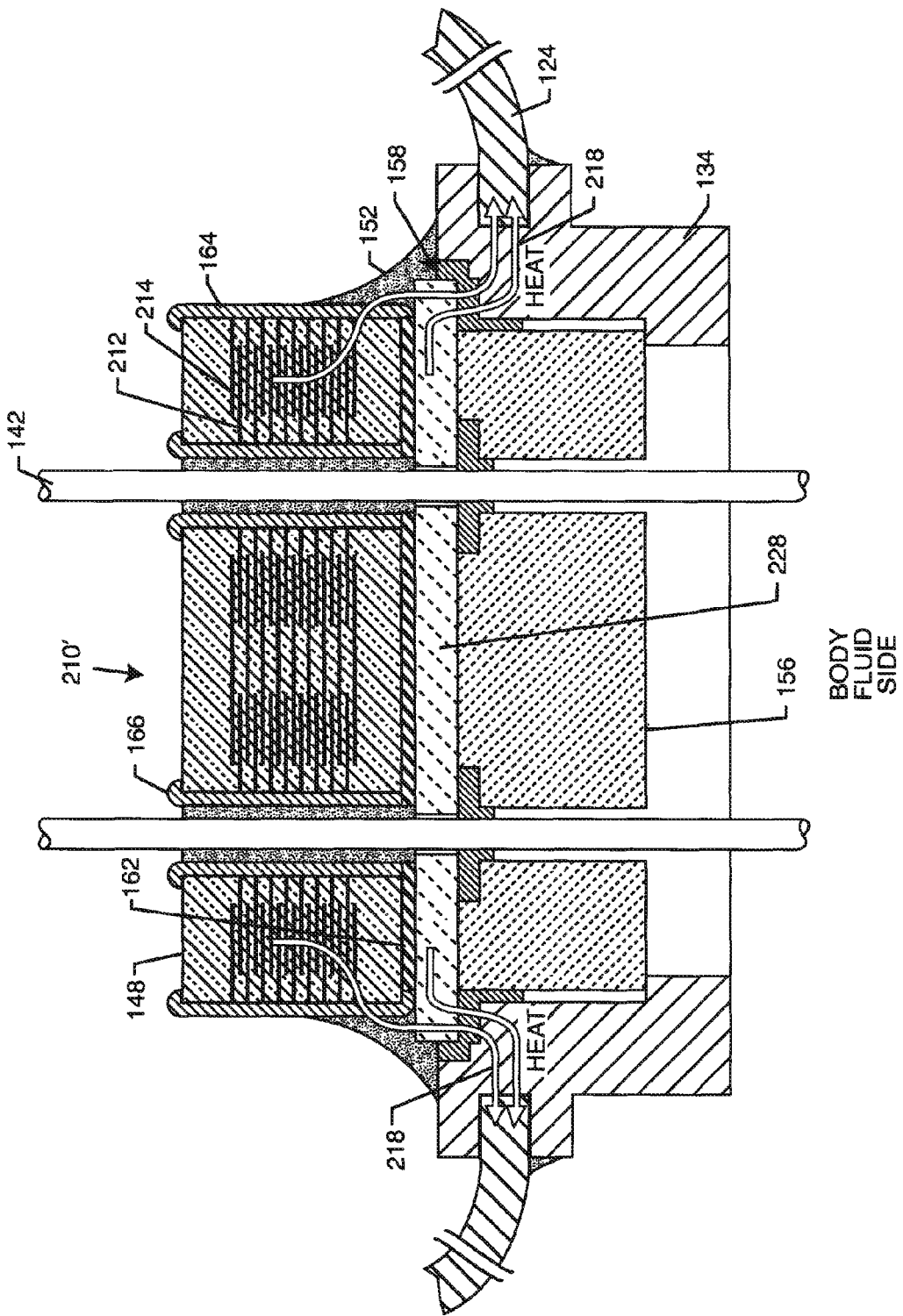
FIG. 61 is similar to FIG. 59 except that a highly thermally-conductive washer has been disposed between the capacitor and the hermetic insulator.

FIG. 61 illustrates an embodiment in which the upper and lower extra ground plates 214' have been removed and a highly thermally-conductive washer or layer 228 has been added that is disposed intermediate between the hermetic seal insulator 156 and the diverter capacitor 210' structure. Also shown is an optional insulation washer 162 used for bonding the capacitor 210' to layer 228. In a preferred embodiment, this adhesive insulation layer 162 would also be highly thermally conductive. Options for high thermal conductivity materials may be used as pure materials or alloys and may include but are not limited to Aluminum, Aluminum Nitride, Beryllium, Copper, Multiwalled Carbon Nanotube, Isotropically Enriched Diamond, Graphene, Gold, Silver, Platinum, or other materials with thermal conductivity greater than 150 watts per meter Kelvin near 300K. These materials may be used as discrete components to create heat sinking features or as additives to thermoset or thermoplastic resin systems which can be dispensed to an EDS within the AIMD.

Figure 62:
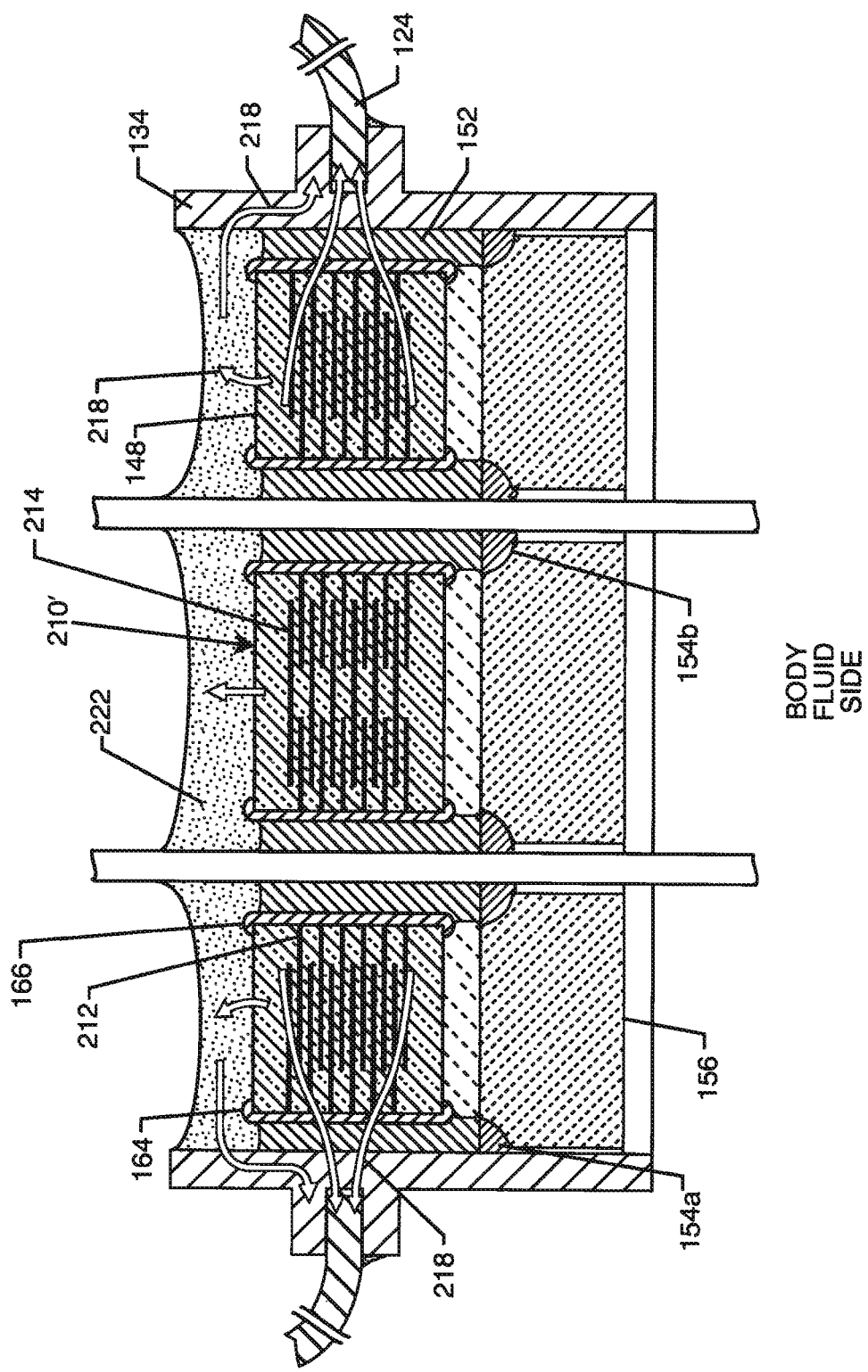
FIG. 62 illustrates the capacitor completely embedded and over-molded by a highly thermally-conductive material.

FIG. 62 illustrates a preferred embodiment wherein the diverter capacitor 210' is embedded completely down inside of ferrule 134. The entire structure is overlaid with a highly thermally-conductive material 222. As shown by the heat arrows 218, this greatly aids thermal conduction out of the diverter capacitor 210' through the ferrule 134 to the AIMD housing 124. Ina particularly preferred embodiment, the AIMD housing 124 is generally laser welded and connected somewhat along the midline of the diverter capacitor 210' to facilitate maximal heat conduction.

FIGS. 63 and 64 illustrate ceramic lowpass diverter capacitor 210' hermetic feedthrough assemblies 132 with a capture flange-style ferrule 134 coming part way up the outside diameter or perimeter of said capacitor 210' structure. This capture flange 230 provides a convenient space around the outside perimeter or circumference 164 of said capacitor whereby a robot or automatic dispensing system can dispense a thermalsetting conductive material 152 such as a conductive polyimide, solder paste, solder preform or braze preform. The capture flange 230 may be positioned higher up around the perimeter or outside diameter 164 of the diverter capacitor 210' as shown in FIG. 64. In this embodiment, one can greatly increase the heat flow 218 from the diverter capacitor 210' to the ferrule 134 and in turn to the AIMD housing 124.

Another embodiment shown in FIG. 65, illustrates the top view of the quadpolar capacitor shown in FIG. 64. In this embodiment, electrical connections 152 are positioned between the capacitor outside diameter metallization 164 and the ferrule 134. These electrical attachment areas 152 are not continuous. Preferably, these electrical attachment areas 152 are broken up by areas of attachment to a highly thermally-conductive material 232. This achieves a good balance between a low impedance and a low ohmic electrical connection and a highly thermally-conductive connection from the capacitor outside diameter 164 to the surrounding ferrule 134 and, in turn, to the AIMD housing 124. Options for high thermal conductivity materials 232 may be used as pure materials or alloys and may include but are not limited to Aluminum, Aluminum Nitride, Beryllium, Copper, Multiwalled Carbon Nanotube, isotropically Enriched Diamond, Graphene, Gold, Silver, Platinum, or other materials with thermal conductivity greater than 150 watts per meter Kelvin near 300K. These materials may be used as discrete components to create heat sinking features or as additives to thermoset or thermoplastic resin systems which can be dispensed to an EDS within the AIMD.

Figure 66:
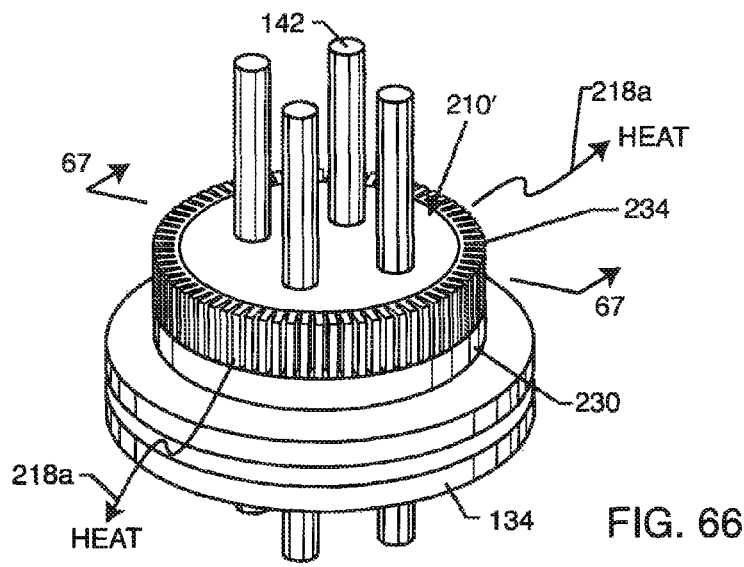
FIG. 66 is similar to FIG. 63 except that heat radiating fins have been added.

FIG. 66 is very similar to FIGS. 63 and 64 except that heat convection fins 234 have been added around the outside diameter metallization 164 of the capacitor 210'. It will be obvious to those skilled in the art that similar fins 234 could be added around a rectangular feedthrough diverter capacitor 140 as previously illustrated in FIG. 13. These fins 234 convect heat 218a into the interior of the AIMD 100, which in the prior art is generally back-filled with nitrogen, a combination of nitrogen and helium or even argon.

Figure 67:
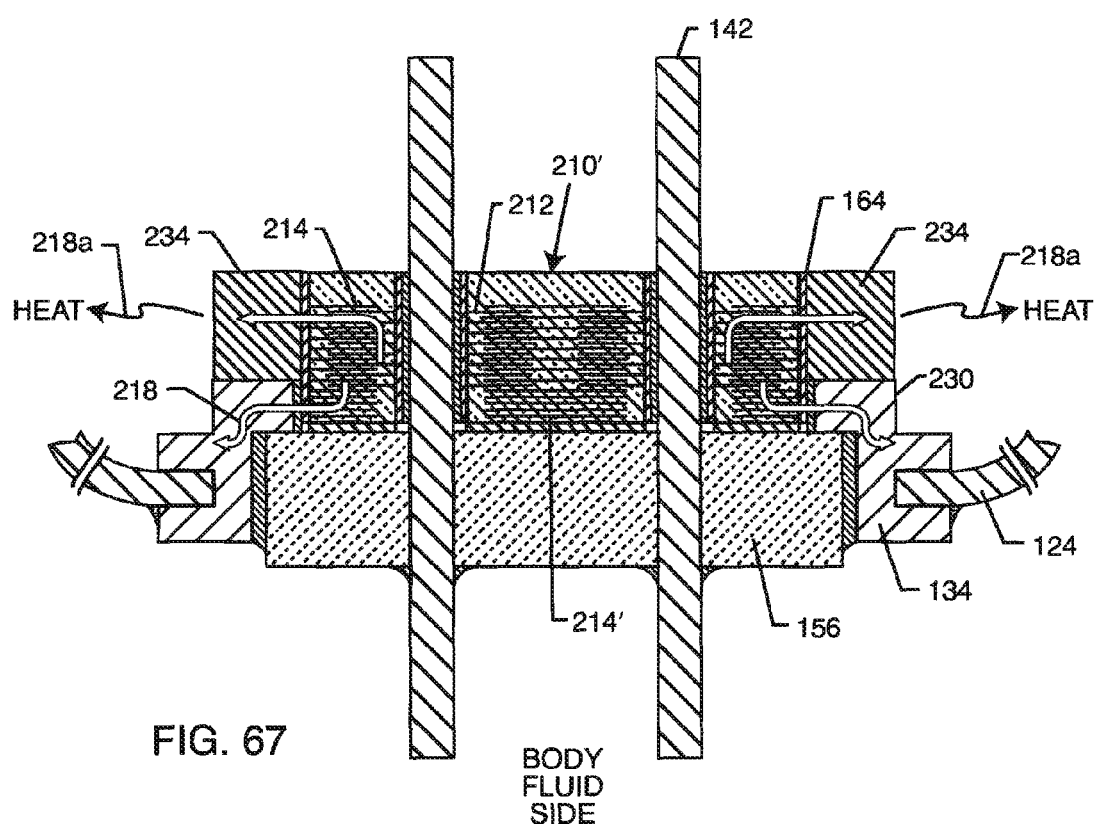
FIG. 67 is a sectional view taken from section 67-67 from FIG. 66.

FIG. 67 is a cross-sectional view taken generally from section 67-67 of FIG. 66. FIG. 67 illustrates the convective heat 218a that would radiate off the surface of the fins 234. In a preferred embodiment, the fins 234 would be constructed of a highly thermally-conductive material, such as aluminum in order to radiate and dissipate maximal heat 218a into the interior atmosphere of the AIMD housing 124.

Figure 68:
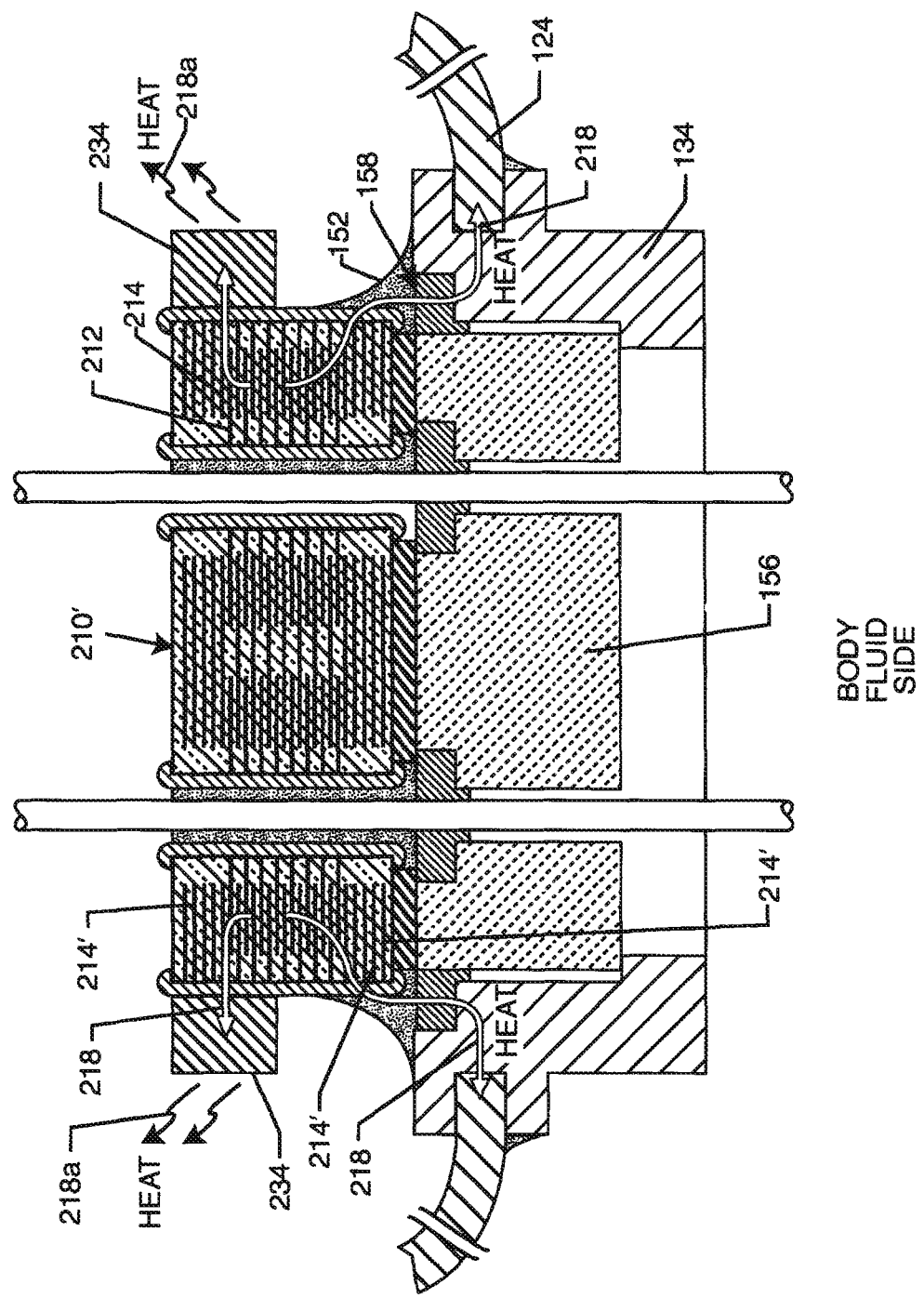
FIG. 68 is similar to FIG. 67 except that the heat radiating fins are disposed well above the ferrule.

FIG. 68 is very similar to FIG. 67 except that the heat convection fins 234 are associated with a hermetic seal ferrule 134 which does not have a capture flange. In this case, the heat conduction fins 234 are located above the surface of the ferrule 134. The heat conduction fins 234 perform the same heat convection purpose as previously illustrated in FIG. 67. Extra ground plates 214' co-operate with the fins 234 to transfer additional heat out of capacitor 210'.

Figure 69:
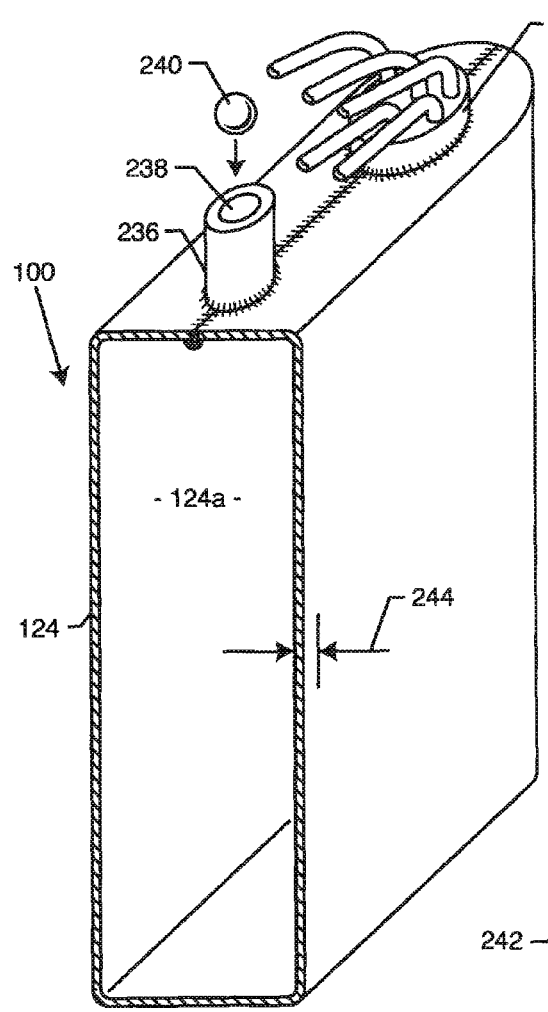
FIG. 69 illustrates a cutaway of an AIMD housing with a fill tube.
Figure 70:
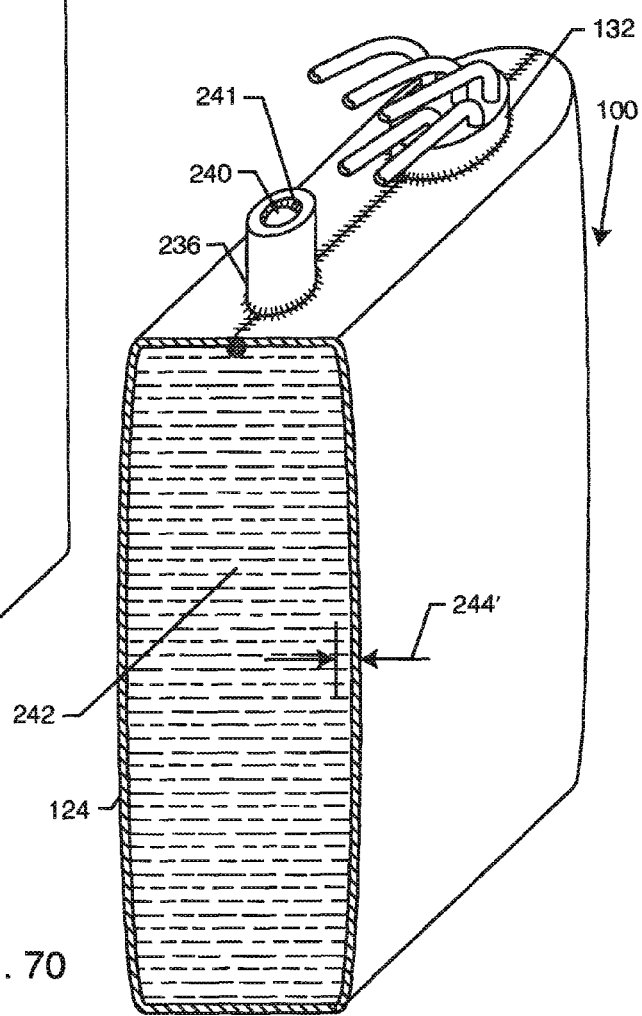
FIG. 70 is similar to FIG. 69 and illustrates the AIMD has been filled either with a high pressure gas or a liquid.

FIG. 69 illustrates a cross sectional view of an embodiment of an AIMD housing 124 comprising a hermetic seal subassembly 132, a fill tube 236 with a central opening 238 and a ball 240 welded, i.e., laser welded 241 therein. The AIMD of this embodiment facilitates back-filling of the inside 124a of the AIMD housing 124 with a liquid or dielectric gas 242 as illustrated in FIG. 70. Filling active implantable medical devices with a dielectric fluid 242 is more thoroughly described in U.S. Patent Publication No. 2009/0312835, the contents of which are incorporated by reference. This dielectric liquid 242 can also be a gas at an elevated pressure. Optionally, an elevated pressure gas fills the inside hermetically sealed area inside the AIMD housing 124. Referring again to FIG. 69, a vacuum is applied at an elevated temperature to the entire assembly to evacuate all moisture, air and other gas molecules from the inside of the AIMD housing 124. At this time, under hard vacuum, the vacuum is broken and a fluid 242 is flooded over the entire assembly. The fluid may include a liquid or a gas, such as a dielectric gas 242. Then a high pressure nitrogen is placed on top of the liquid, which impregnates the inside of the entire AIMD housing 124 with the liquid or gas. This is best illustrated in FIG. 70 wherein, the liquid or gas 242 fills every crevice in unoccupied space within the interior of the AIMD housing 124. In a preferred embodiment, the liquid or gas 242 is highly thermally-conductive such that it conducts heat away from the feedthrough capacitor (not shown), which is located directly underneath the hermetically sealed housing 132. In a particularly preferred embodiment, the diverter capacitor 210' has fins 234 as previously illustrated in FIG. 66. These fins 234 are designed to efficiently convect heat to the liquid or gas 242 that fills the entire inside spaces of the AIMD housing 124. In addition, the atmospheric pressure of a gas could be increased within an AIMD housing. Gases typically used to backfill AIMDs could be utilized to increase the atmospheric pressure within the device. For example, nitrogen could be used to pressurize the device. An increase of about two atmospheres would convect more heat away from the diverter capacitor 210'. As shown, in this case, the thin AIMD housing 124 would deflect slightly outward as shown in 244 and 244'.

Figure 71:
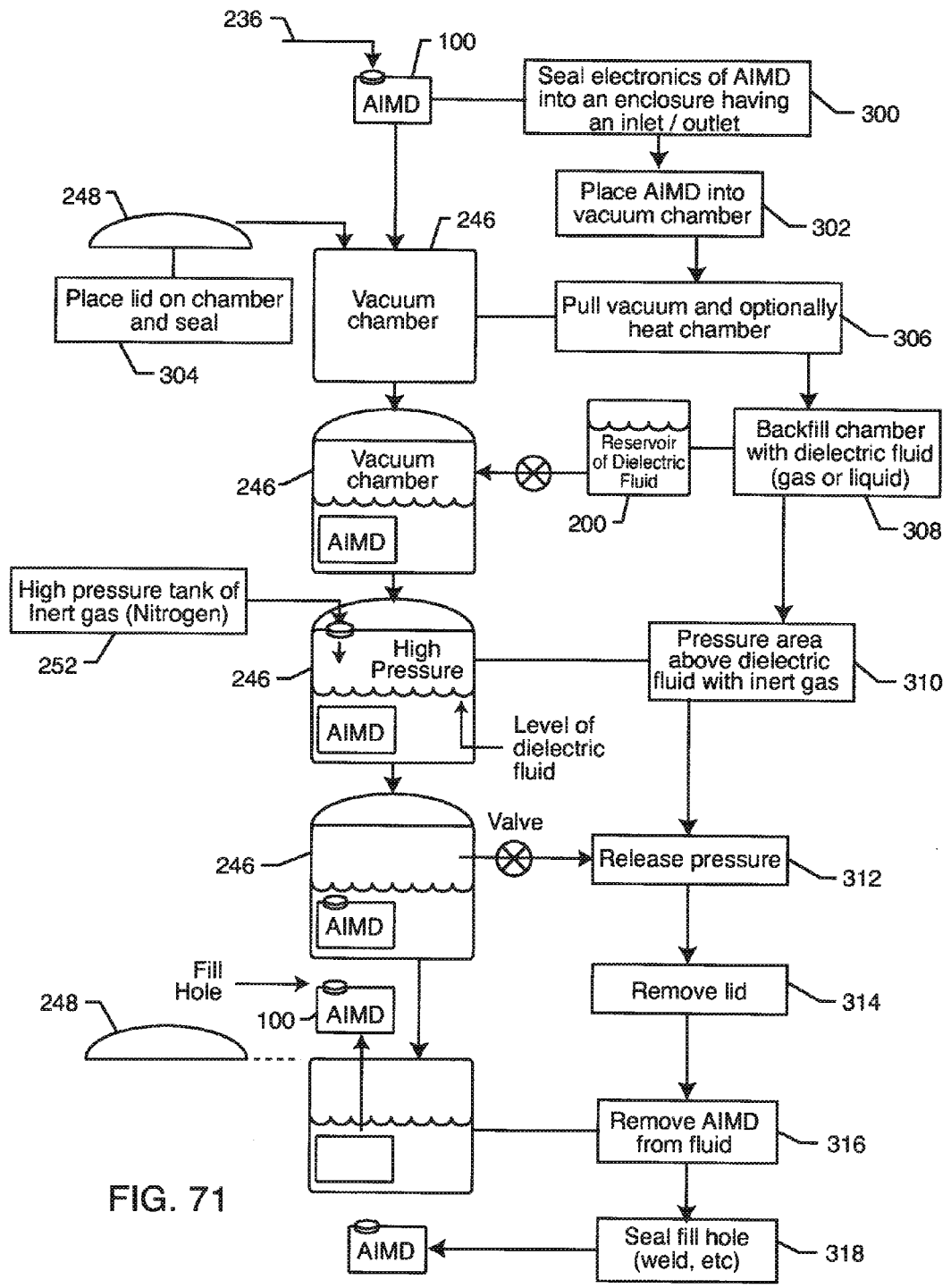
FIG. 71 is a flow chart of the process of FIGS. 69 and 70.

FIG. 71 is a flow chart illustrating the process as previously described in FIGS. 69 and 70. After the electronics of the AIMD are sealed in a housing 124 having an open fill tube 236, the first step 302 of the process is to place the AIMD 100 having an open fill tube 236 into a vacuum chamber 246. A lid 248 is placed and sealed 304 on the vacuum chamber 246 and a vacuum 306 is pulled for a number of hours on an AIMD. Optionally this process is performed at an elevated temperature. After a suitable time, under hard vacuum, a reservoir of dielectric fluid 250 is introduced and backfilled 308 into the chamber. Pressurized inert gas 252, such as nitrogen, is introduced 310 on top of the dielectric fluid. The inert gas 252 drives or impregnates the dielectric fluid into the interior spaces of the AIMD. Pressure is slowly released 312 and the lid 248 of the vacuum chamber 246 is removed 314. At this point, the ball 240 is inserted into a fill tube 236 or a similar fill hole is closed by laser welding 241 and the like, which hermetically seals the AIMD 100. At this time, the AIMD is removed 316 from the fluid or dielectric gas at which time the welding operation 318 is completed.

Figure 72:
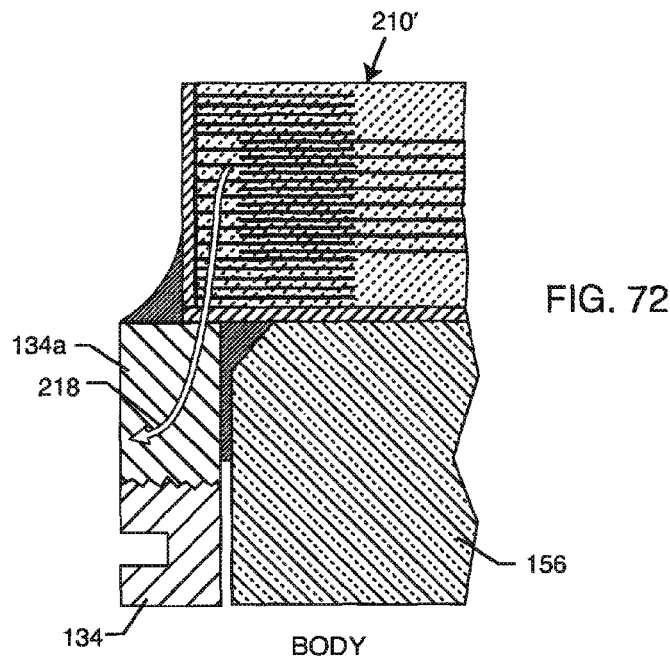
FIG. 72 illustrates using powder metallurgy or other techniques to add a highly thermally-conductive layer to the ferrule.

FIG. 72 is a cross-sectional view illustrating a diverter capacitor 210' attached to a hermetic seal assembly 132 comprising an insulator 156 and a ferrule 134a. In this case, ferrule 134a is a highly thermally-conductive metal, which has been co-bonded to a typical titanium ferrule 134. Ferrule 134a may be fabricated by a powder, metallurgy or metal pressing process or the like. The purpose here is to increase the heat flow out of the diverter capacitor 210' during exposure to a high power MRI RF field. The titanium ferrule 134 or other similar biocompatible material, is preferably directed toward the body fluid side. The biocompatible properties of the material enables the ferrule 134a to be exposed to body tissues for long periods of time.

Figure 73:
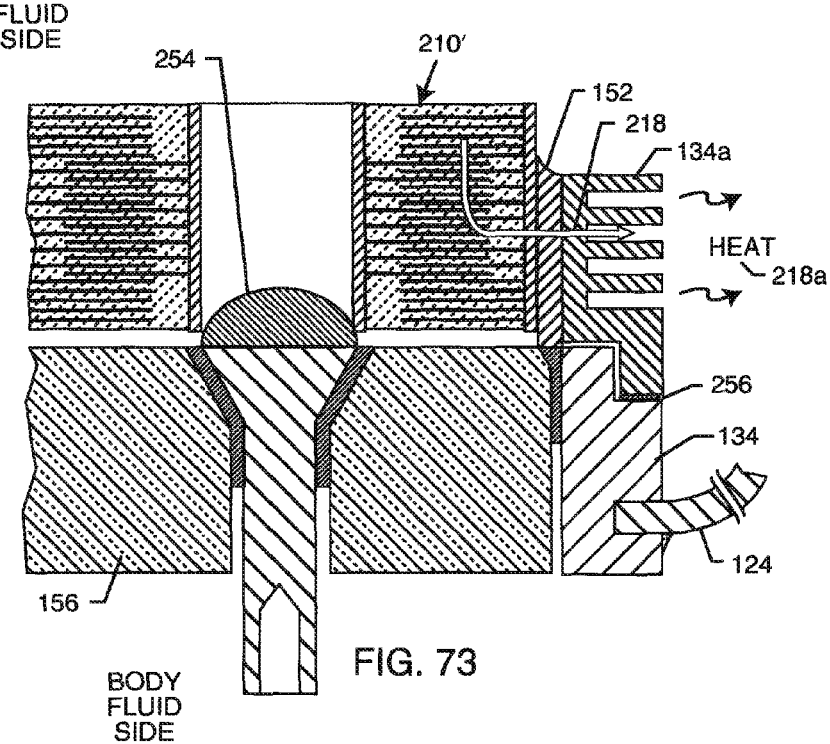
FIG. 73 is similar to FIG. 72 showing co-bonding a highly thermally-conductive material to the ferrule.

As shown in FIG. 73, the diverter capacitor 210' is designed for electrical attachment using a ball grid array (BGA) attached method. In this case, the hermetic seal insulator 156 has a crimp post with a pad for convenient BGA 254 mounting of the capacitor 210' as disclosed in U.S. provisional application Ser. Nos. 61/473,188; 61/587,029; 61/587,287 and 61/587,373, the contents of which are incorporated herein by reference.

FIG. 73 illustrates an embodiment in which two different ferrule structures 134 and 134a have been co-joined. Preferred joining processes include but are not limited to as brazing, laser welding 256 or similar attachment process. In accordance with the present invention, ferrule 134a comprises a highly thermally-conductive material designed to transfer heat energy out, of the diverter capacitor 210' into the interior of the AIMD housing 124. In a preferred embodiment, ferrule 134a comprises heat convection fins similar to those illustrated in FIG. 66.

Figure 74:
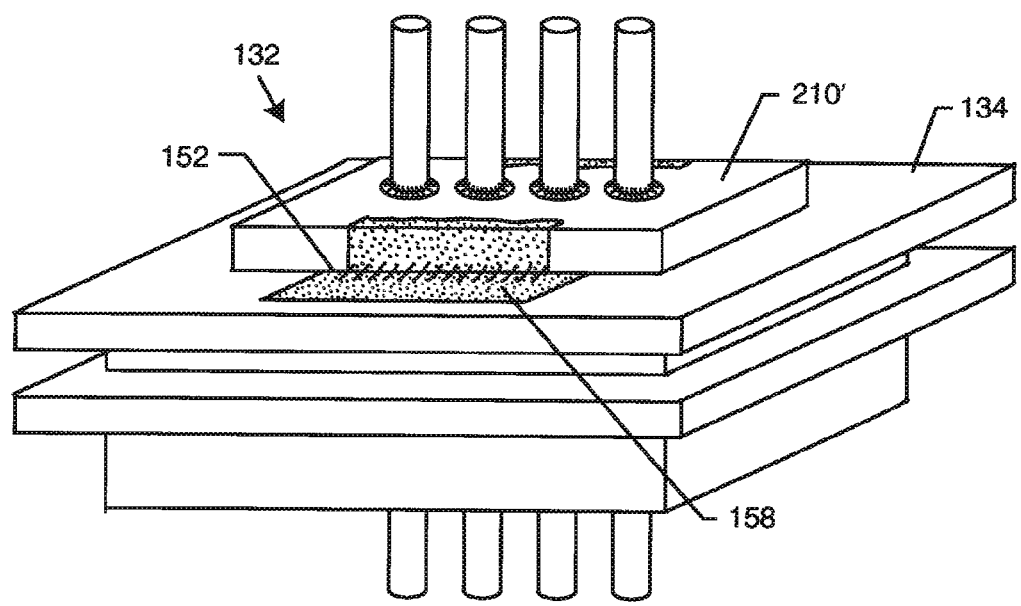
FIG. 74 is an inline quad polar capacitor similar to FIG. 13.

FIG. 74 illustrates an embodiment in which a quad polar diverter capacitor 210' of the present invention attached to the ferrule 134 of a hermetic seal assembly 132 of an AIMD.

FIGS. 75A and 75B illustrate embodiments of electrical attachment areas 152. As illustrated, the electrical attachment areas extend from the ground electrode plates 214 and/or the active electrode plates 212. In particular, the attachment 152 extending from the ground electrode plates 214 as shown in FIG. 75A resides over a relatively small attachment area and enables a relatively high frequency ESR.

FIGS. 76A and 76B illustrate embodiments in which the electrical attachment area 152 has been greatly increased. An increased electrical attachment area 152 improves the high frequency ESR of the inline quad polar feedthrough capacitor 210'. In terms of electrical attachment, a superior attachment 152 is shown in FIG. 77A where there is a 100% or full perimeter ground attachment to the capacitor ground electrode plate 214. However, this is not necessarily for the diverter capacitor 210' of the present invention to achieve optimal high RF power handling.

FIG. 78A illustrates a hybrid approach comprising an electrical attachment 152 and a highly thermally-conductive attachment 232. In this embodiment capacitor 210' has a relatively low ESR due to a good electrical attachment 152 plus a very highly efficient thermal transfer of heat energy out of the diverter capacitor. The transfer of thermal energy is achieved through the use of a thermally conductive adhesive 232.

Figure 79:
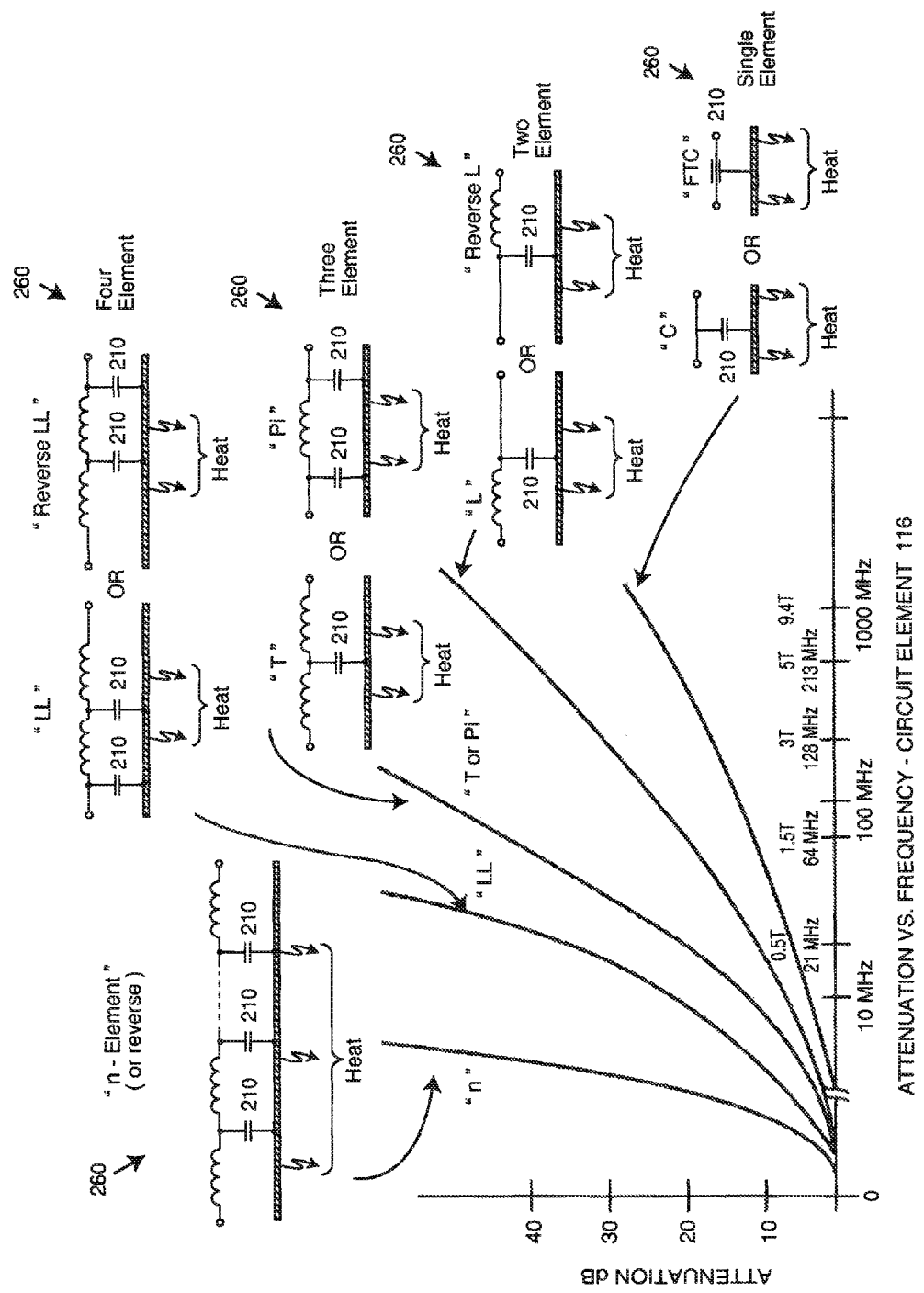
FIG. 79 illustrates a family of lowpass filters indicating the present invention can be anything from a simple diverter capacitor 140 to an "n" element lowpass filter.

FIG. 79 illustrates a family of lowpass filters 260 that all incorporate diverter capacitors 210 of the present invention. As can be seen, these lowpass filters 260 incorporate a variety of capacitors 210 ranging from a simple MLCC chip capacitor "C" to a 3-terminal "feedthrough capacitor-FTC". These capacitors 210 can be combined in various ways with inductors to form "L," "reverse L," "T," "Pi," "LL," or "reverse LL" or "n-element" lowpass filters. In other words, any of the high power RF handling diverter capacitors of the present invention can be combined with any of the lowpass filter circuits as illustrated in FIG. 79 for the purpose of protecting AIMD electronics from EMI while at the same time pulling MRI induced energy from an implanted lead.

FIG. 80 illustrates an electrical schematic comprising a bandstop filter 258. As illustrated, the band stop filter 258 may be electrically coupled to any circuit trace of a medical device within the interior of the AIMD housing 124. Furthermore, the band stop filter 258 may be electrically coupled to any of the lowpass filter circuits 260 as previously described in FIG. 79.

FIG. 81 illustrates an L-C trap filter 262 that can be incorporated to any of the circuits illustrated in FIG. 79 or FIG. 80.

FIG. 82 illustrates an electrical schematic embodying an AIMD in which the leads enter the AIMD at a hermetic seal 132 and then encounter any of the lowpass filter elements 260 as described in FIG. 79. In turn, there is a bandstop filter 258 and then an L-C trap filter 262 between the circuit trace and the AIMD housing 124. The AIMD housing 124 acts as a heat 218a or energy dissipating surface.

FIG. 83 is similar to FIG. 82 except in this case, the general lowpass filter 260 is in its simplest form. In this case, the general lowpass filter 260 is a feedthrough capacitor 210' which is in turn, connected in series with a bandstop filter 258 which is in turn connected with an L-C trap filter 262 disposed between the circuit trace or lead wire and the AIMD housing 124.

Figure 84:
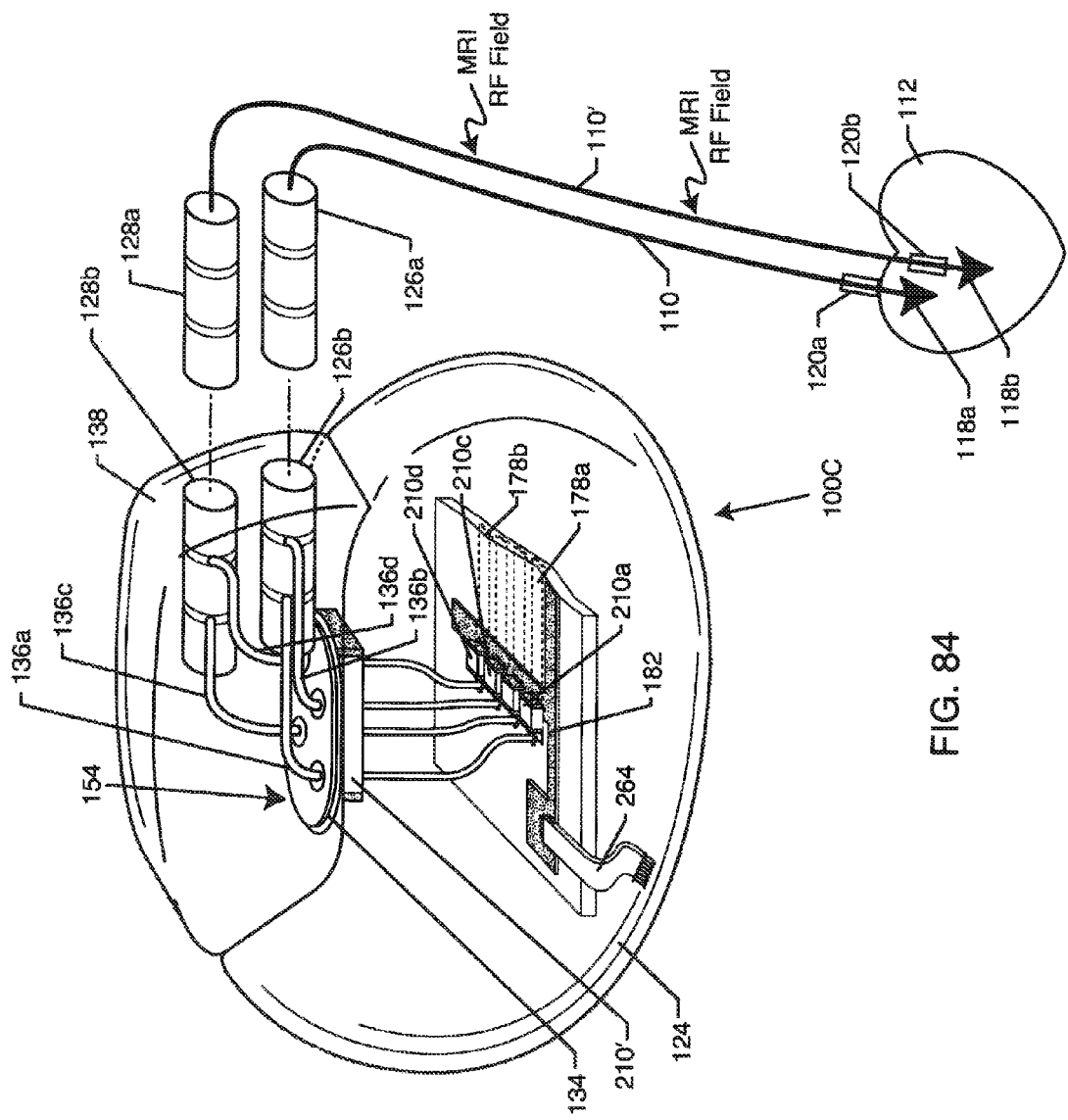
FIG. 84 illustrates a cardiac pacemaker with a diverter feedthrough capacitor and also a circuit board mounted chip capacitor filter which forms a composite filter and also spreads out heat generation.

FIG. 84 shows a dual chamber bipolar cardiac pacemaker 100C with leads implanted into the right atrium and right ventricle of the heart 112. As shown, header block 138 comprises industry standard IS-1 connectors 126, 128. MRI energy is shown being induced on the implanted leads 110 and 110'. As this energy enters the pacemaker housing 124, it encounters diverter capacitor 210'. The diverter capacitor 210' is designed to dissipate high RF power in accordance with the present invention. Accordingly, diverter capacitor 210' has a low dielectric loss at high frequency and also very low high frequency ESR. In addition, it may have any one of the aforementioned heat dissipating structures described. In this case, there is a secondary row of MLCC chip capacitors 210a through 210d that are mounted at a location distant from the primary diverter capacitor 210'. In this case, the primary diverter capacitor could have a lower capacitance value and the rest of the capacitance is comprised of either board mounted capacitors 210a through 210d or the like. As shown, the circuit board comprises a ground circuit trace 182 that is connected through a low impedance RF conductor or strap 264. This low impedance is important to conduct MRI RF currents efficiently to the housing 124 of the AIMD. In order to spread out heat, multiple straps 264 can be used (not shown). A major advantage of the structure shown in FIG. 84 is that by spreading out the filtering function, RF heat or MRI RF energy induced heat is dissipated or spread out over much larger areas. This avoids hot spots on the AIMD housing 124.

Figure 85:
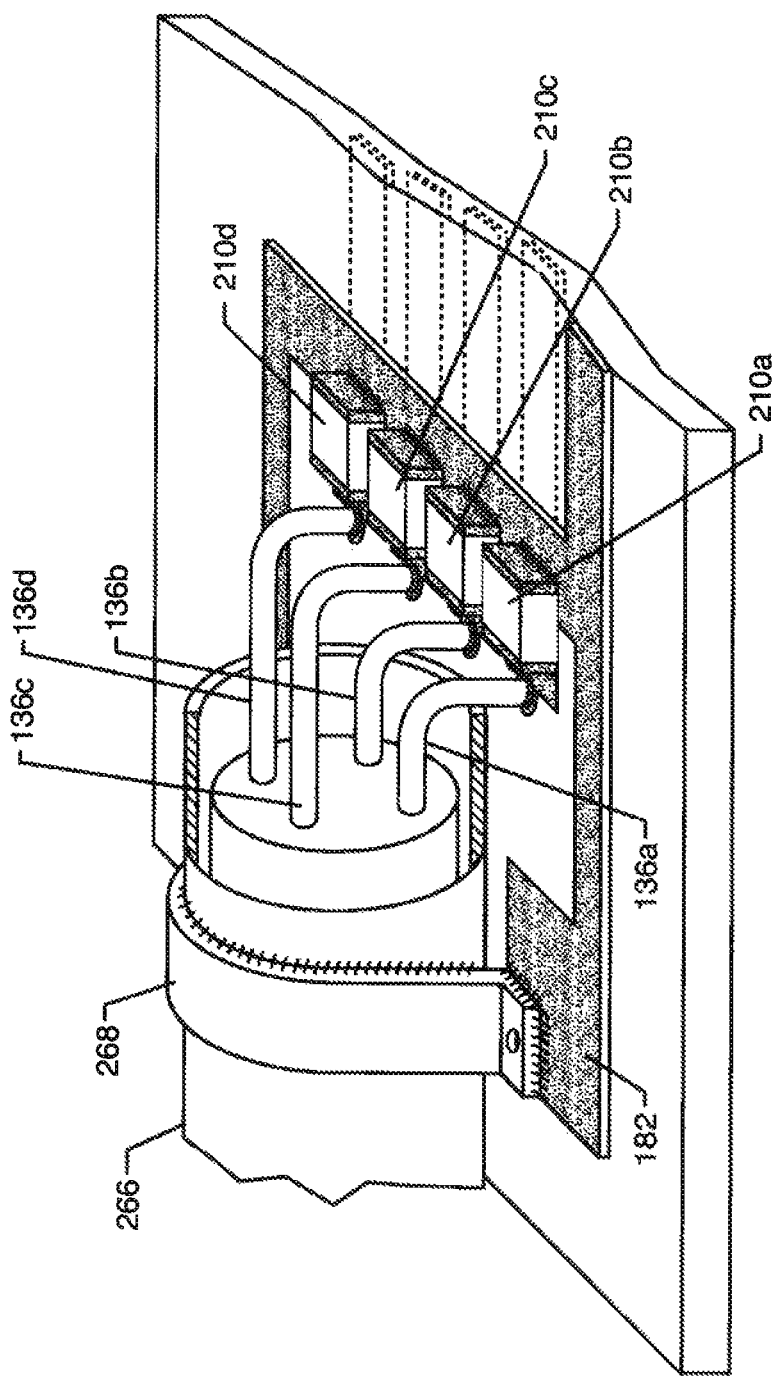
FIG. 85 is a fragmented perspective view of an EMI shield conduit mounted to a circuit board having multiple MLCC chip capacitors.

FIG. 85 shows an alternative embodiment to FIG. 84. A circuit board and chip capacitors 210a through 210d as previously described in FIG. 84 are shown. However in this embodiment, the grounded circuit trace 182 does not need a ground strap or conductor 264 to the AIMD housing. Instead, a shielded conduit assembly 266 is attached to the ferrule of the hermetic terminal (not shown). This shielded conduit 266 is grounded with a strap 268 which is connected to the ground circuit trace 182. This type of EMI shielded conduit assembly is more thoroughly described in U.S. Pat. No. 8,095,224 to Truex et al., the contents of which are incorporated herein by reference.

Figure 86:
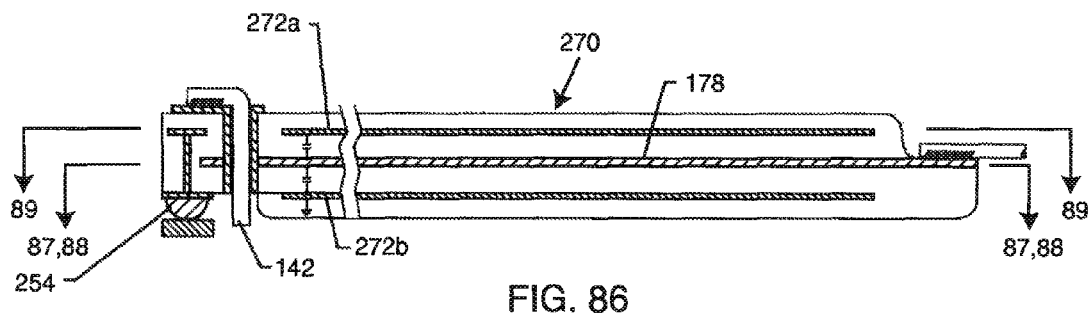
FIG. 86 is a cross-sectional view of an improved flex cable embodying the present invention.

FIG. 86 shows a cross-sectional view of a flex cable or circuit board 270. The flex cable or circuit board 270 is attached on the left using a ball grid array (BGA) type attachment 254. Attachment 254 is further connected to a conductor 142 that goes through a hermetic seal 132 of an AIMD (not shown). These types of flexible circuit traces or substrates are also described in U.S. Pat. No. 8,095,224 to Truex et al., the contents of which are incorporated herein by reference.

Figure 87:
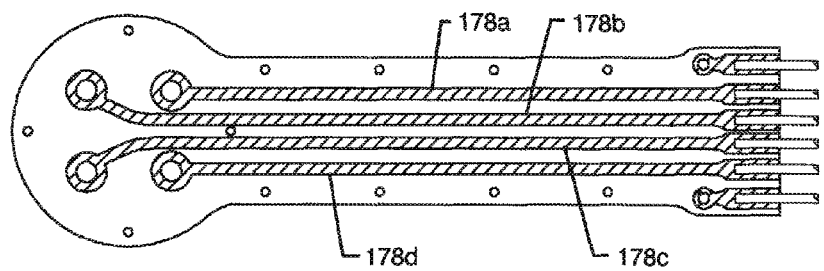
FIG. 87 is a sectional view taken along line 87-87 of FIG. 86.

FIG. 87 shows a cross sectional view generally taken from section 87-87 of FIG. 86 and shows the conductive circuit traces 178a through 178d.

Figure 88:
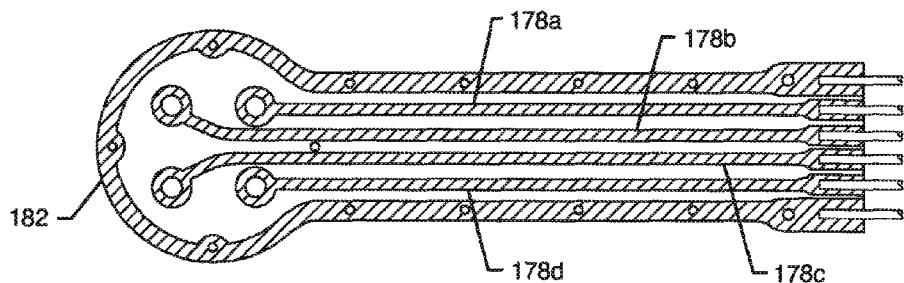
FIG. 88 is a sectional view taken along the line 88-88 of FIG. 86, illustrating an alternative to the internal circuit traces described with respect to FIG. 87.

FIG. 88 illustrates a cross sectional view generally taken from section 88-88 of FIG. 86 and shows an optional embodiment wherein a ground shield 182 surrounds the four circuit traces 178a through 178d.

Figure 89:
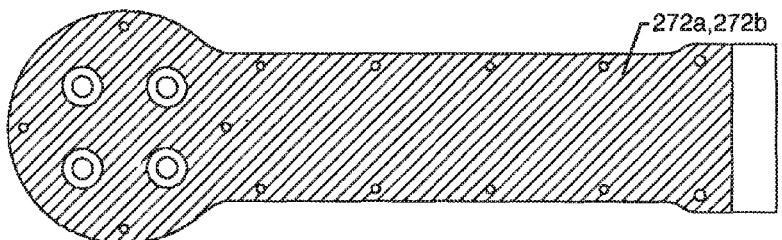
FIG. 89 is a sectional view taken along line 89-89 of FIG. 86, illustrating one of a pair of coaxially surrounding shields disposed about the circuit trace.

FIG. 89 is a cross sectional view taken generally from section 89-89 of FIG. 86 and illustrates shield layers 272a, 272b. These shield layers 272a, 272b are designed to surround each of the circuit trace layers 178 as previously described in FIG. 87 or 88. These shields 272a, 272b are not absolutely required, but greatly assist in preventing re-radiation of electromagnetic interference inside of the AIMD housing 124. This re-radiation of EMI can be very dangerous as it can couple to sensitive AIMD circuits and disrupt the proper functioning of the AIMD.

Figure 90:
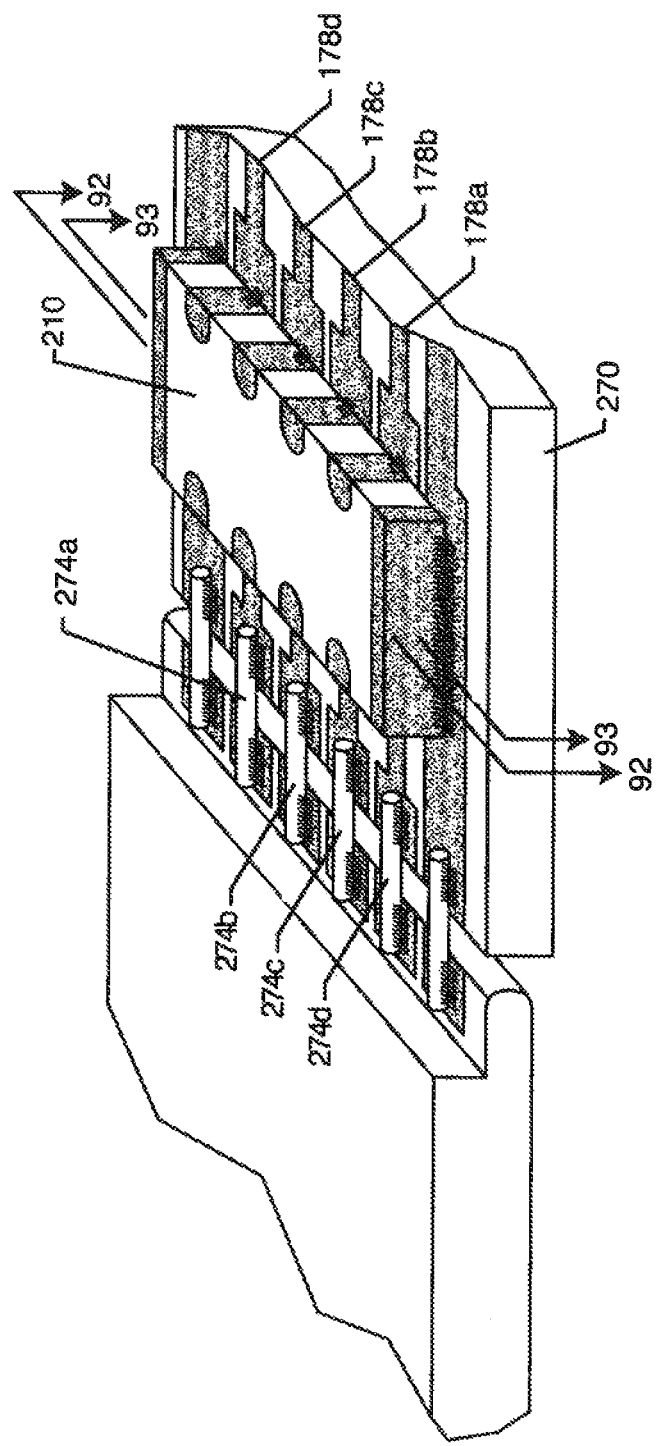
FIG. 90 is a perspective view of the flex cable of FIG. 86 connected to a circuit board or substrate having a flat-through capacitor.

FIG. 90 illustrates an embodiment in which the circuit traces 178a through 178d of FIGS. 86 through 89 are connected to a circuit board or substrate 270. Electrical attachments 274 are made to active circuit traces and in turn to a multi-element flat-through diverter capacitor 210. This three-terminal flat-through capacitor is very similar to that previously described in FIGS. 24 and 25 except that it has four capacitors embedded in a single structure. Capacitor 210 may replace the individual capacitor 210a through 210d as previously illustrated in FIG. 84 or capacitors 210a through 210d as previously described in FIG. 85.

Figure 91:
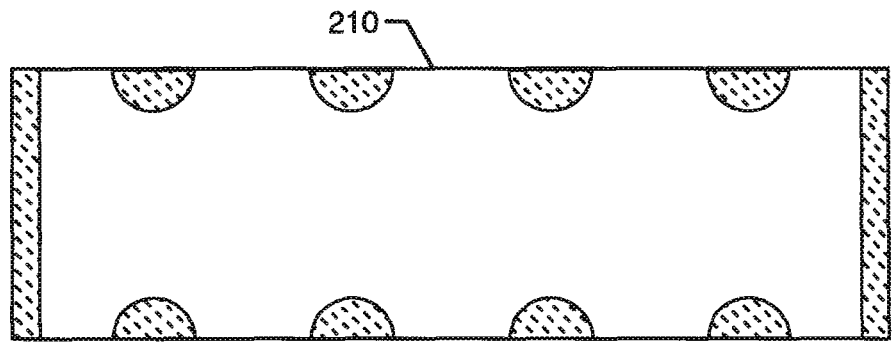
FIG. 91 is the top view of the flat-through capacitor from FIG. 90.

FIG. 91 shows a top view of the flat-through diverter capacitor 210 of FIG. 90.

Figure 92:
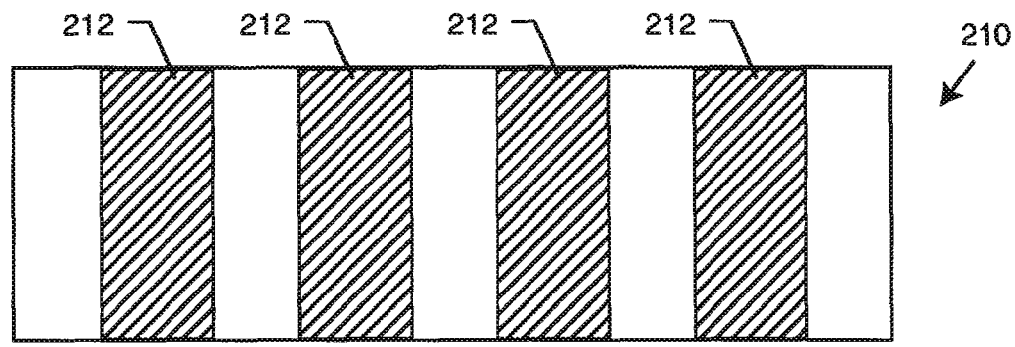
FIG. 92 illustrates the active electrode plates of the flat-through capacitor of FIGS. 90 and 91.

FIG. 92 is a cross sectional view taken generally from section 92-92 of FIG. 90 and shows the active electrode plates 212 of the flat-through diverter capacitor 219 of FIG. 90.

Figure 93:
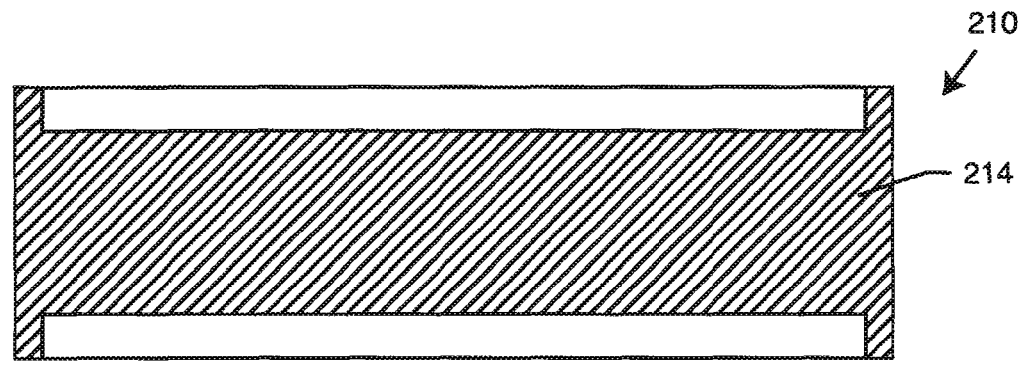
FIG. 93 illustrates the ground electrode plate set of the flat-through capacitor of FIGS. 90 and 91.

FIG. 93 is a cross sectional view taken generally from section 93-93 of FIG. 90 and shows the ground electrode plate 214 set of the flat-through capacitor 210 of FIG. 90.

Accordingly, from all of the foregoing it will be appreciated that this invention addresses the problems created when the radio frequency (RF) pulsed field of MRI couples to an implanted lead in such a way that electromagnetic forces (EMFs), voltages and current are induced in the lead. The amount of energy that is induced is related to a number of complex factors, but in general, is dependent upon the local electric field that is tangent to the lead and the integral electric field strength along the lead. In certain situations, these EMFs can cause currents to flow into distal electrodes or in the electrode interface with body tissue. It has been documented that when this current becomes excessive, that overheating of the lead or its associated electrodes can occur. In addition, overheating of the associated interface with body tissue can also occur.

There have been cases of overheated electrode damage to cardiac tissue which has resulted in loss of capture of cardiac pacemaking pulses. Furthermore, with respect to neurostimulators, neurological tissue damage severe enough to result in brain damage or multiple limb amputations have also been documented.

The present invention relates generally to methods and apparatus for redirecting RF energy to locations other than the distal tip electrode-to-tissue interface. In addition, the present invention provides electromagnetic interference (EMI) protection to sensitive active implantable medical device (AIMD) electronics. The redirection of this RF energy is generally achieved by the use of frequency selective devices, such as inductors, capacitors and filtered networks. As described in U.S. Pat. No. 7,689,288, to Stevenson et al., the contents of which are incorporated herein by reference, filtered energy dissipation networks can range from a single capacitor, such as a feedthrough capacitor, to more complex filters that may include L-C traps and/or L-C bandstop filters co-operating in various ways with C, L, Pi, T or n-element lowpass filters. In general, this is accomplished through frequency selective lowpass filters or series resonant LC trap filters wherein the RF energy can be redirected to another surface or is converted to heat. In all of the above described frequency selective networks, it is the capacitor(s) (co-operating with other circuit elements) which divert energy from an implantable lead system to the conductive housing of an AIMD. The relatively large surface area of the AIMD housing acts as an energy dissipating surface (EDS) wherein a significant amount of the MRI energy can be harmlessly dissipated without significant temperature rise. However, the lowpass filter also known as diverter capacitor elements must be designed to handle a very high amount of RF current and power. Accordingly, the capacitor's internal resistive or real losses known as equivalent series resistance (ESR) must be kept quite low. The present invention is directed to various embodiments of MRI diverter capacitor designs that minimize the diverter capacitor's equivalent series resistance (ESR). In addition, the capacitor is also designed to direct heat to relatively large surface area heat dissipation surfaces, thereby creating an efficient heat removal system. These high RF power/low ESR diverter capacitors are an important feature of the filter network of the present invention for diverting induced RF energy from an implanted lead to an energy dissipating surface, particularly a conductive housing of an AIMD.

These implantable lead systems are generally associated with AIMDs, such as cardiac pacemakers, cardioverter defibrillators, neurostimulators and the like. The present invention can also be incorporated with external devices, such as external pacemakers, externally worn neurostimulators (such as pain control spinal cord stimulators) and the like. It will be shown that for a given geometry constraint, a preferred means of reducing the diverter capacitor's ESR is to select the most ideal dielectric type so that its dielectric loss tangent (dielectric losses) is insignificant at the MRI RF pulsed frequency(ies). Of particular importance in the present invention is selection of a capacitor dielectric with the proper dielectric constant (k) value. The preferred capacitor dielectric will have a k of a sufficiently low value to thereby increase the number of active and ground electrode plates in the capacitor. This design feature dramatically reduces the ohmic losses in the capacitor at high frequency. Therefore, to accomplish a relatively high electrode plate count, a low k capacitor dielectric is used. A non-limiting example of one such dielectric material is an EIA standard, Class I dielectric material, COG, which is also known as NPO (negative-positive-zero). (Refer to EIA Standard ANSI/EIA-198-1-F-2002).

In general, at first glance, using a Class I dielectric is counterintuitive. For example, consider a typical X7R MLCC dielectric, with a dielectric constant of around 2500. With such a high efficiency dielectric material having a relatively high dielectric constant, it would be possible to build, for example, a 1000 picofarad filter capacitor with two to four electrode plates. Now consider using a Class 1 COG dielectric, wherein the dielectric constant is less than 100. A typical capacitor comprising the COG dielectric material would generally require greater than 20 or even 40 electrode plates to achieve the same capacitance value. Such a design would, however, provide a capacitor with a relatively large thickness and would also require significantly more precious metal in its manufacturing. A capacitor of this design is generally not desired.

Nonetheless, the benefit of incorporating a COG dielectric material within the capacitor design is generally a reduction of the capacitor's ESR at MRI RF-pulsed frequencies. If designed properly, the RF energy heat that is produced when positioned within an MRI scanner can be significantly reduced such that heat that results from RF energy does not pose harm to biological tissue.

One purpose of these low ESR diverter capacitors and related lowpass filter circuits is to provide electromagnetic interference (EMI) filtering in order to protect sensitive AIMD electronic circuits from malfunctioning in the presence of MRI RF noise. Another purpose of these circuits, as described in the present invention, is to draw MRI induced energy out of the lead and redirect said energy to the AIMD housing. This has the effect of reducing the energy that would reach the distal tip electrode or the interface with body tissue. By redirecting said energy to locations at a point distant from the distal electrodes, ideally the AIMD housing, this minimizes or eliminates hazards associated with overheating of said distal electrodes during diagnostic procedures, such as MRI.

For maximum RF energy transfer out of the lead, frequency selective diverter circuits are needed which decouple and transfer energy which is induced onto implanted leads from the MRI pulsed RF field to an energy dissipating surface. Importantly, while decoupling and transferring such energy, it is extremely important that the diverter circuits do not themselves overheat thereby creating hot spots on the AIMD housing, which could damage tissue, for example, in a pacemaker pectoral pocket. Recent experiments by the inventors have seen temperature rises from 4 to 10 degrees C. on the pacemaker housing directly over the location of the feedthrough capacitor during a 4 watt/kilogram MRI scan. In general, in the prior art, MLCC capacitors are really not indicated for high power RF applications. The reason for this is that the impedance (capacitive reactance) drops so low that extremely high RF currents end up flowing through the capacitor's electrode plates. During a 4 watt/kilogram MRI scan where 16 to 20 volts may be induced at the AIMD input, the diverter capacitor may be handling anywhere from 0.5 to 4 amps of RF current. If the ESR of the capacitor, for example, was 0.5 ohms and the capacitor was diverting 2 amps, then the $I^2R$ loss would be on the order of 2 watts. Two watts of dissipation on this small component would cause it to overheat significantly. The present invention fulfills these needs and provides other related advantages.

The RF diverting circuits, in general, conduct MRI induced RF energy from the lead or its associated lead wires to an EDS such as the housing of the AIMD. The design of the diverter circuit is very important. First of all, the diverter circuit should appear as a very low impedance at MRI RF frequencies such that a maximum amount of RF energy is diverted from the lead to the EDS. In addition, it is also desirable that the diverter element be designed such that it does not overheat. It has been shown, through modeling and measurements, that the MRI induced RF energy at the point of input to an AIMD, such as a cardiac pacemaker, can range from about 16 to about 50 volts at about 64 MHz. Assuming an RF input voltage of 20 volts and the impedance of the diverter element capacitor is around 4 ohms, this means that about 5 amps of RF current would be flowing through said diverter element. Therefore, its ESR must be quite low so that it does not overheat. It can be readily seen that such a high value of ESR associated with a higher current would quickly result in failure of the component or other damage. On the other hand, if the diverter capacitor's ESR was 100 milliohms and the RF current that it was handling was 2 amps, then the power dissipated in the same example would be only 0.4 watts. Even 0.4 watts will still create a significant temperature rise on the diverter capacitor component. The present invention describes ways of either conducting or convecting that heat away so that it does not create a hot spot on the AIMD housing.

For a particular AIMD, the geometry of the diverter capacitor is usually constrained by the AIMD design generally comprising, circuit topology, size, and weight considerations. For AIMDs, the filter capacitance value in picofarads is heavily constrained by the application of its use. For example, too high of a capacitance value will tend to load down and distort therapeutic wave forms. In addition, too high of a filter capacitance value can distort pacemaker pulses or seriously degrade ICD high voltage pulse discharges. In the experience of the inventors, capacitance values for EMI lowpass filter capacitors typically range from about 10 picofarads to as high as about 20,000 picofarads. For pacemakers, capacitance values as low as about 350 picofarads to as high as 10,000 picofarads are generally used. For monolithic ceramic capacitors, which tend to comprise dielectric materials having very high dielectric constants, these capacitance values are generally very low. In many prior art designs, only a very few (less than 10) electrode plates are required. In many designs using typical EIA Standard X7R dielectrics, there are only two or three electrode plates required. However, these prior art capacitor designs comprising a relatively low number of electrode plates, generally of 10 or less, result in a capacitor having significantly high electrode plate resistance of about 0.5 ohms or more. Such a capacitor with a relatively high electrode plate resistance, results in the generation of a great deal of heat as the capacitor diverts MRI RF-pulsed frequencies, which is not desirable.

Furthermore the mounting location of the diverter capacitor within an AIMD is also typically constrained by proper EMI design practices. Generally, EMI filters are designed such that undesirable RF energy is diverted at the point of lead ingress to the AIMD housing, as opposed to letting the EMI inside the AIMD housing and trying to filter it further downstream, such as on an internal circuit board. In a preferred embodiment, at least one of the low ESR diverter capacitors of the present invention is mounted directly to the multi-pin hermetic seal terminal of the AIMD. This is an ideal location both to divert RF energy before it can enter the AIMD housing but is also optimal for heat conduction and dissipation. Even with low ESR, the diverter capacitor will still be dissipating a significant amount of energy. This means, even with low ESR, the diverter capacitor is creating heat which must be conducted or convected away so that a hot spot does not occur on the AIMD housing at or near the filter capacitor. Therefore, by diverting both the RF energy and heat to the relatively large surface area of the housing of the AIMD the MRI RF energy can be dissipated with only a small temperature rise that does not adversely affect body tissue. Although the present invention has applicability to medical devices it is contemplated that it can be utilized in nonmedical applications. The high power filtered feedthough capacitor assembly of the present invention is an EMI filter that is applicable to a wide array of commercial, military and space applications wherein a shielded enclosure must pass through leadwires in non-conductive relation to electronics circuits inside the enclosure. In this case, the pass through may be an insulator that is hermetic or non-hermetic. This is an important application of the present invention to military "black boxes" that may be in close proximity to a high RF power source such as an RF transmitter, radar, or the like.

Although several embodiments of the invention have been described in detail for purposes of illustration, various modifications of each may be made without departing from the spirit and scope of the invention. Accordingly, the invention is not to be limited, except as by the appended claims.

What is claimed is:

1. An RF capacitor, comprising:
   a) a dielectric body comprising a dielectric sidewall extending along a longitudinal axis from a dielectric body first end to a dielectric body second end;
   b) a terminal member supported in the dielectric body and comprising a length extending to first and second terminal ends spaced from the respective first and second dielectric body ends;
   c) a plurality of active electrode plates supported in the dielectric body, each active electrode plate having an active electrode length extending from a first active edge to a second active edge electrically connected to the terminal member,
   d) a plurality of ground electrode plates supported in the dielectric body, each ground electrode plate having a ground electrode length extending from a first ground edge to a second ground edge electrically connectable to an energy dissipating surface comprising a conductive ferrule or an active implantable medical device (AIMD) housing,
   e) wherein the ground and active electrode plates are in an interleaved, spaced relationship with only a portion of the active and ground electrode lengths extending from the first active and ground edges to the respective second active and ground edges being vertically above or below the other of the active and ground electrode plates in an orientation extending along the longitudinal axis of the dielectric body; and
   f) at least three extra ground electrode plates in the dielectric body, each extra ground electrode plate extending from an extra ground electrode plate first edge electrically connectable to the energy dissipating surface to an extra ground electrode plate second edge spaced from the terminal member and being in a spaced relationship with the plurality of interleaved active and ground electrode plates along the longitudinal axis without any active electrode plates being interleaved between the three extra ground electrode plates.

2. The capacitor of claim 1 wherein the capacitor includes at least ten interleaved active and ground electrode plates.

3. The capacitor of claim 1 wherein the capacitor has a capacitance from 10 to 10,000 picofarads.

4. The capacitor of claim 1 comprising a single or multi-element lowpass filter.

5. The capacitor of claim 4 wherein the single or multi-element lowpass filter is electrically coupled with one or more bandstop filters, one or more L-C trap filters, or both, in any order or circuit configuration.

6. The capacitor of claim 1 being selected from the group consisting of at least one two-terminal chip capacitor, an MLCC capacitor, a three-terminal feedthrough-type capacitor, a flat-through capacitor, and an X2Y attenuator.

7. The capacitor of claim 4 wherein the multi-element lowpass filter is selected from the group consisting of a C, L, reverse L, Pi, T, LL, reverse LL, and an n-element filter.

8. The capacitor of claim 1 wherein the capacitor is disposed at or adjacent to a point of ingress or egress of an implanted lead conductor into a housing for the AIMD.

9. The capacitor of claim 1 wherein the capacitance varies no more than plus or minus one percent from minus 55° C. to plus 125° C.

10. The capacitor of claim 1 wherein the ground electrode plates each comprise closely spaced pairs of dual ground electrode plates.

11. The capacitor of claim 1 wherein the active electrode plates each comprise closely spaced pairs of dual active electrode plates.

12. The capacitor of claim 1 wherein the ground electrode plate each comprise closely spaced triple or n ground electrode plates.

13. The capacitor of claim 1 including an electrically non-conductive thermal-setting thermally conductive adhesive configured for thermally conducting heat energy away from the capacitor to the energy dissipating surface.

14. The capacitor of claim 1 configured to support a connection material that is electrically connectable from the second ground edge to a conductive ferrule of a hermetic seal or the AIMD housing comprises a thermal-setting conductive adhesive selected from the group consisting of conductive particles, silver flakes, electrically conductive flakes, electrically conductive rods, electrically conductive tubes, electrically conductive whiskers, electrically conductive fibers, and electrically conductive nano particles.

15. The capacitor of claim 1 wherein at least a second extra ground electrode plate is embedded within the dielectric material at an opposite side of the interleave from the first extra at least three ground electrode plates.

16. The capacitor of claim 1 including a plurality of ground electrode plates extending to substantially the periphery of the capacitor.

17. The capacitor of claim 16 including a high thermal conductivity material or a high thermally conductive overlay configured for transferring heat energy from the capacitor to a conductive ferrule, the capacitor being disposed inside the ferrule.

18. The capacitor of claim 17 wherein the ferrule is connectable to the energy dissipation surface.

19. The capacitor of claim 17 wherein the thermally-conductive overlay extends from the conductive ferrule over a non-body fluid side of the capacitor.

20. The capacitor of claim 17 including a hermetic insulator disposed within the conductive ferrule, the hermetic insulator having at least one insulator ground electrode plate conductively coupled to the ferrule.

21. The capacitor of claim 1 including a weld shield attached to the conductive ferrule.

22. The capacitor of claim 1 including a thickened metallization layer disposed about an outside perimeter of the capacitor and conductively coupled to the at least one ground electrode plate.

23. The capacitor of claim 22 wherein the thickened metallization layer is selected from the group consisting of metal bearing glass frits or Aluminum, Aluminum Nitride, Beryllium, Copper, Multiwalled Carbon Nanotube, Isotropically Enriched Diamond, Graphene, Gold, Silver, Platinum, and materials with thermal conductivity greater than 150 watts per meter Kelvin near 300K.

24. The capacitor of claim 1 wherein a thermally conductive ceramic is disposed within the conductive ferrule and positioned between the capacitor and an alumina ceramic insulator.

25. The capacitor of claim 1 wherein a thermally conductive washer is disposed between the capacitor and a hermetic seal insulator positioned within the conductive ferrule.

26. The capacitor of claim 25 wherein the thermally-conductive washer is selected from the group consisting of Aluminum, Aluminum Nitride, Beryllium, Copper, Multiwalled Carbon Nanotube, isotropically Enriched Diamond, Graphene, Gold, Silver, Platinum, and materials with thermal conductivity greater than 150 watts per meter Kelvin near 300K.

27. The capacitor of claim 1 wherein the capacitor is disposed inside the conductive ferrule, the ferrule including a capture flange.

28. The capacitor of claim 1 including a heat conductive structure affixed to a periphery of the capacitor.

29. The capacitor of claim 28 wherein the heat conductive structure comprises a plurality of convection fins.

30. A capacitor, comprising:
a) a dielectric body comprising a dielectric sidewall extending along a longitudinal axis from a dielectric body first end to a dielectric body second end;
b) a terminal member supported in the dielectric body and comprising a length extending to first and second terminal ends spaced from the respective first and second dielectric body ends;
c) a plurality of active electrode plates supported in the dielectric body, each active electrode plate having an active electrode length extending from a first active edge to a second active edge electrically connected to the terminal member,
d) a plurality of ground electrode plates supported in the dielectric body, each ground electrode plate having a ground electrode length extending from a first ground edge to a second ground edge electrically connectable to an energy dissipating surface comprising a conductive ferrule or an active implantable medical, device (AIMD) housing,
e) wherein there are at least ten ground and ten active electrode plates in an interleaved, spaced relationship with only a portion of the active and ground electrode lengths extending from the first active and ground edges to the respective second active and ground edges being vertically above or below the other of the active and ground electrode plates in an orientation extending along the longitudinal axis of the dielectric body; and
f) at least three extra ground electrode plates in the dielectric body, each extra ground electrode plate extending from an extra ground electrode plate first edge electrically connectable to the energy dissipating surface to an extra ground electrode plate second edge spaced from the terminal member and being in a spaced relationship with the plurality of interleaved active and ground electrode plates along the longitudinal axis without any active electrode plates being interleaved between the three extra ground electrode plates;
g) wherein the capacitor has a capacitance of from 10 to 20,000 picofarads, and
h) wherein the dielectric has a dielectric constant of 200 or less, and a temperature coefficient of capacitance (TCC) within the range of plus 400 to minus 7112 parts per million per degree centigrade (ppm/° C.);
i) wherein the capacitor's dielectric loss tangent in ohms is less than five percent of the capacitor's equivalent series resistance (ESR) at the desired center frequency or desired range of frequencies; and
j) wherein the equivalent series resistance is less than 100 milliohms.

31. A capacitor, comprising:
a) a dielectric body comprising a dielectric sidewall extending along a longitudinal axis from a dielectric body first end to a dielectric body second end;
b) a terminal member supported in the dielectric body and comprising a length extending to first and second terminal ends spaced from the respective first and second dielectric body ends;
c) a plurality of active electrode plates supported in the dielectric body, each active electrode plate having an active electrode length extending from a first active edge to a second active edge electrically connected to the terminal member,
d) a plurality of ground electrode plates supported in the dielectric body, each ground electrode plate having a ground electrode length extending from a first ground edge to a second ground edge electrically connectable to an energy dissipating surface comprising a conductive ferrule or an active implantable medical device (AIMD) housing, e) wherein the ground and active electrode plates are in an interleaved, spaced relationship with only a portion of the active and ground electrode lengths extending from the first active and ground edges to the respective second active and ground edges being vertically above or below the other of the active and ground electrode plates in an orientation extending along the longitudinal axis of the dielectric body; and f) at least three extra ground electrode plates in the dielectric body, each extra ground electrode plate extending from an extra ground electrode plate first edge electrically connectable to the energy dissipating surface to an extra ground electrode plate second edge spaced from the terminal member and being in a spaced relationship with the plurality of interleaved active and ground electrode plates along the longitudinal axis without any active electrode plates being interleaved between the three extra ground electrode plates;

g) wherein the capacitor has a capacitance of from 10 to 20,000 picofarads, and h) wherein the dielectric has a dielectric constant of 200 or less and a temperature coefficient of capacitance (TCC) within the range of plus 400 to minus 7112 parts per million per degree centigrade (ppm/° C.);

i) wherein an equivalent series resistance (ESR) of the capacitor at a designated MRI center frequency or designated range of frequencies is less than 0.1 ohms;

j) wherein the capacitor's dielectric loss tangent in ohms is less than five percent of the ESR at the designated MRI center frequency or designated range of frequencies.

\* \* \* \* \*

UNITED STATES PATENT AND TRADEMARK OFFICE
CERTIFICATE OF CORRECTION

Page 1 of 1

PATENT NO. : 8,855,768 B1
APPLICATION NO. : 14/088849
DATED : October 7, 2014
INVENTOR(S) : Robert Shawn Johnson et al.

It is certified that error appears in the above-identified patent and that said Letters Patent is hereby corrected as shown below:

In the Claims,

Column 38, line 16 (Claim 20, line 19) after the word "medical" delete the ","

Signed and Sealed this
Seventeenth Day of March, 2015

Michelle K. Lee
*Director of the United States Patent and Trademark Office*